United States Patent
Cooymans et al.

(10) Patent No.: US 9,321,767 B2
(45) Date of Patent: Apr. 26, 2016

(54) AZABENZIMIDAZOLES AS RESPIRATORY SYNCYTIAL VIRUS ANTIVIRAL AGENTS

(71) Applicant: JANSSEN SCIENCES IRELAND UC, Co, Cork (IE)

(72) Inventors: Ludwig Paul Cooymans, Beerse (BE); Samuël Dominique Demin, Antwerp (BE); Lili Hu, Mechelen (BE); Tim Hugo Maria Jonckers, Edegem (BE); Pierre Jean-Marie Bernard Raboisson, Rosieres (BE); Abdellah Tahri, Anderlecht (BE); Sandrine Marie Helene Vendeville, Woluwe-Saint-Pierre (BE)

(73) Assignee: Janssen Sciences Ireland UC, Co Cork (IE)

( * ) Notice: Subject to any disclaimer, the term of this patent is extended or adjusted under 35 U.S.C. 154(b) by 0 days.

(21) Appl. No.: 14/546,016

(22) Filed: Nov. 18, 2014

(65) Prior Publication Data

US 2015/0073012 A1  Mar. 12, 2015

Related U.S. Application Data

(62) Division of application No. 13/993,141, filed as application No. PCT/EP2011/073014 on Dec. 16, 2011, now Pat. No. 8,927,720.

(30) Foreign Application Priority Data

Dec. 16, 2010 (EP) .................................. 10195469
Mar. 31, 2011 (EP) .................................. 11160724

(51) Int. Cl.
    C07D 471/04 (2006.01)
    A61K 31/437 (2006.01)
    A61P 31/12 (2006.01)

(52) U.S. Cl.
    CPC .................................. *C07D 471/04* (2013.01)

(58) Field of Classification Search
    CPC ..... C07D 471/04; A61K 31/437; A61P 31/12
    USPC .......................................... 514/303; 546/118
    See application file for complete search history.

(56) References Cited

U.S. PATENT DOCUMENTS

| | | | |
|---|---|---|---|
| 6,489,338 B2 | 12/2002 | Yu et al. | |
| 6,506,738 B1 | 1/2003 | Yu et al. | |
| 6,534,535 B1 | 3/2003 | Zhu et al. | |
| 6,919,331 B2 | 7/2005 | Yu et al. | |
| 7,361,657 B2 | 4/2008 | Janssens et al. | |
| 7,528,149 B2 | 5/2009 | Janssens et al. | |
| 2002/0016309 A1 | 2/2002 | Yu et al. | |
| 2004/0166137 A1 | 8/2004 | Lackey | |
| 2011/0009444 A1 | 1/2011 | Dubois et al. | |
| 2013/0261151 A1 | 10/2013 | Cooymans et al. | |
| 2013/0267508 A1 | 10/2013 | Cooymans et al. | |
| 2013/0267555 A1 | 10/2013 | Cooymans et al. | |
| 2013/0267556 A1 | 10/2013 | Cooymans et al. | |
| 2013/0324527 A1 | 12/2013 | Cooymans et al. | |

FOREIGN PATENT DOCUMENTS

| | | |
|---|---|---|
| WO | WO 98/01428 | 1/1998 |
| WO | WO 00/20400 | 4/2000 |
| WO | WO 00/35886 | 6/2000 |
| WO | WO 01/57020 | 8/2001 |
| WO | WO 01/95910 | 12/2001 |
| WO | WO 02/26228 | 4/2002 |
| WO | WO 03/053344 | 4/2003 |
| WO | WO 2006/062465 | 6/2006 |

OTHER PUBLICATIONS

Mackman; J. Med. Chem. 2015, 58, 1630-1643.*
Banker, et al., Modern Pharmaceutics, 3 edition, 1996, pp. 451 and 596.
Wang, et al., "Respiratory Syncytial virus Fusion Inhibitors. Part 5: Optimization of Benzimidazole Substitution Patterns Towards Derivatives with Improved Activity", Biorganic and Medicinal Chemistry Letters, vol. 17, 2007, pp. 4592-4598.
Beaulieu, et al., "Improved Replicon Cellular Activity of Non-Nucleoside Allosteric Inhibitors of HCV NS5B Polymerase: From Benzimidazole to Indole Scaffolds", Biorganic & Medicinal Chemistry letters 16, 2006, pp. 4987-4993.
Goodman, et al, Biotransformation of Drugs:, The Pharmacological Basis of Therapeutics, $8^{th}$ ed., 1992, pp. 13-15.
Giampieri, et al., "Antiviral Activity of Indole Derivatives", Antiviral Research, vol. 83, 2009, pp. 179-185.
Wyde, et al., AWY Dentiviral Research, vol. 38, 1998, pp. 31-42.
Wolff, et al., "Burger's Medicinal Chemistry, $5^{th}$ edition", Part I, pp. 975-977, 1995.
Wermuth, "Molecular Variations Based on Isosteric Replacements", Practice of Medicinal Chemistry $3^{rd}$ edition, 2008, pp. 290-342.

(Continued)

*Primary Examiner* — Janet L Andres
*Assistant Examiner* — Daniel Carcanague

(57) ABSTRACT

A compound satisfying formula I, a prodrug, N-oxide, addition salt, quaternary amine, metal complex, or a stereochemically isomeric form thereof;

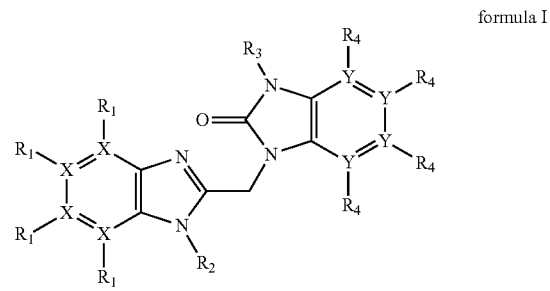

formula I compositions contain these compounds as active ingredient and processes for preparing these compounds and compositions

12 Claims, No Drawings

(56) References Cited

OTHER PUBLICATIONS

Yu, et al., "Respiratory Syncytial Virus Fusion Inhibitors. Part 4: Optimization for Oral Bioavailability" Biorganic & Medicinal Chemistry letters, vol. 17, 2007, pp. 895-901.
Silverman, et al., The Organic of Drug Design and Drug Action, pp. 29-34, 2004.
Pearce, et al., "E-Novo: An Automated Workflow for efficient Structure-Based Lead Optimization" J. Chem. Inf. Model, 2009, vol. 49, pp. 1797-1809.
Ito, et al., "A Medium-Term Rat Liver Bioassay for Rapid in Vivo Detection of Carcinogenic Potential of Chemicals" Cancer Science, 94(1) 2003, pp. 3-8.
Database Registry Chemical Abstracts Service, Columbus, Ohio, Assession No. RN 941045-14-3 and RN 931665-23-5.Entered STN: Jul. 4, 2007 and Apr. 22, 2007.
International Search Report—PCT/EP2011/073008, dated, Mar. 28, 2012.
International Search Report—PCT/EP2011/073011, dated, Mar. 27, 2012.
International Search Report—PCT/EP2011/073014, dated Mar. 28, 2012.
International Search Report—PCT/EP2011/073016, dated Mar. 27, 2012.
International Search Report—PCT/EP2011/073017, dated Mar. 28, 2012.
Hallak et al, "Glycosaminoglycan Sulfation Requirements for Respiratory Syncytial Virus Infection", Journal of Virology, vol. 74, No. 22 (Nov. 2000), pp. 10508-10513.
Tonelli et al, "Antiviral Activity of Benzimidazole Derivaties. I. Antiviral Activity of 1-Substituted-2-1(Benzotriazol-1/2-yl)methypenzimidazoles)", Chemistry & Biodiversity, vol. 5 (2008) pp. 2386-2401.
Yu, et al., "Respiratory Syncytial Virus Inhibitors. Part 2: Benzimidazole-2-one Derivatives", Bioorganic & Medicinal Chemistry Letters 14 (2004) pp. 1133-1137.

* cited by examiner

AZABENZIMIDAZOLES AS RESPIRATORY SYNCYTIAL VIRUS ANTIVIRAL AGENTS

CROSS REFERENCE TO RELATED APPLICATIONS

This application is a divisional of U.S. application Ser. No. 13//993,141, filed Jun. 11, 2013, which is the national stage under 35 U.S.C. 371 of PCT Application No. PCT/EP2011/073014, filed Dec. 16, 2011, which application claims priority from European Patent Application No. EP 10195469.1, filed Dec. 16, 2010, and European Patent Application No. EP 11160724.8, filed 31 Mar. 2011 the entire disclosures of which are hereby incorporated by reference in their entirety.

FIELD OF THE INVENTION

The invention concerns azabenzimidazoles having antiviral activity, in particular, having an inhibitory activity on the replication of the respiratory syncytial virus (RSV). The invention further concerns the preparation of these azabenzimidazoles, compositions comprising these compounds, and the compounds for use in the treatment of respiratory syncytial virus infection.

BACKGROUND

Human RSV or Respiratory Syncytial Virus is a large RNA virus, member of the family of Paramyxoviridae, subfamily pneumoviridae together with bovine RSV virus. Human RSV is responsible for a spectrum of respiratory tract diseases in people of all ages throughout the world. It is the major cause of lower respiratory tract illness during infancy and childhood. Over half of all infants encounter RSV in their first year of life, and almost all within their first two years. The infection in young children can cause lung damage that persists for years and may contribute to chronic lung disease in later life (chronic wheezing, asthma). Older children and adults often suffer from a (bad) common cold upon RSV infection. In old age, susceptibility again increases, and RSV has been implicated in a number of outbreaks of pneumonia in the aged resulting in significant mortality.

Infection with a virus from a given subgroup does not protect against a subsequent infection with an RSV isolate from the same subgroup in the following winter season. Re-infection with RSV is thus common, despite the existence of only two subtypes, A and B.

Today only three drugs have been approved for use against RSV infection. A first one is ribavirin, a nucleoside analogue, that provides an aerosol treatment for serious RSV infection in hospitalized children. The aerosol route of administration, the toxicity (risk of teratogenicity), the cost and the highly variable efficacy limit its use. The other two drugs, RespiGam® (RSV-IG) and Synagis® (palivizumab), polyclonal and monoclonal antibody immunostimulants, are intended to be used in a preventive way. Both are very expensive, and require parenteral administration.

Other attempts to develop a safe and effective RSV vaccine have all met with failure thus far. Inactivated vaccines failed to protect against disease, and in fact in some cases enhanced disease during subsequent infection. Life attenuated vaccines have been tried with limited success. Clearly there is a need for an efficacious non-toxic and easy to administer drug against RSV replication. It would be particularly preferred to provide drugs against RSV replication that could be administered perorally.

A reference entitles "imidazopyridine and imidazopyrimidine antiviral agents" is WO 01/95910 which, in fact, relates to benzimidazole antiviral agents. Herein compounds are presented to have antiviral activity, yet with $EC_{50}$ values over a wide range of from 0.001 µM to as high as 50 µM (which does not normally represent the desired biological activity). Another reference, relating to substituted 2-methyl-benzimidazole RSV antiviral agents, in the same range of activities is WO 03/053344. Another related background reference on compounds in the same range of activities, is WO 02/26228 regarding benzimidazolone antiviral agents. A reference on structure-activity relations, in respect of RSV inhibition, of 5-substituted benzimidazole compounds is X. A. Wang et al., Bioorganic and Medicinal Chemistry Letters 17 (2007) 4592-4598.

It is desired to provide new drugs that have antiviral activity. Particularly, it would be desired to provide new drugs that have RSV replication inhibitory activity. Further, it would be desired to retrieve compound structures that allow obtaining antiviral biological activities of the order of magnitude in the stronger regions of the prior art (i.e. at the bottom of the above-mentioned range of up to 50 µM), and preferably at a level of about the most active, more preferably of even stronger activity, than the compounds disclosed in the art. A further desire is to find compounds having oral antiviral activity.

SUMMARY OF THE INVENTION

In order to better address one or more of the foregoing desires, the invention, in one aspect, presents antiviral azabenzimidazole compounds represented by formula I, a prodrug, N-oxide, addition salt, quaternary amine, metal complex, or a stereochemically isomeric form thereof;

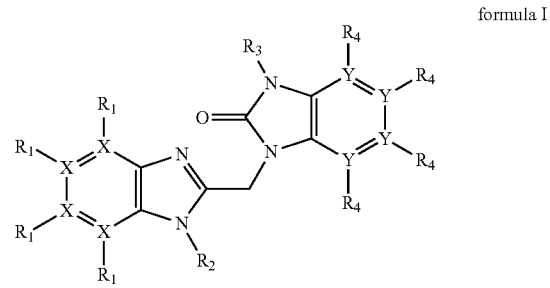

formula I wherein each X independently is C or N; at least one X=N; each Y independently is C or N;

$R_1$ is present when X=C and $R_1$ is selected from the group of H, halogen, $C_1$-$C_6$alkyl, $C_3$-$C_7$cycloalkyl, $C_1$-$C_6$alkoxy, $N(R_5)_2$, $CO(R_6)$, $CH_2NH_2$, $CH_2OH$, CN, C(=NOH)$NH_2$, C(=NOCH$_3$)$NH_2$, C(=NH)$NH_2$, $CF_3$, $OCF_3$, and $B(OH)_2$; B(O—$C_1$-$C_6$alkyl)$_2$;

$R_1$ is absent when X=N $R_2$—(CR$_7$R$_8$)$_n$—$R_9$;

$R_3$ is selected from the group consisting of H, $C_1$-$C_{10}$alkyl, $C_3$-$C_7$cycloalkyl, $C_2$-$C_{10}$alkenyl, $SO_2$—$R_7$, $CH_2CF_3$ or a 4 to 6 membered saturated ring containing an oxygen atom;

$R_4$ is present where Y is C and is selected from the group consisting of H, $C_1$-$C_6$alkyl, $C_1$-$C_6$cycloalkyl, $C_1$-$C_6$alkoxy, CO($R_7$), COO($R_7$), $CF_3$ and halogen, $R_5$ is selected from the group consisting of H, $C_1$-$C_6$alkyl, $COOCH_3$, and $CONHSO_2CH_3$;

$R_6$ is selected from the group consisting of OH, O($C_1$-$C_6$alkyl), $NH_2$, $NHSO_2N(C_1$-$C_6$alkyl)$_2$, $NHSO_2NHCH_3$, $NHSO_2(C_1$-$C_6$alkyl), $NHSO_2(C_3$-$C_7$cycloalkyl), and $N(C_1$-$C_6$-alkyl)$_2$;

$R_7$ and $R_8$ are each independently chosen from H, $C_1$-$C_{10}$alkyl, $C_3$-$C_7$cycloalkyl or $R_7$ and $R_8$ taken together form a 4 to 6 membered aliphatic ring that optionally contains a heteroatom selected from the group N, S, O;

$R_9$ is selected from the group consisting of H, $R_{10}$, $C_1$-$C_6$alkyl, OH, CN, F, $CF_2H$, $CF_3$, $CONR_7R_8$, $COOR_7$, $CON(R_7)SO_2R_8$, $CON(R_7)SO_2N(R_7R_8)$, $NR_7R_8$, $NR_7COOR_8$, $OCOR_7$, O-Benzyl, $NR_7SO_2R_8$, $SO_2NR_7R_8$, $SO_2R_7$, $OCONR_7R_8$, $OCONR_7R_{10}$, $N(R_7)CON(R_7R_8)$, $N(R_7)COOR_{10}$; phtalimido, 2-methyl-benzothiophene(1,1) dioxide, or a 4 to 6 membered saturated ring containing an oxygen atom;

n is an integer from 2 to 6;

$R_{10}$ is selected from the group consisting of $C_1$-$C_6$ alkyl, $C_3$-$C_7$cycloalkyl, phenyl, pyridine or pyrazole, optionally substituted with one or more substituents selected from the group comprising $CF_3$, $CH_3$, $OCH_3$, $OCF_3$ or halogen.

In an embodiment according to the invention, $R_3$ is selected from the group consisting of H, $C_1$-$C_{10}$alkyl, $C_3$-$C_7$cycloalkyl, $C_2$-$C_{10}$alkenyl, $SO_2$—$R_7$, or a 4 to 6 membered saturated ring containing an oxygen atom; and $R_9$ is selected from the group consisting of H, $C_1$-$C_6$alkyl, OH, CN, F, $CF_2H$, $CF_3$, $CONR_7R_8$, $COOR_7$, $CON(R_7)SO_2R_8$, $CON(R_7)SO_2N(R_7R_8)$, $NR_7R_8$, $NR_7COOR_8$, $OCOR_7$, O-Benzyl, $NR_7SO_2R_8$, $SO_2NR_7R_8$, $SO_2R_7$ or a 4 to 6 membered saturated ring containing an oxygen atom;

n is an integer from 2 to 6.

In another aspect, the invention relates to the foregoing compounds for use in the treatment of RSV infections in warm-blooded animals, preferably humans. In yet another aspect, the invention presents a method of treatment of viral RSV infections in a subject in need thereof, comprising administering to said subject an effective amount of a compound as defined above. In still another aspect, the invention resides in the use of a compound as defined above, for the manufacture of a medicament in the treatment of RSV infections.

In a further aspect, the invention relates to a pharmaceutical composition comprising a compound as defined above, and a pharmaceutically acceptable excipient.

In a still further aspect, the invention provides methods for preparing the compounds defined above.

DETAILED DESCRIPTION OF THE INVENTION

The molecules of formula I, in deviation from the prior art, have on one side (the left side in the formula as depicted) a substituted azabenzimidazole moiety. The invention, in a broad sense, is based on the judicious recognition that these substituted azabenzimidazole compounds generally possess an interesting RSV inhibitory activity. Moreover, these compounds enable access to anti-RSV activities at the higher regions (i.e. the lower end of the $EC_{50}$ values) of the range available in the aforementioned references. Particularly, on the basis of these compounds, molecular structures can be uncovered that even outperform the reference compounds in terms of biological activities.

The present invention will further be described with respect to particular embodiments and with reference to certain examples but the invention is not limited thereto but only by the claims. Where the term "comprising" is used in the present description and claims, it does not exclude other elements or steps. Where an indefinite or definite article is used when referring to a singular noun e.g. "a" or "an", "the", this includes a plural of that noun unless something else is specifically stated.

The term 'prodrug' as used throughout this text means the pharmacologically acceptable derivatives, e.g. esters and amides, such that the resulting biotransformation product of the derivative is the active drug as defined in the compounds of formula (I). The reference by Goodman and Gilman (The Pharmacological Basis of Therapeutics, $8^{th}$ ed., a McGraw-Hill, Int. Ed. 1992, "Biotransformation of Drugs", p. 13-15) describing prodrugs generally, is hereby incorporated. Prodrugs are characterized by a good aqueous solubility and bioavailability, and are readily metabolized into the active inhibitors in vivo.

As used herein $C_1$-$C_6$alkyl as a group or part of a group defines straight or branched chain saturated hydrocarbon radicals having from 1 to 6 carbon atoms such as methyl, ethyl, propyl, 1-methylethyl, butyl, pentyl, hexyl, 2-methylbutyl and the like.

$C_1$-$C_{10}$alkyl as a group or part of a group defines straight or branched chain saturated hydrocarbon radicals having from 1 to 10 carbon atoms such as the groups defined for $C_{1-6}$alkyl and heptyl, octyl, nonyl, 2-methylhexyl, 2-methylheptyl, decyl, 2-methylnonyl, and the like. Optionally, $C_{1-10}$alkyl includes a cycloalkyl moiety, preferably a cyclopropyl moiety, e.g. methylcyclopropyl, ethylcyclopropyl, and the like.

The term '$C_2$-$C_{10}$alkenyl' used herein as a group or part of a group is meant to comprise straight or branched chain unsaturated hydrocarbon radicals having at least one double bond, and preferably having one double bond, and from 2 to 10 carbon atoms such as ethenyl, propenyl, buten-1-yl, buten-2-yl, penten-1-yl, penten-2-yl, hexen-1-yl, hexen-2-yl, hexen-3-yl, 2-methylbuten-1-yl, hepten-1-yl, hepten-2-yl, hepten-3-yl, hepten-4-yl, 2-methylhexen-1-yl, octen-1-yl, octen-2-yl, octen-3-yl, octen-4-yl, 2-methylhepten-1-yl, nonen-1-yl, nonen-2-yl, nonen-3-yl, nonen-4-yl, nonen-5-yl, 2-methylocten-1-yl, decen-1-yl, decen-2-yl, decen-3-yl, decen-4-yl, decen-5-yl, 2-methylnonen-1-yl, and the like;

Whenever a $C_2$-$C_{10}$alkenyl group is linked to a heteroatom it preferably is linked via a saturated carbon atom.

$C_1$-$C_6$alkoxy, as a group or part of a group defines an O—$C_1$-$C_6$alkyl radical, wherein $C_1$-$C_6$alkyl has, independently, the meaning given above.

$C_3$-$C_7$cycloalkyl is generic to cyclopropyl, cyclobutyl, cyclopentyl, cyclohexyl or cycloheptyl.

The term —$(CR_7R_8)_n$ used herein defines n repetitions of the $CR_7R_8$ subgroup, wherein each of these subgroups is independently defined.

The term halogen is generic to fluoro, chloro, bromo and iodo.

It should be noted that the radical positions on any molecular moiety used in the definitions may be anywhere on such moiety as long as it is chemically stable.

Radicals used in the definitions of the variables include all possible isomers unless otherwise indicated. For instance pentyl includes 1-pentyl, 2-pentyl and 3-pentyl.

When any variable occurs more than one time in any constituent, each definition is independent.

Whenever used hereinafter, the term "compounds of formula (I)", or "the present compounds" or similar term is meant to include the compounds of general formula (I), their prodrugs, N-oxides, addition salts, quaternary amines, metal complexes and stereochemically isomeric forms.

It will be appreciated that some of the compounds of formula (I) may contain one or more centers of chirality and exist as stereochemically isomeric forms.

The term "stereochemically isomeric forms" as used hereinbefore defines all the possible compounds made up of the same atoms bonded by the same sequence of bonds but having different three-dimensional structures which are not interchangeable, which the compounds of formula (I) may possess.

Unless otherwise mentioned or indicated, the chemical designation of a compound encompasses the mixture of all possible stereochemically isomeric forms which said compound may possess. Said mixture may contain all diastereomers and/or enantiomers of the basic molecular structure of said compound. All stereochemically isomeric forms of the compounds of the present invention both in pure form or in admixture with each other are intended to be embraced within the scope of the present invention.

Pure stereoisomeric forms of the compounds and intermediates as mentioned herein are defined as isomers substantially free of other enantiomeric or diastereomeric forms of the same basic molecular structure of said compounds or intermediates. In particular, the term 'stereoisomerically pure' concerns compounds or intermediates having a stereoisomeric excess of at least 80% (i e minimum 90% of one isomer and maximum 10% of the other possible isomers) up to a stereoisomeric excess of 100% (i.e. 100% of one isomer and none of the other), more in particular, compounds or intermediates having a stereoisomeric excess of 90% up to 100%, even more in particular having a stereoisomeric excess of 94% up to 100% and most in particular having a stereoisomeric excess of 97% up to 100%. The terms 'enantiomerically pure' and 'diastereomerically pure' should be understood in a similar way, but then having regard to the enantiomeric excess, respectively the diastereomeric excess of the mixture in question.

Pure stereoisomeric forms of the compounds and intermediates of this invention may be obtained by the application of art-known procedures. For instance, enantiomers may be separated from each other by the selective crystallization of their diastereomeric salts with optically active acids or bases. Examples thereof are tartaric acid, dibenzoyl-tartaric acid, ditoluoyltartaric acid and camphosulfonic acid. Alternatively, enantiomers may be separated by chromatographic techniques using chiral stationary phases. Said pure stereochemically isomeric forms may also be derived from the corresponding pure stereochemically isomeric forms of the appropriate starting materials, provided that the reaction occurs stereospecifically. Preferably, if a specific stereoisomer is desired, said compound will be synthesized by stereospecific methods of preparation. These methods will advantageously employ enantiomerically pure starting materials.

The diastereomeric racemates of formula (I) can be obtained separately by conventional methods. Appropriate physical separation methods that may advantageously be employed are, for example, selective crystallization and chromatography, e.g. column chromatography.

For some of the compounds of formula (I), their prodrugs, N-oxides, salts, solvates, quaternary amines, or metal complexes and the intermediates used in the preparation thereof, the absolute stereochemical configuration was not experimentally determined A person skilled in the art is able to determine the absolute configuration of such compounds using art-known methods such as, for example, X-ray diffraction.

The present invention is also intended to include all isotopes of atoms occurring on the present compounds. Isotopes include those atoms having the same atomic number but different mass numbers. By way of general example and without limitation, isotopes of hydrogen include tritium and deuterium. Isotopes of carbon include C-13 and C-14.

For therapeutic use, salts of the compounds of formula (I) are those wherein the counterion is pharmaceutically acceptable. However, salts of acids and bases which are non-pharmaceutically acceptable may also find use, for example, in the preparation or purification of a pharmaceutically acceptable compound. All salts, whether pharmaceutically acceptable or not are included within the ambit of the present invention.

The pharmaceutically acceptable acid and base addition salts as mentioned hereinabove are meant to comprise the therapeutically active non-toxic acid and base addition salt forms which the compounds of formula (I) are able to form. The pharmaceutically acceptable acid addition salts can conveniently be obtained by treating the base form with such appropriate acid. Appropriate acids comprise, for example, inorganic acids such as hydrohalic acids, e.g. hydrochloric or hydrobromic acid, sulfuric, nitric, phosphoric and the like acids; or organic acids such as, for example, acetic, propanoic, hydroxyacetic, lactic, pyruvic, oxalic (i.e. ethanedioic), malonic, succinic (i.e. butanedioic acid), maleic, fumaric, malic (i.e. hydroxybutanedioic acid), tartaric, citric, methanesulfonic, ethanesulfonic, benzenesulfonic, p-toluenesulfonic, cyclamic, salicylic, p-aminosalicylic, pamoic and the like acids.

Conversely said salt forms can be converted by treatment with an appropriate base into the free base form.

The compounds of formula (I) containing an acidic proton may also be converted into their non-toxic metal or amine addition salt forms by treatment with appropriate organic and inorganic bases. Appropriate base salt forms comprise, for example, the ammonium salts, the alkali and earth alkaline metal salts, e.g. the lithium, sodium, potassium, magnesium, calcium salts and the like, salts with organic bases, e.g. the benzathine, N-methyl-D-glucamine, hydrabamine salts, and salts with amino acids such as, for example, arginine, lysine and the like.

The term addition salt as used hereinabove also comprises the solvates, which the compounds of formula (I) as well as the salts thereof, are able to form. Such solvates are for example hydrates, alcoholates and the like.

The term "quaternary amine" as used hereinbefore defines the quaternary ammonium salts which the compounds of formula (I) are able to form by reaction between a basic nitrogen of a compound of formula (I) and an appropriate quaternizing agent, such as, for example, an optionally substituted alkylhalide, arylhalide or arylalkylhalide, e.g. methyliodide or benzyliodide. Other reactants with good leaving groups may also be used, such as alkyl trifluoromethanesulfonates, alkyl methanesulfonates, and alkyl p-toluenesulfonates. A quaternary amine has a positively charged nitrogen. Pharmaceutically acceptable counterions include chloro, bromo, iodo, trifluoroacetate and acetate. The counterion of choice can be introduced using ion exchange resins.

The N-oxide forms of the present compounds are meant to comprise the compounds of formula (I) wherein one or several nitrogen atoms are oxidized to the so-called N-oxide.

It will be appreciated that the compounds of formula (I) may have metal binding, chelating, complexating properties and therefore may exist as metal complexes or metal chelates. Such metalated derivatives of the compounds of formula (I) are intended to be included within the scope of the present invention.

Some of the compounds of formula (I) may also exist in their tautomeric form. Such forms although not explicitly indicated in the above formula are intended to be included within the scope of the present invention.

It will be appreciated that the compounds of the invention, with reference to the aforementioned left- and right-hand parts of formula I, present a wide variety of modification.

Without detracting from the overall scope of the invention, certain embodiments are discussed in more detail below.

In a preferred embodiment at most two X are N. In a preferred embodiment, one X is N. In a more preferred embodiment, the one X that is N is located in meta position to the N—$R_2$ group of the imidazole ring, and said N is located in ortho position to the =N-atom of the imidazole ring.

In one preferred embodiment, $R_1$ is selected from the group consisting of H, halogen, and $CH_2$—$NH_2$. In a further preferred embodiment, $R_1$ in the para position to C—N—$R_2$ is selected from the group consisting of H, halogen, and $CH_2$—$NH_2$, and all other $R_1$ are H. In a further preferred embodiment halogen is bromo or chloro. In a most preferred embodiment, at most one $R_1$ is chloro, and all other $R_1$ are H. In yet an even more preferred embodiment, $R_1$ in the para position to C—N—$R_2$ is chloro.

In another preferred embodiment, $R_2$ comprises a —$(CR_7R_8)_n$—$R_9$ chain wherein $R_2$ and $R_8$ are preferably H and n is 2-4. Preferably $R_9$ is selected from the group consisting of OH, $C_1$-$C_6$alkyl, more preferably 2-propyl, $C_1$-$C_6$alkoxy, more preferably methoxy, $SO_2R_7$, with $R_2$ preferably being methyl. Most preferably $R_9$ is fluoro or $CF_3$.

In a preferred embodiment $R_3$ is selected from the group consisting of $C_3$-$C_7$cycloalkyl, more preferably cyclopropyl, and a 4 membered saturated hydrocarbon containing an oxygen atom.

In a preferred embodiment, and more preferably in conjunction with the other preferred embodiments, one Y is N, and the other Y's are C. In a most preferred embodiment, the one Y that is N, is the Y in para position to N—$R_3$.

Preferably at most one $R_4$ is halogen, preferably fluoro. Most preferably, all $R_4$ are H.

Preferred compounds are the compounds listed below. More preferred are compounds number 1, 2, 3, 4, 5, 6, 7, 8, 9, 10, 11, 16, 17, 18, 19, 20, 21, 31, 32, 33, 34, 35, and 36. Most preferred are compounds number 1, 2, 16, 31, 32, and 33.

The compounds of formula I may be prepared by the methods described below, using synthetic methods known in the art of organic chemistry, or modifications and derivatisations that are familiar to those skilled in the art. The starting materials used herein are commercially available or may be prepared by routine methods known in the art such as those methods disclosed in standard reference books. Preferred methods include, but are not limited to, those described below.

During any of the following synthetic sequences it may be necessary and/or desirable to protect sensitive or reactive groups on any of the molecules concerned. This can be achieved by means of conventional protecting groups, such as those described in T. W. Greene and P. G. M. Wuts, Protective Groups in Organic Chemistry, John Wiley & Sons, 1999, which are hereby incorporated by reference.

Compounds of formula I, or their pharmaceutically acceptable salts, can be prepared according to the reaction schemes discussed herein below. Unless otherwise indicated, the substituent in the schemes are defined as above. Isolation and purification of the products is accomplished by standard procedures, which are known to a chemist of ordinary skill.

Scheme 1 illustrates a method for the preparation of compounds of formula I, where $R_1$ to $R_4$, X and Y are defined as above.

Referring to scheme 1, a compound of formula I can be synthesized by coupling 2-hydroxymethylene imidazopyridines II-a with $N^3$-substituted 2-oxo-imidazopyridine or with $N^3$-substituted 2-oxo-imidazobenzene III in a known in the art method such as a Mitsunobu reaction which uses azadiisopropyldicarboxylate and triphenyl phosphine in a suitable solvent such as DMF or THF. Alternatively, compound of formula I may be prepared by displacement of Z, which is a halide, preferably chlorine II-b, or a sulfonate such as mesylate II-c in the presence of a base such as sodium hydride, potassium carbonate or cesium carbonate in a suitable solvent such as DMF or THF.

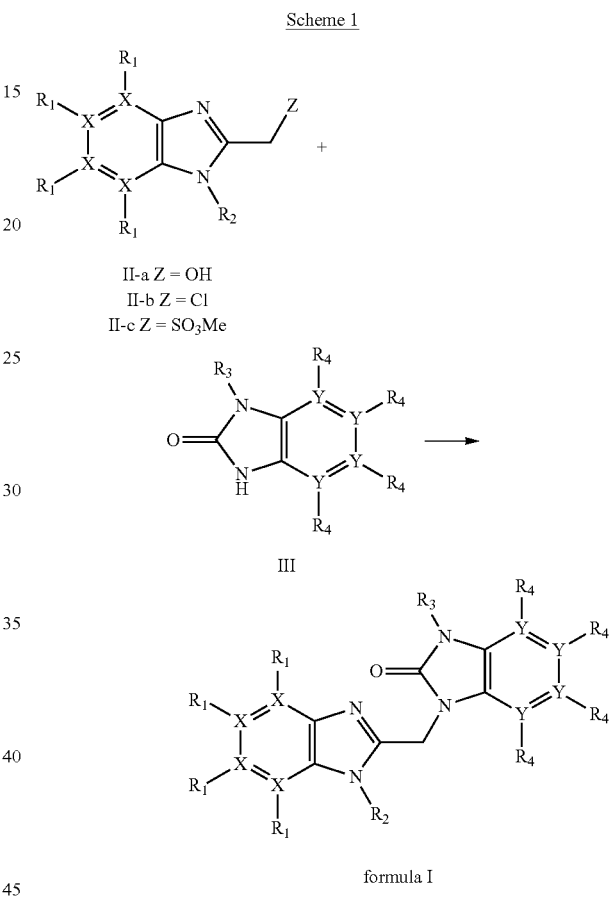

Preparation of Compound II-b and II-c

Treatment of the alcohol II-a with thionyl chloride provides 2-chloromethyl imidazopyridines II-b. Alternatively, alcohol II-a may be transformed to the intermediate II-c by a reaction with methane sulfonyl chloride in the presence of an organic base such as triethyl amine or diisopropyl ethyl amine in a suitable solvent such as dichloromethane (scheme 2).

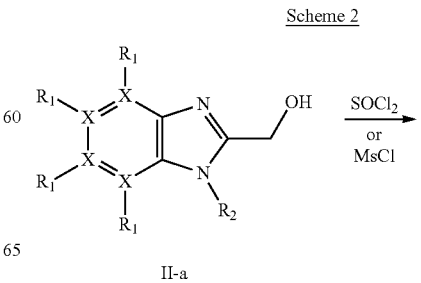

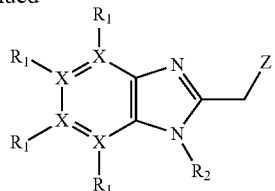

II-b Y = Cl
II-c Y = SO₃Me

Preparation of Compound II-a

Compounds of formula II-a are either commercially available or can be prepared, but not limited to, by general procedures illustrated by scheme 3, wherein $R_1$, $R_2$, X are defined as above. Referring to scheme 3 below, haloheteroaryls IV, where W is an halide preferably fluorine, can be treated with primary amines of formula V in the presence of a suitable base such as potassium carbonate and the like, in a suitable solvent such as ethanol or dichloromethane at a reaction temperature ranging from room temperature to 100° C. to give compounds of formula VI. Hydrogenation of the nitro group using well-precedented conditions such as Pd/C, or other catalyst, under hydrogen or Fe/EtOH/CaCl₂ can yield diamine of formula VII. Alternatively, the hydrogenation of the nitro group of compound VIII using well-precedented conditions such as Pd/C, or other catalyst, under hydrogen or Fe/EtOH/CaCl₂ yield diamine of formula IX which can be treated with the aldehydes of formula X in the presence of suitable reducing agents such as NaBH(OAc)₃, or Na(CN)BH₃ in solvents such as methylene chloride, DMF or THF, at about room temperature gives compounds of formula VII. The imidazol ring can be formed by treating diamines VII with glycolic acid or an ester like XIII under strong acidic conditions, such as aqueous hydrochloric acid, at elevated temperature such as reflux to yield the alcohols of formula II-a. Alternatively, diamines VII can be condensed with dialkoxyacetate of formula XII, in the presence of acetic acid, in a suitable solvent such as methanol gives the acetal II-e. The acetal of compounds II-e can be removed with acids such as hydrochloric acid to give the aldehydes of formula II-f. The resulting aldehydes of formula II-f can be reduced to alcohols using a suitable reducing agent such as NaBH₄ or LiAlH₄ in a suitable solvent such as ethanol or THF to yield the desired alcohols of formula II-a. In addition, diamines VII can be cyclized with dialkyl oxalate of formula XI in a suitable solvent such as ethanol at elevated temperature with or without microwave heating to produce imidazoles of formula II-d. Alternatively, compounds of formula II-d may be prepared in a two steps synthesis starting from diamines VII. Firstly diamine VII may be reacted with an alkyl trihaloacetimidate, preferably methyl 2,2,2-trichloroacetimidate, in an acidic media, preferably acetic acid, at a temperature ranging between 25 and 50° C. to yield compound of formula II-g. Secondly a reaction of compounds of formula II-g with metalcarbonate, preferably sodium carbonate in a suitable solvent such as methanol, lead to compounds of formula II-d. Compounds II-d can be subsequently reduced to the desired alcohols of formula II-a using a suitable reducing agent such as NaBH₄ or LiAlH₄ in a suitable solvent such as ethanol or THF.

Scheme 3

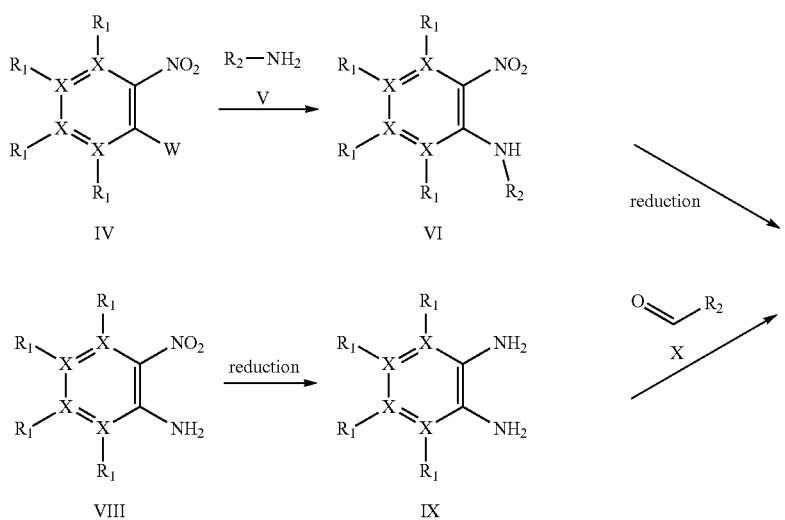

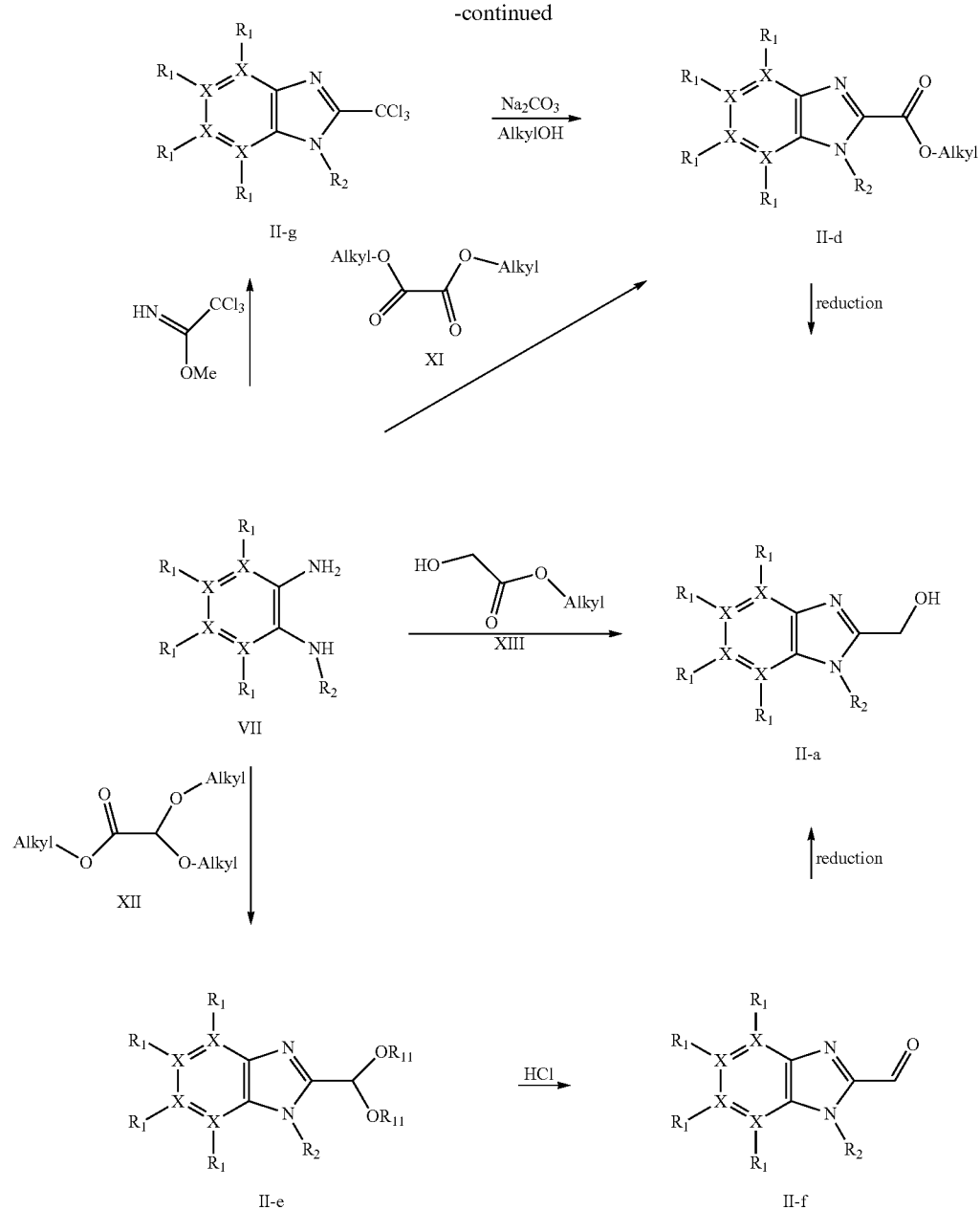

An alternative route for the preparation of compounds of type II-a is depicted in scheme 4. Diamine IX may be first coupled to an alkyl glycolic acid or an ester like XIII under strong acidic conditions, such as aqueous hydrochloric acid, at elevated temperature such as reflux to yield the alcohols of formula XIV. This alcohol may be protected by a PG, where PG is a protecting group such as, but not limiting to, a trityl which consequently results in compounds XV. A suitable solvent for this type of reactions can be, but not limiting to, dichloromethane. The treatment of compound XV with compound XVI, wherein the LG is a leaving group, such as halide, preferably bromine, or sulfonate, in the presence of a base such as sodium hydride, potassium carbonate or cesium carbonate in a suitable solvent such as DMF or THF, gives compound II-h. The removal of the PG in compound II-h may be done in the presence of an acid such as hydrochloric acid in the presence of a solvent, not limited to, such as dioxane to yield compound II-a.

Scheme 4

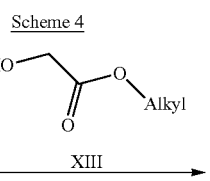

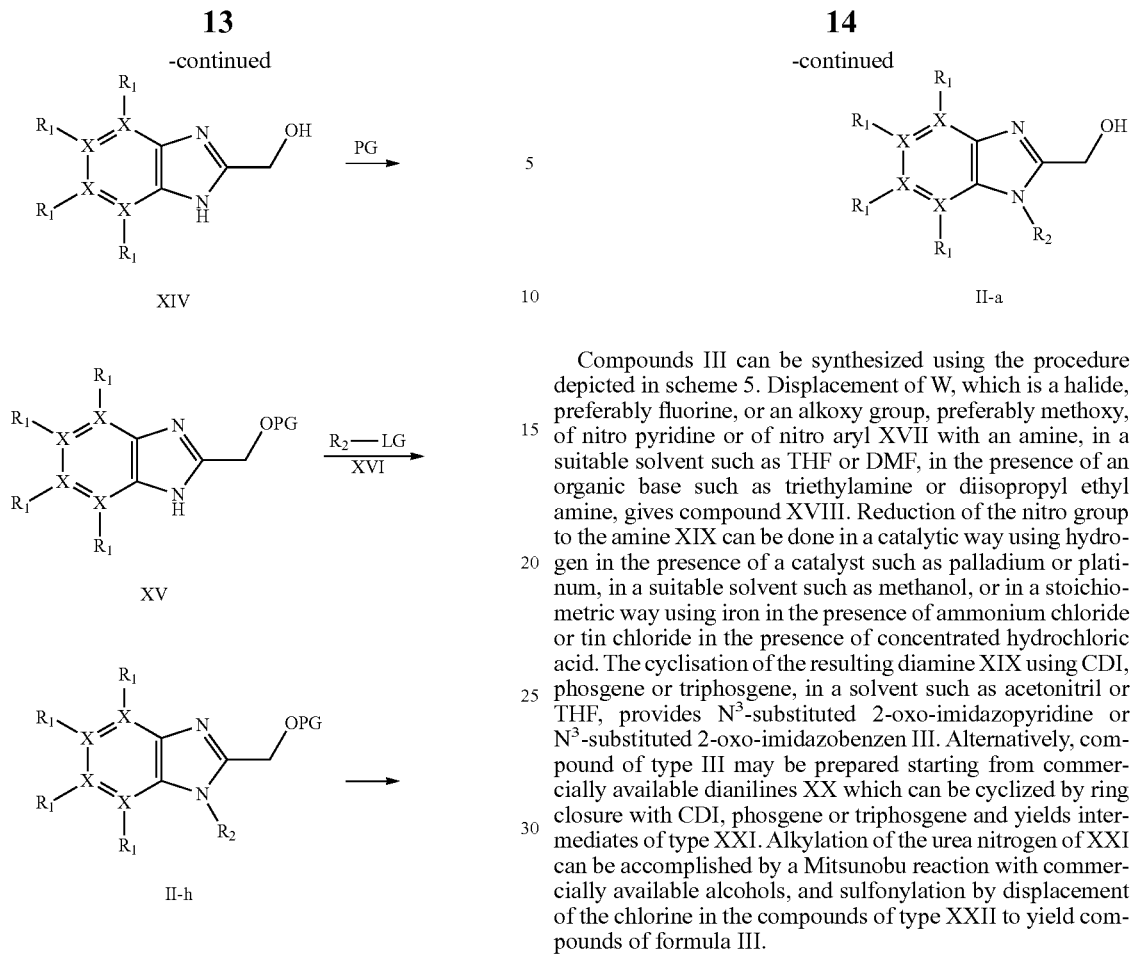

Compounds III can be synthesized using the procedure depicted in scheme 5. Displacement of W, which is a halide, preferably fluorine, or an alkoxy group, preferably methoxy, of nitro pyridine or of nitro aryl XVII with an amine, in a suitable solvent such as THF or DMF, in the presence of an organic base such as triethylamine or diisopropyl ethyl amine, gives compound XVIII. Reduction of the nitro group to the amine XIX can be done in a catalytic way using hydrogen in the presence of a catalyst such as palladium or platinum, in a suitable solvent such as methanol, or in a stoichiometric way using iron in the presence of ammonium chloride or tin chloride in the presence of concentrated hydrochloric acid. The cyclisation of the resulting diamine XIX using CDI, phosgene or triphosgene, in a solvent such as acetonitril or THF, provides $N^3$-substituted 2-oxo-imidazopyridine or $N^3$-substituted 2-oxo-imidazobenzen III. Alternatively, compound of type III may be prepared starting from commercially available dianilines XX which can be cyclized by ring closure with CDI, phosgene or triphosgene and yields intermediates of type XXI. Alkylation of the urea nitrogen of XXI can be accomplished by a Mitsunobu reaction with commercially available alcohols, and sulfonylation by displacement of the chlorine in the compounds of type XXII to yield compounds of formula III.

Scheme 5

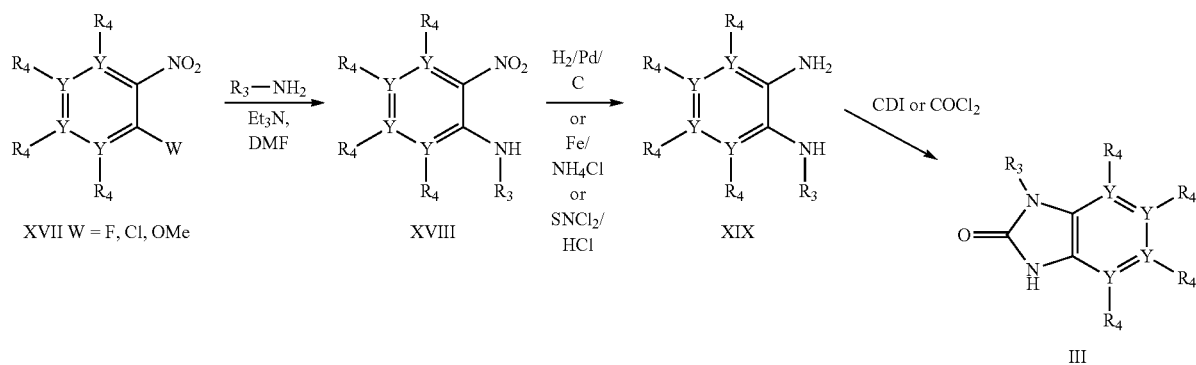

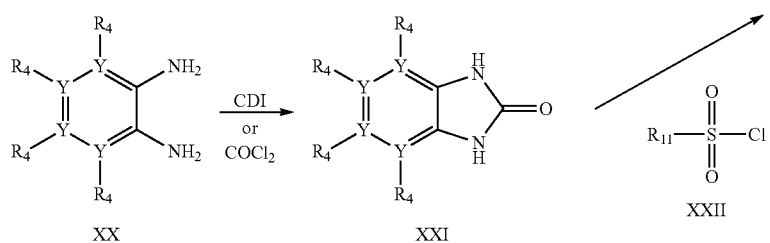

The compounds of formula (I) may be converted to the corresponding N-oxide forms following art-known procedures for converting a trivalent nitrogen into its N-oxide form. Said N-oxidation reaction may generally be carried out by reacting the starting material of formula (I) with an appropriate organic or inorganic peroxide. Appropriate inorganic peroxides comprise, for example, hydrogen peroxide, alkali metal or earth alkaline metal peroxides, e.g. sodium peroxide, potassium peroxide; appropriate organic peroxides may comprise peroxy acids such as, for example, benzenecarboperoxoic acid or halo substituted benzenecarboperoxoic acid, e.g. 3-chlorobenzenecarboperoxoic acid, peroxoalkanoic acids, e.g. peroxoacetic acid, alkylhydroperoxides, e.g. t.butyl hydro-peroxide. Suitable solvents are, for example, water, lower alcohols, e.g. ethanol and the like, hydrocarbons, e.g. toluene, ketones, e.g. 2-butanone, halogenated hydrocarbons, e.g. dichloromethane, and mixtures of such solvents.

Pure stereochemically isomeric forms of the compounds of formula (I) may be obtained by the application of art-known procedures. Diastereomers may be separated by physical methods such as selective crystallization and chromatographic techniques, e.g., counter-current distribution, liquid chromatography and the like.

The compounds of formula (I) as prepared in the hereinabove described processes are generally racemic mixtures of enantiomers which can be separated from one another following art-known resolution procedures. The racemic compounds of formula (I) which are sufficiently basic or acidic may be converted into the corresponding diastereomeric salt forms by reaction with a suitable chiral acid, respectively chiral base. Said diastereomeric salt forms are subsequently separated, for example, by selective or fractional crystallization and the enantiomers are liberated therefrom by alkali or acid. An alternative manner of separating the enantiomeric forms of the compounds of formula (I) involves liquid chromatography, in particular liquid chromatography using a chiral stationary phase. Said pure stereochemically isomeric forms may also be derived from the corresponding pure stereochemically isomeric forms of the appropriate starting materials, provided that the reaction occurs stereospecifically. Preferably if a specific stereoisomer is desired, said compound will be synthesized by stereospecific methods of preparation. These methods will advantageously employ enantiomerically pure starting materials.

In a further aspect, the present invention concerns a pharmaceutical composition comprising a therapeutically effective amount of a compound of formula (I) as specified herein, or a compound of any of the embodiments of compounds of formula (I) as specified herein, and a pharmaceutically acceptable carrier. A therapeutically effective amount in this context is an amount sufficient to prophylaxictically act against, to stabilize or to reduce viral infection, and in particular RSV viral infection, in infected subjects or subjects being at risk of being infected. In still a further aspect, this invention relates to a process of preparing a pharmaceutical composition as specified herein, which comprises intimately mixing a pharmaceutically acceptable carrier with a therapeutically effective amount of a compound of formula (I), as specified herein, or of a compound of any of the embodiments of compounds of formula (I) as specified herein.

Therefore, the compounds of the present invention or any embodiment thereof may be formulated into various pharmaceutical forms for administration purposes. As appropriate compositions there may be cited all compositions usually employed for systemically administering drugs. To prepare the pharmaceutical compositions of this invention, an effective amount of the particular compound, optionally in addition salt form or metal complex, as the active ingredient is combined in intimate admixture with a pharmaceutically acceptable carrier, which carrier may take a wide variety of forms depending on the form of preparation desired for administration. These pharmaceutical compositions are desirable in unitary dosage form suitable, particularly, for administration orally, rectally, percutaneously, or by parenteral injection. For example, in preparing the compositions in oral dosage form, any of the usual pharmaceutical media may be employed such as, for example, water, glycols, oils, alcohols and the like in the case of oral liquid preparations such as suspensions, syrups, elixirs, emulsions and solutions; or solid carriers such as starches, sugars, kaolin, lubricants, binders, disintegrating agents and the like in the case of powders, pills, capsules, and tablets. Because of their ease in administration, tablets and capsules represent the most advantageous oral dosage unit forms, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. Also included are solid form preparations which are intended to be converted, shortly before use, to liquid form preparations. In the compositions suitable for percutaneous administration, the carrier optionally comprises a penetration enhancing agent and/or a suitable wetting agent, optionally combined with suitable additives of any nature in minor proportions, which additives do not introduce a significant deleterious effect on the skin.

The compounds of the present invention may also be administered via oral inhalation or insufflation by means of methods and formulations employed in the art for administration via this way. Thus, in general the compounds of the present invention may be administered to the lungs in the form of a solution, a suspension or a dry powder, a solution being preferred. Any system developed for the delivery of solutions, suspensions or dry powders via oral inhalation or insufflation are suitable for the administration of the present compounds.

Thus, the present invention also provides a pharmaceutical composition adapted for administration by inhalation or insufflation through the mouth comprising a compound of formula (I) and a pharmaceutically acceptable carrier. Preferably, the compounds of the present invention are administered via inhalation of a solution in nebulized or aerosolized doses.

It is especially advantageous to formulate the aforementioned pharmaceutical compositions in unit dosage form for ease of administration and uniformity of dosage. Unit dosage form as used herein refers to physically discrete units suitable as unitary dosages, each unit containing a predetermined quantity of active ingredient calculated to produce the desired therapeutic effect in association with the required pharmaceutical carrier. Examples of such unit dosage forms are tablets (including scored or coated tablets), capsules, pills, suppositories, powder packets, wafers, injectable solutions or suspensions and the like, and segregated multiples thereof.

The compounds of formula (I) show antiviral properties. Viral infections treatable using the compounds and methods of the present invention include those infections brought on by ortho- and paramyxoviruses and in particular by human and bovine respiratory syncytial virus (RSV). A number of the compounds of this invention moreover are active against mutated strains of RSV. Additionally, many of the compounds of this invention show a favorable pharmacokinetic profile and have attractive properties in terms of bioavailabilty, including an acceptable half-life, AUC and peak values and lacking unfavourable phenomena such as insufficient quick onset and tissue retention.

The in vitro antiviral activity against RSV of the present compounds was tested in a test as described in the experimental part of the description, and may also be demonstrated in a virus yield reduction assay. The in vivo antiviral activity against RSV of the present compounds may be demonstrated in a test model using cotton rats as described in Wyde et al. (Antiviral Research (1998), 38, 31-42).

Due to their antiviral properties, particularly their anti-RSV properties, the compounds of formula (I) or any embodiment thereof, their prodrugs, N-oxides, addition salts, quaternary amines, metal complexes and stereochemically isomeric forms, are useful in the treatment of individuals experiencing a viral infection, particularly a RSV infection, and for the prophylaxis of these infections. In general, the compounds of the present invention may be useful in the treatment of warm-blooded animals infected with viruses, in particular the respiratory syncytial virus.

The compounds of the present invention or any embodiment thereof may therefore be used as medicines. Said use as a medicine or method of treatment comprises the systemic administration to viral infected subjects or to subjects susceptible to viral infections of an amount effective to combat the conditions associated with the viral infection, in particular the RSV infection.

The present invention also relates to the use of the present compounds or any embodiment thereof in the manufacture of a medicament for the treatment or the prevention of viral infections, particularly RSV infection.

The present invention furthermore relates to a method of treating a warm-blooded animal infected by a virus, or being at risk of infection by a virus, in particular by RSV, said method comprising the administration of an anti-virally effective amount of a compound of formula (I), as specified herein, or of a compound of any of the embodiments of compounds of formula (I), as specified herein.

In general it is contemplated that an antivirally effective daily amount would be from 0.01 mg/kg to 500 mg/kg body weight, more preferably from 0.1 mg/kg to 50 mg/kg body weight. It may be appropriate to administer the required dose as two, three, four or more sub-doses at appropriate intervals throughout the day. Said sub-doses may be formulated as unit dosage forms, for example, containing 1 to 1000 mg, and in particular 5 to 200 mg of active ingredient per unit dosage form.

The exact dosage and frequency of administration depends on the particular compound of formula (I) used, the particular condition being treated, the severity of the condition being treated, the age, weight, sex, extent of disorder and general physical condition of the particular patient as well as other medication the individual may be taking, as is well known to those skilled in the art. Furthermore, it is evident that said effective daily amount may be lowered or increased depending on the response of the treated subject and/or depending on the evaluation of the physician prescribing the compounds of the instant invention. The effective daily amount ranges mentioned hereinabove are therefore only guidelines.

Also, the combination of another antiviral agent and a compound of formula (I) can be used as a medicine. Thus, the present invention also relates to a product containing (a) a compound of formula (I), and (b) another antiviral compound, as a combined preparation for simultaneous, separate or sequential use in antiviral treatment. The different drugs may be combined in a single preparation together with pharmaceutically acceptable carriers. For instance, the compounds of the present invention may be combined with interferon-beta or tumor necrosis factor-alpha in order to treat or prevent RSV infections.

The invention will hereinafter be illustrated with reference to the following, non-limiting examples.

EXAMPLE 1

Synthesis of Intermediates

All the intermediates needed for the synthesis of targeted compounds of formula I are synthesized as described in the following schemes 6 to 14.

Scheme 6: synthesis of 3-(methylsulfonyl)propan-1-amine hydrochloride 6-e

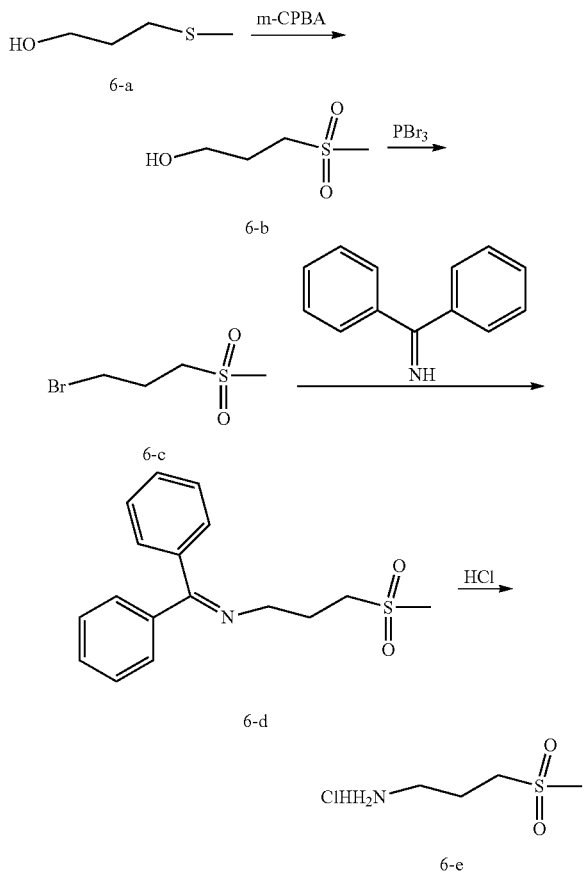

Step 1: Synthesis of 3-(methylsulfonyl)propan-1-ol 6-b

The 3-(methylthio)propan-1-ol 6-a (200 g, 1900 mmol, CAS 505-10-2) was dissolved in $CH_2Cl_2$ (2000 mL). The mixture was cooled to 0° C. The m-CPBA 85% in water (970 g, 5700 mmol, CAS 937-14-4) was added portion wise keeping the temperature between 0 and 5° C. After addition, the mixture was allowed to warm to 25° C. and stirred for 15 h. The mixture was filtered through a celite pad. The filtrate was purified by flash column (Eluent: petroleum ether:ethyl acetate=3:1 and then ethyl acetate:methanol=10:1) to yield the intermediate 6-b (75 g, 29%).

Step 2: Synthesis of 1-bromo-3-(methylsulfonyl)propane 6-c

The intermediate 6-b (75 g, 543 mmol) was dissolved in CH$_2$Cl$_2$ (750 mL). The mixture was cooled to 0° C. The phosphorus tribromide (53.6 mL, 570 mmol) was added dropwise keeping the temperature between 0 and 5° C. After addition, the mixture was allowed to warm to 25° C. and stirred for 15 h. The mixture was poured into ice-water. The separated organic layer was washed with brine (2×500 mL), dried over Na$_2$SO$_4$, filtered and evaporated under vacuum to yield the title compound 6-c (77 g, 71%). $^1$H NMR (400 MHz, CHLOROFORM-d) δ ppm 2.25-2.40 (m, 2 H) 2.91 (s, 3 H) 3.1-3.2 (m, 2H) 3.5-3.6 (m, 2H).

Step 3: Synthesis of N-(diphenylmethylene)-3-(methylsulfonyl)propan-amines 6-d The intermediate 6-c (27 g, 134 mmol) was dissolved in CH$_3$CN (60 mL). Diphenylmethanimine (27 g, 148 mmol) and DIEA (19.6 g, 152 mmol) was added. The mixture was refluxed for 4 h and then cooled to room temperature. The mixture was neutralized with 50% aqueous acetic acid at 25° C. Water (80 mL) was added. The mixture was extracted with ethyl acetate (2×300 mL). The combined organic layers were washed with brine, dried over Na$_2$SO$_4$, filtered and evaporated under vacuum. The residue was washed with petroleum ether (4×100 mL). The mixture was treated with methyl tert-butyl ether. The solid was collected and washed with petroleum ether. The filtrate was dried under vacuum. The residue was purified by column chromatography (Eluent: CH$_2$Cl$_2$:ethyl acetate from 1:0 to 10:1). The title compound 6-d was obtained as a white solid (34 g, 85%).

Step 4: Synthesis of 3-(methylsulfonyl)propan-1-amine hydrochloride 6-e

The intermediate 6-d (34 g, 113 mmol) was dissolved in dioxane (600 mL). The mixture was cooled to 0-5° C. and a solution of 4N HCl/dioxane (120 mL, 480 mmol) was added dropwise. After addition, the mixture was allowed to warm to 25° C. and stirred for 15 h. The mixture was filtered. The solid was collected and washed with dioxane. The title product 6-e was obtained as a yellow powder (11.5 g, 50%).

Scheme 7: synthesis of tert-butyl(4-chlorobutoxy)dimethylsilane 7-b

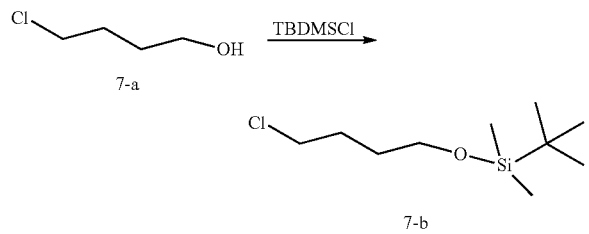

4-Chlorobutan-1-ol 7-a (100 g, 920 mmol, CAS 928-51-8) was dissolved in CH$_2$Cl$_2$ (1000 mL) at room temperature. The mixture was cooled to 0° C. then Imidazole (81.5, 1200 mmol) and TBDMS-Cl (152 g, 1010 mmol) were added. The resulting mixture was stirred for 4 hours at room temperature then filtered off. The filtrate was washed successively with an aqueous solution 10% of HCl and with brine. The resulting solution was dried over MgSO$_4$, filtered then concentrated to yield the title compounds 7-b as a colorless oil (100 g, 50%).

Scheme 8: synthesis of 4-(tert-butyldiphenylsilyloxy)butan-1-amine 8-b

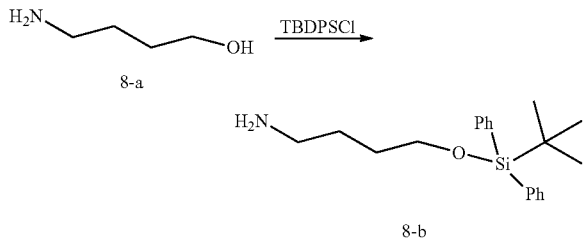

A mixture of 4-aminobutan-1-ol 8-a (50 g, 561 mmol, CAS 13325-10-5), imidazole (167 g, 2450 mmol), and tert-butylchlorodiphenylsilane (170 g, 618 mmol, CAS 58479-61-1) in CH$_2$Cl$_2$ (1500 mL) was stirred at 25° C. for 15 hours. The resulting mixture was washed successively with saturated NaHCO$_3$ (2×800 mL), water (2×800 mL) and brine (2×500 mL). The organic layer was separated, dried over Na$_2$SO$_4$, filtered and evaporated under vacuum. The product 8-b was obtained as an oil (200 g, 95%).

Scheme 9: synthesis of 1-bromo-4-(methylsulfonyl)butane 9-c

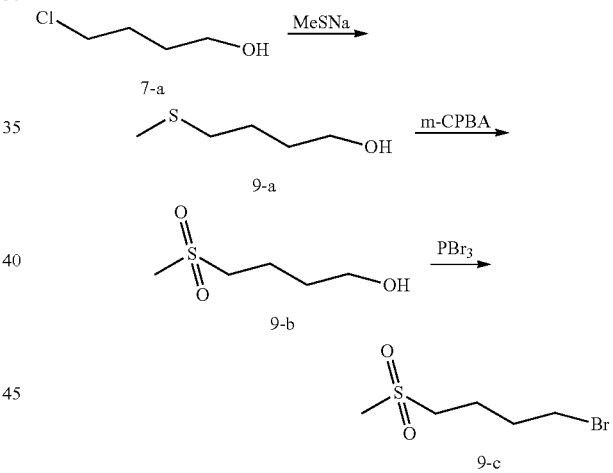

Step 1: Synthesis of 4-(methylthio)butan-1-ol 9-a

4-Chlorobutan-1-ol 7-a (180 g, 1658 mmol, CAS 928-51-8) was added to sodium thiomethoxide (656 g, 1965 mmol, 21% solution in water) at 0-5° C. After addition, the mixture was allowed to warm to 25° C. and stirred for 48 h. The mixture was extracted with CHCl$_3$. The separated organic layer was dried over Na$_2$CO$_3$, filtered and evaporated under vacuum. The residue was distilled to afford the alcohol 9-a as an oil (144.2 g, 72%).

Step 2: Synthesis of 4-(methylsulfonyl)butan-1-ol 9-b

The intermediate 9-a (141 g, 1173 mmol) was dissolved in CH$_2$Cl$_2$ (9000 mL). The mixture was cooled to 0-5° C. m-CPBA (483 g, 85% purity, 2375 mmol, CAS 937-14-4)

was added portion wise at 0-5° C. After addition, the mixture was allowed to warm to 25° C. and stirred for 15 hours. The mixture was filtered through a celite pad. The filtrate was purified by flash column (Eluent: petroleum ether:ethyl acetate=3:1 and then ethyl acetate:methanol=10:1). This yielded product 9-b (98 g, 65%).

Step 3: Synthesis of 1-bromo-4-(methylsulfonyl)butane 9-c

The intermediate 9-b (98 g, 645 mmol) was dissolved in CH$_2$Cl$_2$ (1100 mL). The mixture was cooled to 0-5° C. PBr$_3$ (64 mL, 674 mmol) was added dropwise at 0-5° C. After addition, the mixture was allowed to warm to 25° C. and stirred for 15 hours. The mixture was poured into ice-water. The separated organic layer was washed with brine (2×500 mL), dried over Na$_2$SO$_4$, filtered and evaporated under vacuum. The product 9-c was obtained (84.5 g, 80%).

Scheme 10: synthesis of 1-cyclopropyl-1H-imidazo[4,5-c]pyridine-2(3H)-one 10-d

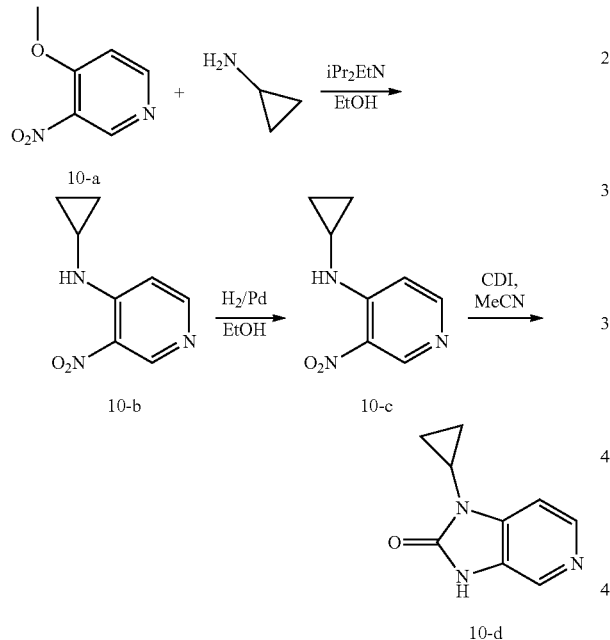

Step 1: Synthesis of N-cyclopropyl-3-nitropyridin-4-amine 10-b

The mixture of 4-methoxy-3-nitropyridine 10-a (200 g, 1300 mmol, CAS 31872-62-5), cyclopropylamine (185.5 g, 3250 mmol) and diisopropyl ethyl amine (336 g, 2600 mmol) in dry ethanol (800 mL) was refluxed for 3 hours. The mixture was cooled to 0° C. The solid was collected by filtration. The filter cake was washed with cold ethanol (150 mL). The solid was dried to afford the title compound 10-b as a white powder (167 g, 72%).

Step 2: Synthesis of N$^4$-cyclopropylpyridin-3,4-diamine 10-c

Intermediate 10-b (167 g, 932 mmol) in ethanol (1400 mL) was hydrogenated (50 Psi) at 20° C. with wet 10% Pd/C (34 g) as a catalyst overnight. After uptake of H$_2$ (3 eq), the catalyst was filtered off and the filtrate was evaporated. The residue was washed with methyl tert-butyl ether to afford the title compound 10-c as a yellow powder (133 g, 95%).

Step 3: Synthesis of 1-cyclopropyl-1H-imidazo[4,5-c]pyridine-2(3H)-one 10-d

Carbonyldiimidazole (151.8 g, 936 mmol) was added to a solution of intermediate 10-c (133 g, 891.4 mmol) in CH$_3$CN (1800 mL) at 0° C. The reaction mixture was allowed to warm to 10° C. and stirred for 1 h. The solid was collected by filtration and was washed with CH$_3$CN (200 mL) to afford the title compound 10-d as a white powder (101 g, 65%).

Scheme 11: Synthesis of 1-(oxetan-3-yl)-1H-imidazo[4,5-c]pyridine-2(3H)-one 11-d

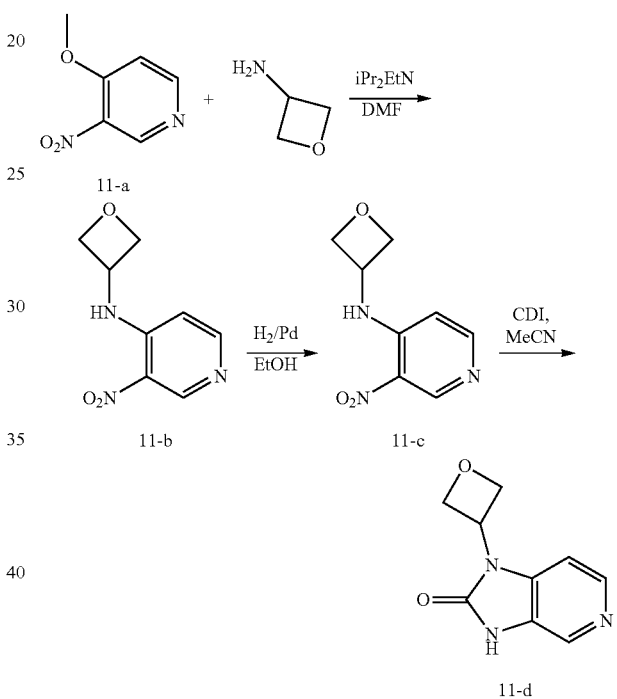

Compound 11-d was prepared in the same manner as compound 10-d using 3-aminooxetane as starting material.

Scheme 12: synthesis of 1-cyclopropyl-5-fluoro-1H-benzo[d]imidazol-2(3H)-one 12-d

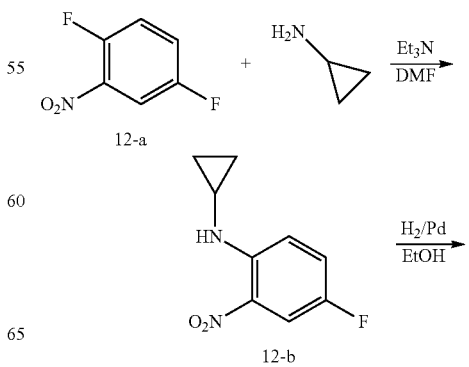

-continued

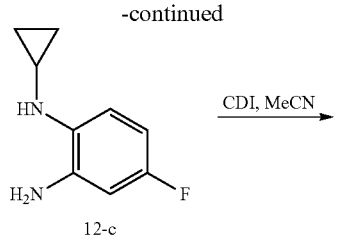

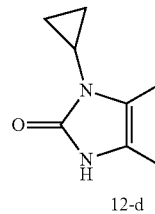

Step 1: Synthesis of N-cyclopropyl-4-fluoro-2-nitroaniline 12-b

The 1,4-difluoro-2-nitrobenzene 12-a (CAS 364-74-9) (15 g, 94.3 mmol) was dissolved in DMF (500 mL). Cyclopropyl amine (7 mL, 100 mmol) was added followed by triethylamine (30 mL, 217 mmol). The resulting mixture was stirred at room temperature overnight. The mixture was poured in water and extracted with dichloromethane dried over $MgSO_4$ and concentrated. The orange solid was purified by column chromatography using dichloromethane and methanol to yield the intermediate 12-b as an orange solid (16 g, 86%).

m/z=197 $(M+H)^+$. $^1$H NMR (400 MHz, CHLOROFORM-d) δ ppm 0.63-0.68 (m, 2 H), 0.88-0.95 (m, 2 H), 2.54-2.55 (m, 1 H), 7.27-7.34 (m, 2 H), 7.84-7.90 (m, 1 H), 7.93-8.02 (m, 1 H).

Step 2: Synthesis of $N^1$-cyclopropyl-4-fluorobenzene-1,2-diamine 12-c

Intermediate 12-b (16 g, 82 mmol) in ethanol (200 mL) was hydrogenated at room temperature with wet 10% Pd/C as a catalyst overnight. After uptake of $H_2$ (3 eq), the catalyst was filtered off and the filtrate was evaporated. The residue was washed with ethanol to afford the title compound 9-c as a white solid (12.8 g, 94%). m/z=167 $(M+H)^+$.

Step 3: Synthesis of 1-cyclopropyl-5-fluoro-1H-benzo[d]imidazol-2(3H)-one 12-d Carbonyldiimidazole (13.15 g, 81 mmol) was added to a solution of intermediate 12-c (12.8 g, 77.3 mmol) in $CH_3CN$ (150 mL) at 0° C. The reaction was allowed to warm up to room temperature and stirred for 4 hours. The solvent was removed, then the residue was purified by column chromatography using $CH_2Cl_2$/methanol to yield a light brown solid which was triturated in diethyl ether to yield compound 12-d as a white solid (7.4 g, 50%). m/z=193 $(M+H)^+$.

$^1$H NMR (400 MHz, CHLOROFORM-d) δ ppm 0.99-1.08 (m, 2 H) 1.08-1.20 (m, 2 H) 2.89 (m, 1 H) 6.75-6.84 (m, 1 H) 6.87 (dd, J=8.53, 2.51 Hz, 1 H) 7.10 (dd, J=8.53, 4.27 Hz, 1 H) 10.33 (br. s., 1 H).

Scheme 13: synthesis of 1-cyclopropyl-1H-benzo[d]imidazol-2(3H)-one 13-d

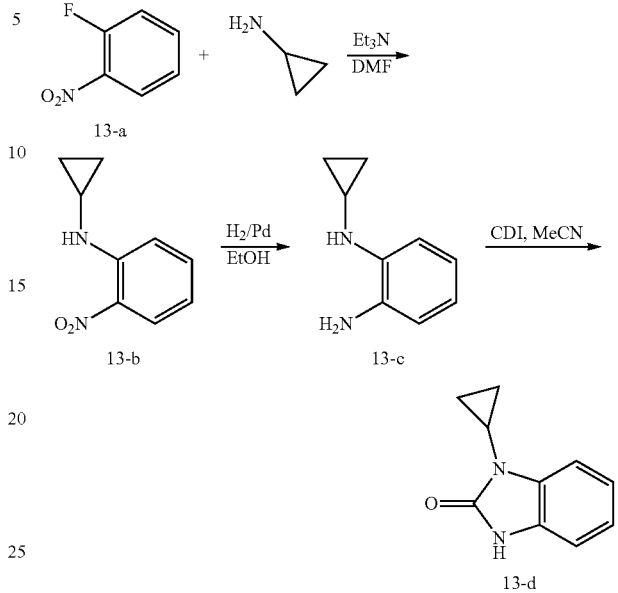

Compound 13-d was prepared in the same manner as compound 12-d using 2-fluoronitrobenzene 13-a as starting material.

Scheme 14: synthesis of 4-chloro-1-isopropyl-1H-imidazo[4,5-c]pyridin-2(3H)-one 13-d

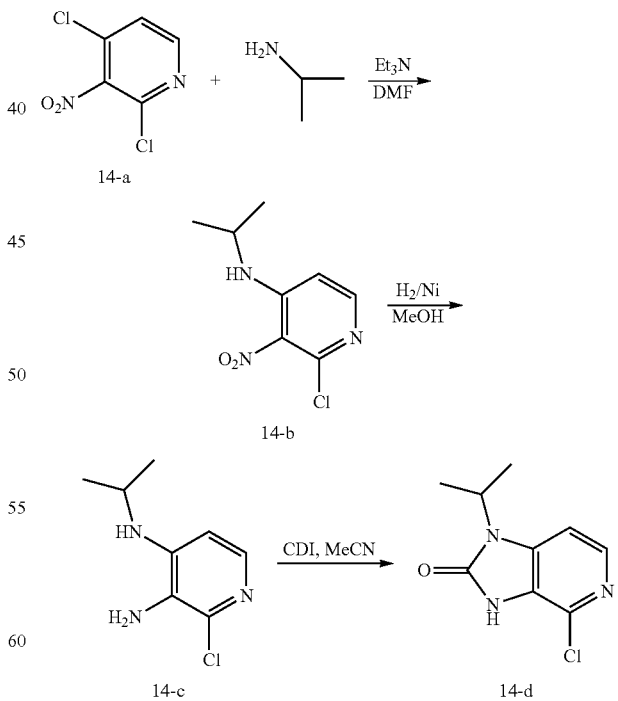

Compound 14-d was prepared in the same manner as compound 12-d using 2,4-dichloro-3-nitropyridine 14-a and isopropyl amine as starting materials.

EXAMPLE 2

Synthesis of 3-((5-chloro-1-isopentyl-1H-imidazo[4,5-b]pyridin-2-yl)methyl)-1-cyclopropyl-1H-imidazo[4,5-c]pyridin-2(3H)-one 1

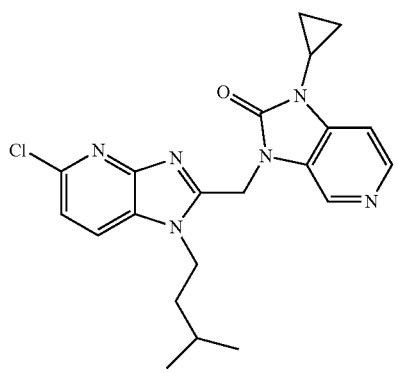

Step 1: Synthesis of 6-chloropyridine-2,3-diamine 1-1

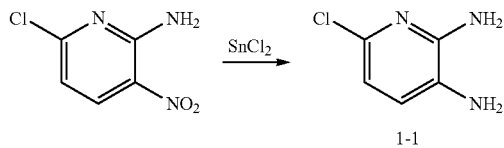

To a mixture of ethyl acetate (450 mL) and tert-butanol (50 mL), 6-chloro-3-nitropyridin-2-amine (CAS 27048-04-0) (15 g, 86,42 mmol), stannous chloride dehydrate (CAS 10025-69-1) (97.5 g, 432.1 mmol) were added. The resulting mixture was stirred at 60° C. for 1 hour. Sodiumborohydride (1.63 g, 43.21 mmol) was added and the mixture was stirred further at 60° C. for another 3 h. The mixture was cooled and stripped from the EtOAc on the rotavapor. The resulting residu was diluted with water (350 mL) and neutralized to pH=9-10 by addition of an aqueous solution of potassium carbonate. The resulting mixture was extracted with EtOAc (3×250 mL), dried over $Na_2SO_4$ and evaporated. The residu was stirred for 72 hours in a mixture of EtOAc/heptane 1/1. The precipitate was filtered and dried in vacuum for 2 hours. The intermediate 1-1 was collected as a greenish powder (9.32 g, 75%). m/z=144 $(M+H)^+$.

Step 2: Synthesis of 6-chloro-$N^3$-isopentylpyridine-2,3-diamine 1-2

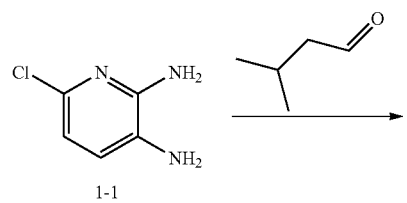

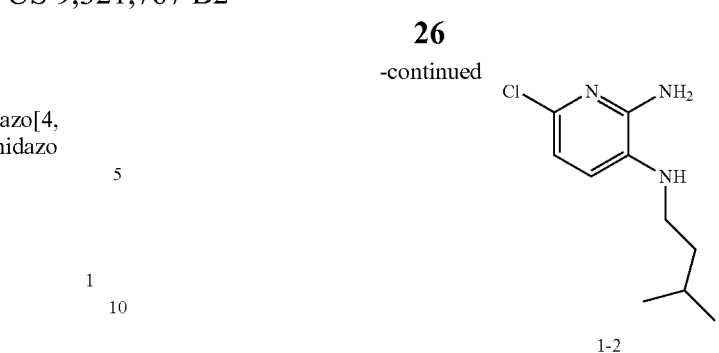

The intermediate 1-1 (5 g, 34.82 mmol) was dissolved in dichloromethane (200 mL), acetic acid (20 drops) and 4-methylpentanal (3 g, 34.8 mmol, CAS 1119-16-0) were added. The resulting mixture was stirred for 30 minutes and then sodium triacetoxyhydroborate (22.14 g, 104.5 mmol) was added. The reaction mixture was stirred at room temperature overnight and a solution of 50% $Na_2CO_3$ was added dropwise until gas evolution stopped. The organic layer was separated, dried on $MgSO_4$, filtrated and evaporated to dryness. The residu was purified by column chromatography using heptane/EtOAc 7/3 to pure EtOAc. Compound 1-2 was recovered as a white solid and dried in vacuo overnight (4.8 g, 65%). m/z=214 $(M+H)^+$.

Step 3: Synthesis of (5-chloro-1-isopentyl-1H-imidazo[4,5-b]pyridin-2-yl)methanol 1-3

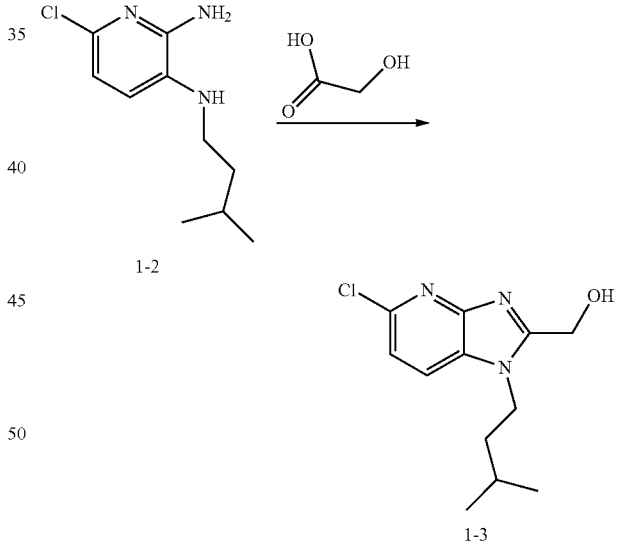

A mixture of intermediate 1-2 (4.8 g, 22.46 mmol) and 2-hydroxyacetic acid (4.27 g, 56.2 mmol) was stirred at 150° C. for 4 hours. The mixture was allowed to cool down to room temperature and treated carefully with 3N hydrochloric acid. The resulting mixture was made basic with aqueous ammonia and extracted with $CH_2Cl_2$ (300 mL). The organic layer was dried over $MgSO_4$ and evaporated to dryness. The residu was purified by column chromatography on silica using $CH_2Cl_2$ to EtOAc. The product 1-3 was isolated as brown solid (3.5 g, 61%).

m/z=255 $(M+H)^+$.

Step 4: Synthesis of 3-((5-chloro-1-isopentyl-1H-imidazo[4,5-b]pyridin-2-yl)methyl)-1-cyclopropyl-1H-imidazo[4,5-c]pyridin-2(3H)-one 1

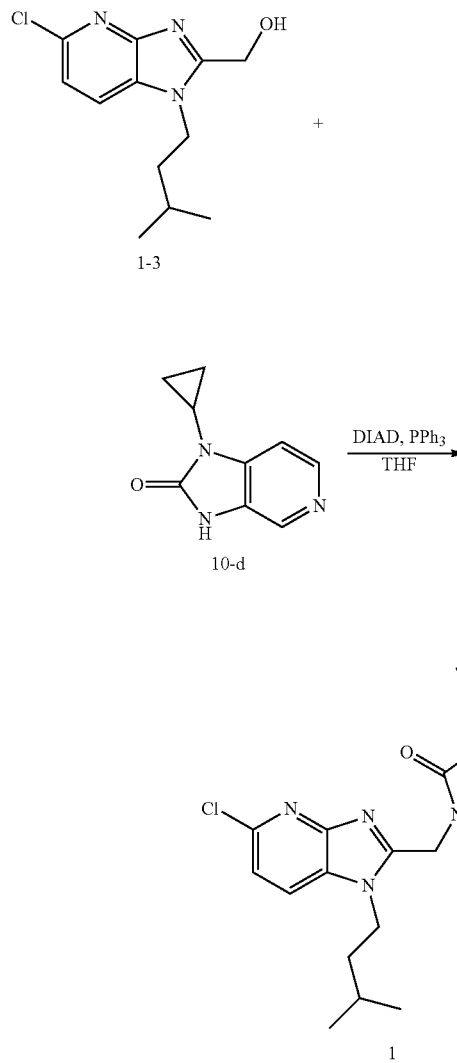

To a stirred solution of intermediate 1-3 (0.29 g, 1.14 mmol), triphenyl phosphine (0.33 g, 1.25 mmol) and the pyridobenzimidazolone 10-d (0.22 g, 1.25 mmol) in dry THF (30 mL) was added DIAD (94%, 0.287 mL, 1.37 mmol) dropwise at room temperature. The reaction mixture was stirred overnight. After completion of the reaction, the mixture was concentrated to dryness the residue was purified by column chromatography eluted with ethyl acetate/CH$_2$Cl$_2$ then CH$_2$Cl$_2$/methanol to yield the title compound 1 as a white solid (233 mg, 50%). m/z=412 (M+H)$^+$.

$^1$H NMR (400 MHz, CHLOROFORM-d) δ ppm 0.95-1.06 (m, 2 H), 0.99 (d, J=6.5 Hz, 6 H), 1.17 (m, 2 H), 1.52 (m, 1 H), 1.64-1.76 (m, 2 H), 2.85-2.96 (m, 1 H), 4.30-4.41 (m, 2 H), 5.37 (s, 2 H), 7.13 (d, J=5.3 Hz, 1 H), 7.23 (d, J=8.5 Hz, 1 H), 7.60 (d, J=8.5 Hz, 1 H), 8.35 (d, J=5.3 Hz, 1 H), 8.69 (s, 1 H)

EXAMPLE 3

Synthesis of 3-((5-chloro-1-isopentyl-1H-imidazo[4,5-b]pyridin-2-yl)methyl)-1-(oxetan-3-yl)-1H-imidazo[4,5-c]pyridin-2(3H)-one 2

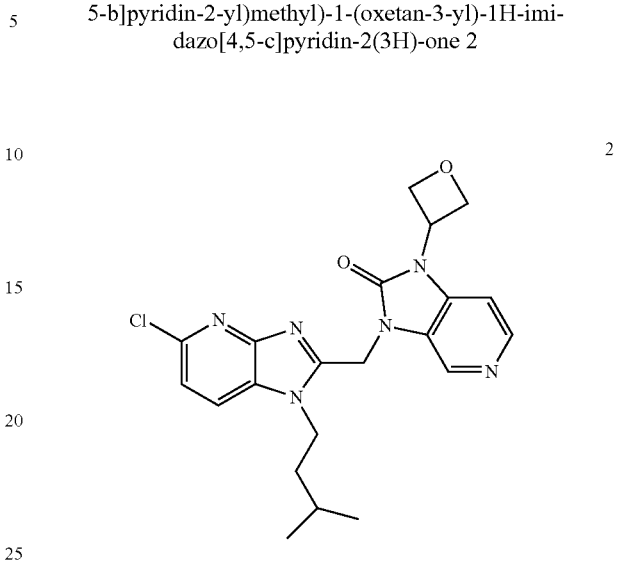

Compound 2 was synthesized in the same manner as compound 1 using intermediates 1-3 and 11-d as starting material. m/z=428 (M+H)$^+$.

$^1$H NMR (400 MHz, CHLOROFORM-d) δ ppm 0.99 (d, J=6.8 Hz, 6 H), 1.51-1.61 (m, 2 H), 1.70 (m, 1 H), 4.29-4.41 (m, 2 H), 5.07-5.18 (m, 4 H), 5.40 (s, 2 H), 5.56-5.67 (m, 1 H), 7.20 (d, J=8.3 Hz, 1 H), 7.58 (dd, J=5.4, 0.6 Hz, 1 H), 7.60 (d, J=8.3 Hz, 1 H), 8.41 (d, J=5.3 Hz, 1 H), 8.75 (s, 1 H)

EXAMPLE 4

Synthesis of 3-((5-chloro-1-isopentyl-1H-imidazo[4,5-b]pyridin-2-yl)methyl)-1-cyclopropyl-5-fluoro-1H-benzo[d]imidazol-2(3H)-one 6

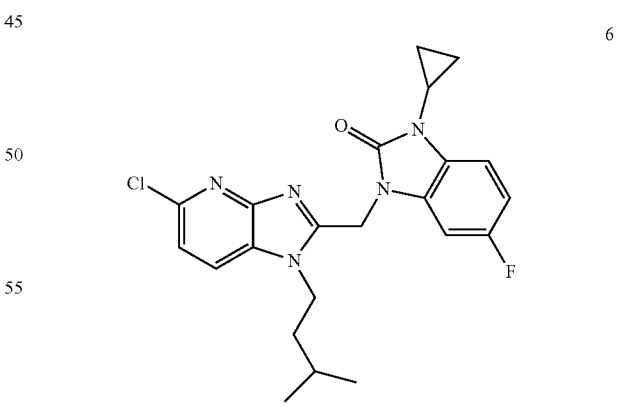

Compound 6 was synthesized in the same manner as compound 1 using intermediates 1-3 and 12-d as starting material. m/z=429 (M+H)$^+$.

$^1$H NMR (400 MHz, CHLOROFORM-d) δ ppm 0.95-1.03 (m, 2 H), 0.98 (d, J=6.5 Hz, 6 H), 1.09-1.17 (m, 2 H), 1.45-1.54 (m, 2 H), 1.65-1.69 (m, 1 H), 2.84-2.89 (m, 1H), 4.34-

4.42 (m, 2 H), 5.32 (s, 2 H), 6.78 (ddd, J=9.5, 8.7, 2.4 Hz, 1 H), 7.07 (dd, J=8.7, 4.4 Hz, 1 H), 7.22 (d, J=8.3 Hz, 1 H), 7.31 (dd, J=8.4, 2.4 Hz, 1 H), 7.59 (d, J=8.5 Hz, 1 H)

EXAMPLE 5

Synthesis of 3-((5-chloro-1-isopentyl-1H-imidazo[4,5-b]pyridin-2-yl)methyl)-3-cyclopropyl-1H-benzo[d]imidazol-2(3H)-one 13

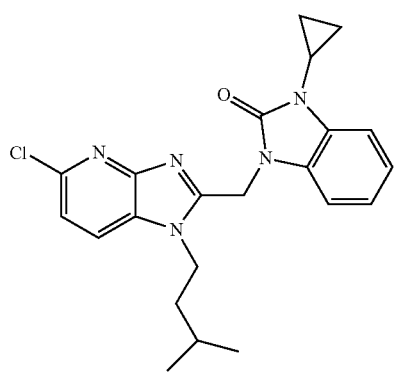

Compound 13 was synthesized in the same manner as compound 1 using intermediates 1-3 and 13-d as starting material. m/z=411 (M+H)$^+$.

$^1$H NMR (400 MHz, CHLOROFORM-d) δ ppm 0.97 (d, J=6.8 Hz, 6 H), 0.99-1.05 (m, 2 H), 1.10-1.17 (m, 2 H), 1.41-1.51 (m, 2 H), 1.63-1.73 (m, 1 H), 2.84-2.92 (m, 1 H), 4.32-4.41 (m, 2 H), 5.37 (s, 2 H), 7.01-7.12 (m, 2 H), 7.16-7.20 (m, 1 H), 7.22 (d, J=8.3 Hz, 1 H), 7.51-7.55 (m, 1 H), 7.58 (d, J=8.5 Hz, 1 H)

EXAMPLE 6

Synthesis of 4-(5-chloro-2-((1-cyclopropyl-2-oxo-1H-imidazo[4,5-c]pyridin-3(2H)-yl)methyl)-1H-imidazo[4,5-b]pyridin-1yl)butyl pivalate 3

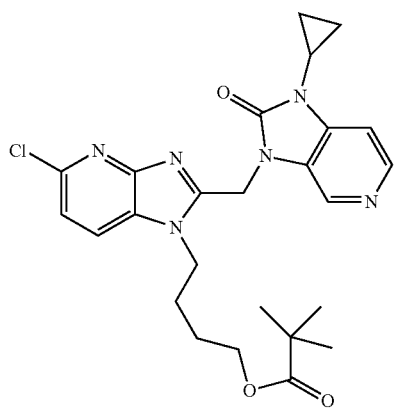

Step 1: Synthesis of (5-chloro-1H-imidazo[4,5-b]pyridin-2-yl)methanol 3-1

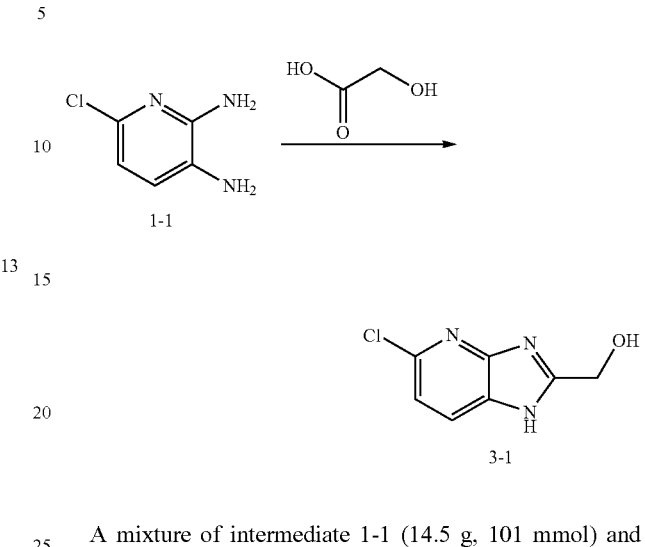

A mixture of intermediate 1-1 (14.5 g, 101 mmol) and 2-hydroxyacetic acid (16 g, 210 mmol) was stirred at 150° C. for 4 hours. The resulting mixture was cooled to 60° C. and treated with an aqueous solution of 3N HCl (70 mL), then basified to pH=7-8 by the addition of aqueous ammonia. The mixture was filtered and the solid was collected, washed with water and methyl ter-butyl ether. The product 3-1 was collected as yellow powder (17.5 g, 94%). m/z=184 (M+H)$^+$.

Step 2: Synthesis of 5-chloro-2-(trityloxymethyl)-1H-imidazo[4,5-b]pyridine 3-2

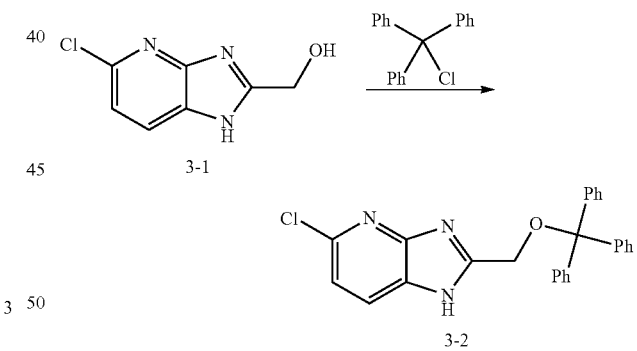

Intermediate 3-1 (17.5 g, 95.3 mmol) and triethylamine (28 mL, 190.6 mmol) was dissolved in dichloromethane (300 mL). Then, trityl chloride (40 g, 143 mmol) was added. The resulting mixture was stirred at 25° C. for 1.5 h. The reaction mixture was washed with aqueous solution of 1N hydrochloric acid and filtered. The solid was collected and washed with dichloromethane (500 mL). The filtrate was washed with aqueous solution of 1N hydrochloric acid (200 mL), and with saturated aqueous solution NaHCO$_3$ (200 mL). The organic layer was dried over Na$_2$SO$_4$, filtered and evaporated to almost dryness under vacuum. The residue was filtered. The solid was collected and washed with dichloromethane. The product 3-2 was collected (27 g, 68%). m/z=426 (M+H)$^+$.

Step 3: Synthesis of 4-(5-chloro-2-(trityloxymethyl)-1H-imidazo[4,5-b]pyridin-1-yl)butyl pivalate 3-3

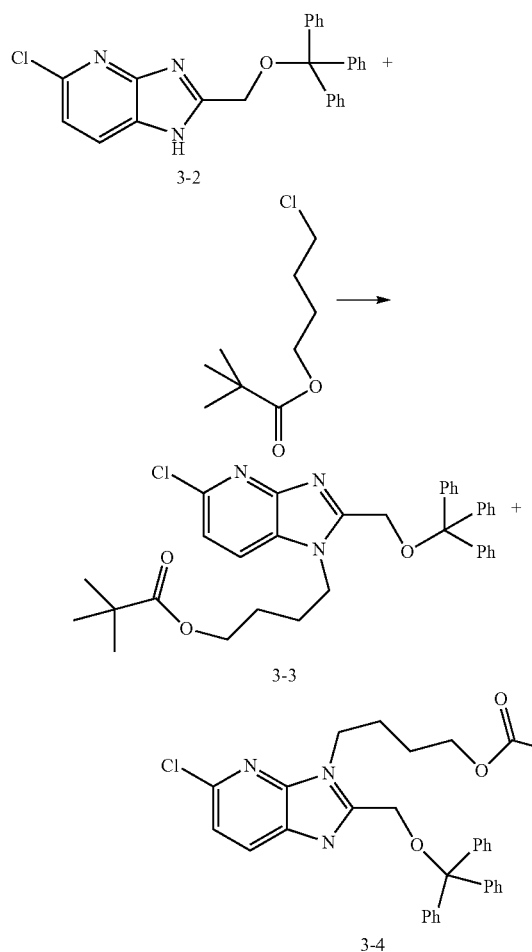

To the intermediate 3-2 (27 g, 63.4 mmol), 4-chlorobutyl pivalate (19 g, 83.8 mmol), were added cesium carbonate (40 g, 122 mmol) and potassium iodide (3 g, 18 mmol). The mixture was dissolved in DMF at 25° C. and then warmed to 80° C. and stirred for 2 hours. The reaction mixture was cooled to 25° C., filtered and the filtrate was poured into ice-water. The mixture was extracted with ethyl acetate (2×500 mL). The combined organic layers were washed with brine, dried over Na$_2$SO$_4$, filtered and evaporated under vacuum. The residue was purified by column chromatography (Eluent: ethyl acetate:petroleum ether=1:3). Two isomers were collected Compound 3-3 (5 g) and Compound 3-4 (20 g). m/z=582 (M+H)$^+$.

Step 4: Synthesis of 4-(5-chloro-2-(hydroxymethyl)-1H-imidazo[4,5-b]pyridin-1-yl)butyl pivalate 3-5

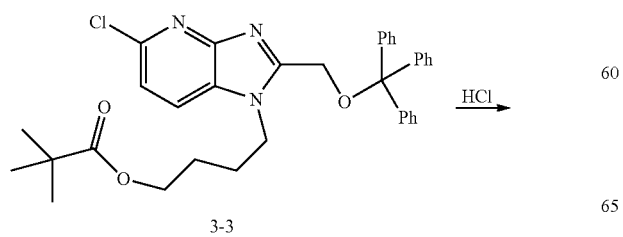

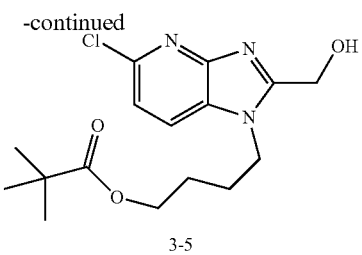

The intermediate 3-3 (5 g, 8.6 mmol) was dissolved in CH$_2$Cl$_2$ (50 mL). A solution of 4N HCl/dioxane (20 mL, 80 mmol) was added at 0° C. The mixture was stirred at 25° C. for 2 hours. The reaction mixture was evaporated under vacuum at 40-45° C. The residue was co-evaporated with CH$_2$Cl$_2$ (70 mL). Dichloromethane (70 mL) was added to the residue. The mixture was filtered and the solid was collected and washed with methyl tert-butyl ether. The hydrochloric salt of product 3-5 was collected as a white powder (2.83 g, 86%). This powder was dissolved in a mixture of water (50 mL) and dichloromethane (50 mL). Then sodium bicarbonate was added (1.02 g, 12 mmol) portionwise at 25° C., and the mixture was stirred at 25° C. for overnight. The resulting mixture was extracted with dichloromethane, dried over MgSO$_4$ and concentrated. The product 3-5 was collected as a white solid. m/z=340 (M+H)$^+$.

Step 5: Synthesis of 4-(5-chloro-2-((1-cyclopropyl-2-oxo-1H-imidazo[4,5-c]pyridin-3(2H)-yl)methyl)-1H-imidazo[4,5-b]pyridin-1yl)butyl pivalate 3

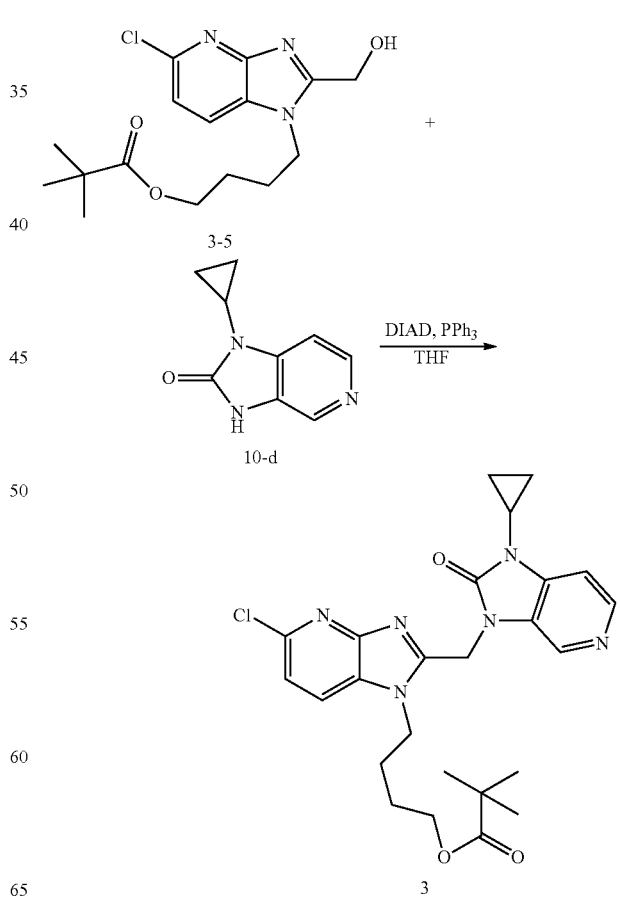

To a stirred solution of intermediate 3-5 (0.4 g, 1.16 mmol), triphenyl phosphine (0.35 g, 1.34 mmol) and compound 10-d (0.214 g, 1.22 mmol) in dry THF (30 mL) was added DIAD (94%, 0.264 mL, 1.34 mmol) dropwise at room temperature. The reaction mixture was stirred overnight. After the completion of the reaction, the mixture was concentrated to dryness and the residue was purified by column chromatography eluted with ethyl acetate/CH$_2$Cl$_2$ then CH$_2$Cl$_2$/methanol to yield the title compound 3 as a white solid (360 mg, 60%).

m/z=498 (M+H)$^+$. $^1$H NMR (400 MHz, CHLOROFORM-d) δ ppm 0.97-1.04 (m, 2H), 1.13-1.20 (m, 11 H), 1.66-1.85 (m, 4 H), 2.92 (tdd, J=6.9, 6.9, 3.8, 3.5 Hz, 1 H), 4.08 (t, J=6.1 Hz, 2 H), 4.43 (t, J=7.3 Hz, 2 H), 5.38 (s, 2 H), 7.13 (d, J=6.0 Hz, 1 H), 7.24 (d, J=8.5 Hz, 1 H), 7.64 (d, J=8.5 Hz, 1 H), 8.35 (d, J=5.3 Hz, 1 H), 8.75 (d, J=0.5 Hz, 1 H)

EXAMPLE 7

Synthesis of 3-((5-chloro-1-(4-hydroxybutyl)-1H-imidazo[4,5-b]pyridin-2-yl)methyl)-1-cyclopropyl-1H-imidazo[4,5-c]pyridin-2(3H)-one 14

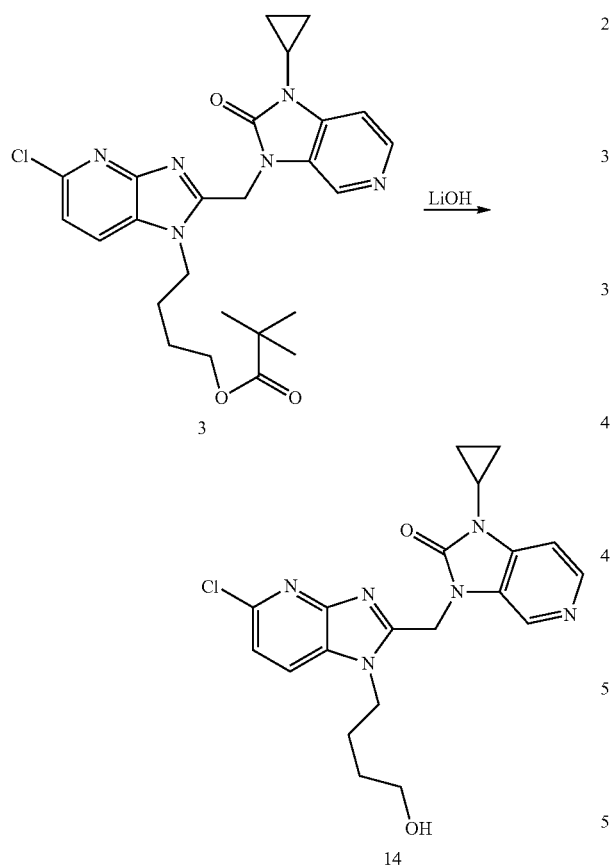

Compound 3 (0.29 g, 0.58 mmol) was dissolved in THF (15 mL) and lithium hydroxide (40 mg, 1.6 mmol) dissolved in water (5 mL) was added. The resulting mixture was stirred at room temperature overnight. The reaction mixture was poured in water and extracted with ethyl acetate. The organic layer was dried over MgSO$_4$ and concentrated. The residue was purified by column chromatography using dichloromethane and methanol. The title compound 14 was isolated as a white powder (200 mg, 80%). m/z=414 (M+H)$^+$.

$^1$H NMR (400 MHz, DMSO-d$_6$) δ ppm 0.94 (m, J=2.8 Hz, 2 H), 1.09 (m, J=5.3 Hz, 2 H), 1.39-1.51 (m, 2 H), 1.73 (quin, J=7.6 Hz, 2 H), 3.01 (tt, J=6.9, 3.5 Hz, 1 H), 3.39-3.45 (m, 2 H), 4.41 (t, J=7.4 Hz, 2 H), 5.47 (s, 2 H), 7.31 (d, J=5.0 Hz, 1 H), 7.37 (d, J=8.5 Hz, 1 H), 8.18 (d, J=8.5 Hz, 1 H), 8.28 (d, J=5.3 Hz, 1 H), 8.41 (s, 1 H).

EXAMPLE 8

Synthesis of 1-cyclopropyl-3-((1-isopentyl-1H-imidazo[4,5-b]pyridin-2-yl)methyl)-1H-benzo[d]imidazol-2(3H)-one 4

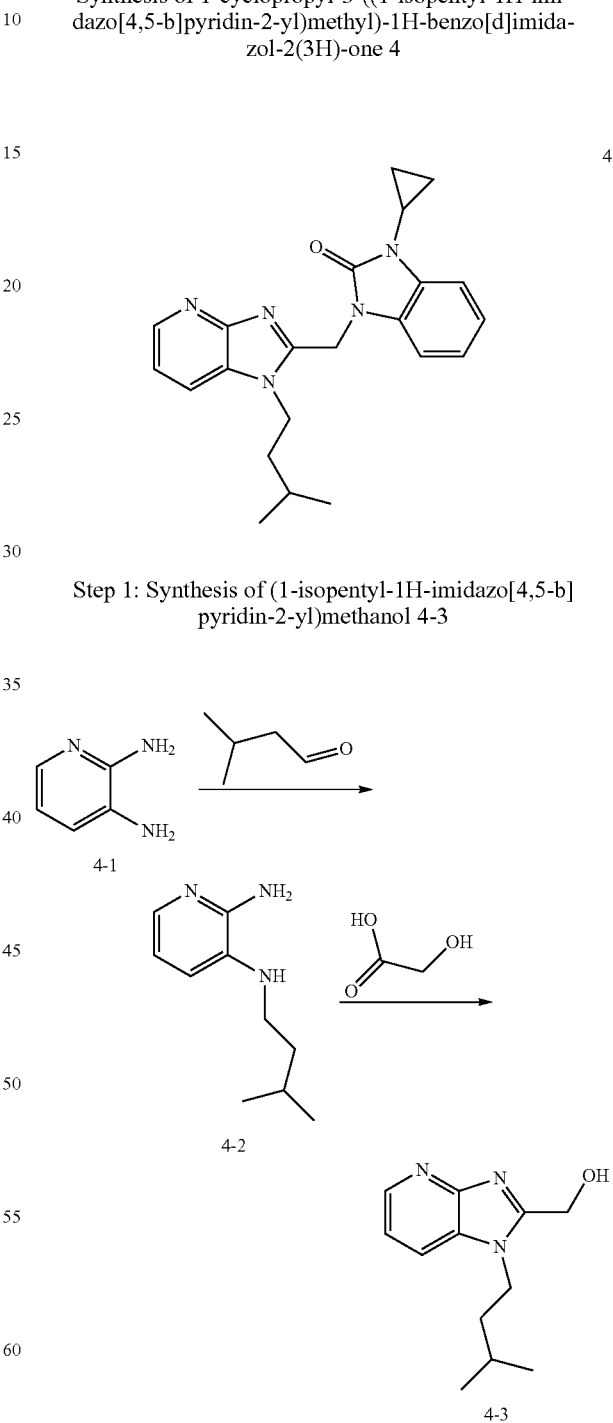

Step 1: Synthesis of (1-isopentyl-1H-imidazo[4,5-b]pyridin-2-yl)methanol 4-3

The intermediate 4-3 was prepared in the same manner as the intermediate 1-3 using pyridine-2,3-diamine 4-1 as starting material.

Step 2: 1-cyclopropyl-3-((1-isopentyl-1H-imidazo[4,5-b]pyridin-2-yl)methyl)-1H-benzo[d]imidazol-2(3H)-one 4

Compound 4 was prepared in the same manner as compound 1 using intermediates 4-3 and 13-d as starting material. m/z=376 (M+H)$^+$.

$^1$H NMR (400 MHz, CHLOROFORM-d) δ ppm 0.96 (d, J=6.5 Hz, 6 H), 0.99-1.06 (m, 2 H), 1.10-1.19 (m, 2 H), 1.37-1.51 (m, 2 H), 1.69 (dquin, J=13.3, 6.7, 6.7, 6.7, 6.7 Hz, 1 H), 2.89 (tt, J=6.9, 3.5 Hz, 1 H), 4.26-4.44 (m, 2 H), 5.40 (s, 2 H), 7.06 (m, J=8.8, 7.5, 1.3 Hz, 2 H), 7.14-7.23 (m, 2 H), 7.54 (dd, J=7.3, 1.3 Hz, 1 H), 7.62 (dd, J=8.0, 1.5 Hz, 1 H), 8.54 (dd, J=4.8, 1.3 Hz, 1 H)

EXAMPLE 9

Synthesis of 1-cyclopropyl-3-((1-isopentyl-1H-imidazo[4,5-b]pyridin-2-yl)methyl)-1H-imidazo[4,5-c]pyridin-2(3H)-one 5

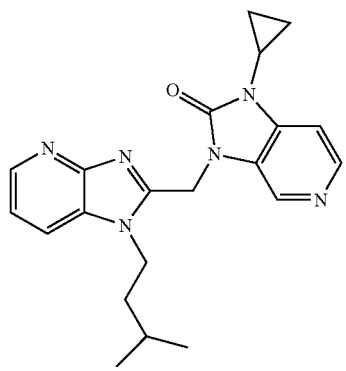

5

Compound 5 was prepared in the same manner as compound 4 using intermediate 10-d as starting material. m/z=377 (M+H)$^+$.

$^1$H NMR (360 MHz, CHLOROFORM-d) δ ppm 1.01 (m, 2 H), 0.99 (d, J=6.6 Hz, 6 H), 1.13-1.21 (m, 2 H), 1.44-1.56 (m, 2 H), 1.62-1.77 (m, 1 H), 2.87-2.96 (m, 1 H), 4.30-4.40 (m, 2 H), 5.41 (s, 2 H), 7.13 (d, J=5.5 Hz, 1 H), 7.21 (dd, J=8.1, 4.8 Hz, 1 H), 7.65 (d, J=7.7 Hz, 1 H), 8.33 (d, J=5.5 Hz, 1 H), 8.54 (d, J=4.8 Hz, 1 H), 8.70 (s, 1H)

EXAMPLE 10

Synthesis of 1-cyclopropyl-5-fluoro-3-((1-isopentyl-1H-imidazo[4,5-b]pyridin-2-yl)methyl)-1H-benzo[d]imidazol-2(3H)-one 8

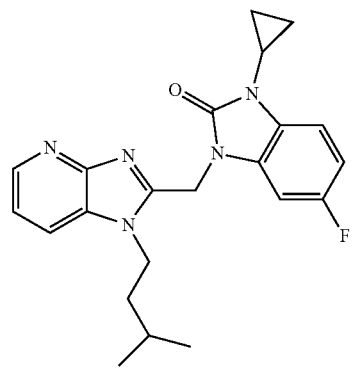

8

Compound 8 was prepared in the same manner as compound 4 using intermediate 12-d as starting material. m/z=394 (M+H)$^+$.

$^1$H NMR (400 MHz, CHLOROFORM-d) δ ppm 0.97 (d, J=6.8 Hz, 6 H), 0.99-1.04 (m, 2 H), 1.08-1.18 (m, 2 H), 1.39-1.56 (m, 2 H), 1.60-1.74 (m, 1 H), 2.77-2.97 (m, 1 H), 4.25-4.46 (m, 2 H), 5.35 (s, 2 H), 6.78 (m, J=9.0, 2.0 Hz, 1 H), 7.07 (dd, J=8.7, 4.4 Hz, 1 H), 7.20 (dd, J=8.3, 4.8 Hz, 1 H), 7.34 (dd, J=8.4, 2.4 Hz, 1 H), 7.64 (dd, J=8.0, 1.5 Hz, 1 H), 8.55 (dd, J=4.8, 1.5 Hz, 1 H)

EXAMPLE 11

Synthesis of 3-((1-isopentyl-1H-imidazo[4,5-b]pyridin-2-yl)methyl)-1-(oxetan-3-yl)-1H-imidazo[4,5-c]pyridin-2(3H)-one 9

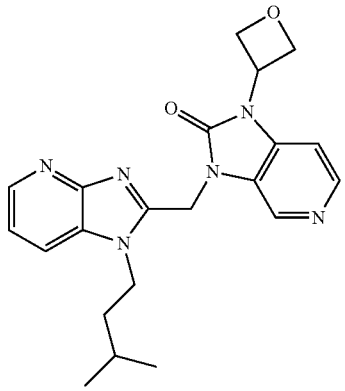

9

Compound 9 was prepared in the same manner as compound 4 using intermediate 11-d as starting material. m/z=393 (M+H)$^+$.

$^1$H NMR (400 MHz, CHLOROFORM-d) δ ppm 0.98 (d, J=6.8 Hz, 6 H), 1.48-1.59 (m, 2 H), 1.62-1.77 (m, 1 H), 4.26-4.39 (m, 2 H), 5.06-5.19 (m, 4 H), 5.43 (s, 2 H), 5.58-5.69 (m, 1 H), 7.21 (dd, J=8.3, 4.8 Hz, 1 H), 7.58 (d, J=5.3 Hz, 1 H), 7.65 (dd, J=8.0, 1.5 Hz, 1 H), 8.42 (d, J=5.3 Hz, 1 H), 8.55 (dd, J=4.8, 1.5 Hz, 1 H), 8.81 (s, 1 H).

EXAMPLE 12

Synthesis of 1-cyclopropyl-3-((1-(3-(methylsulfonyl)propyl)-1H-imidazo[4,5-b]pyridin-2-yl)methyl)-1H-imidazo[4,5-c]pyridin-2(3H)-one 7

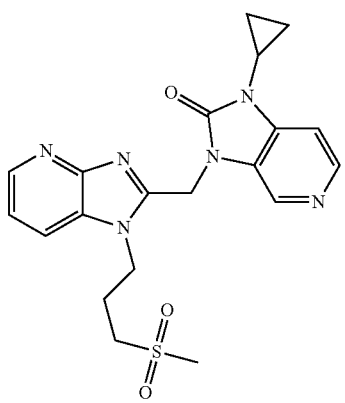

7

Step 1: Synthesis of N-(3-methylsulfonyl)propyl)-2-nitropyridin-3-amine 7-1

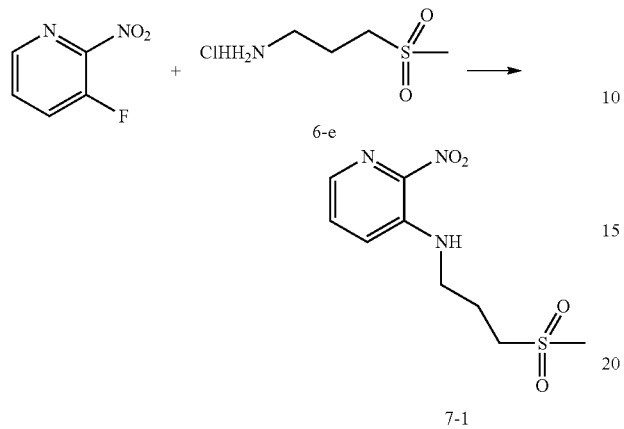

3-Fluoro-2-nitropyridine (0.7 g, 4.92 mmol, CAS 54231-35-5) was dissolved in DMF (30 mL). Then, 3-(methylsulfonyl)propan-1-amine hydrochloride 6-e (0.9 g, 5.2 mmol) was added followed by triethylamine (1.5 mL, 11.3 mmol). The resulting mixture was stirred at room temperature overnight. The mixture was poured in water and extracted with dichloromethane, dried over MgSO$_4$ and concentrated. The residue was purified by column chromatography using ethyl acetate to yield the intermediate 7-1 as an orange solid (1.2 g, 93%). m/z=260 (M+H)$^+$.

Step 2: Synthesis of N$^3$-(3-methylsulfonyl)propyl) pyridine-2,3-diamine 7-2

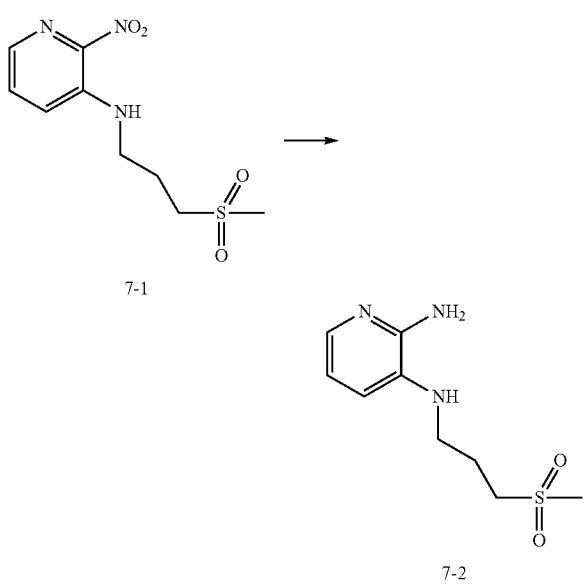

Intermediate 7-1 (1.2 g, 4.62 mmol) in THF (300 mL) was hydrogenated at 20° C. with wet 10% Pd/C (0.5 g) as a catalyst overnight. After uptake of H$_2$ (3 eq), the catalyst was filtered off and the filtrate was evaporated. The residue was washed with methyl ter-butyl ether to afford the title compound 7-2 as a light yellow powder (1 g, 94%). m/z=230 (M+H)$^+$.

Step 3: Synthesis of (1-(3-(methylsulfonyl)propyl)-1H-imidazo[4,5-b]pyridin-2-yl)methanol 7-3

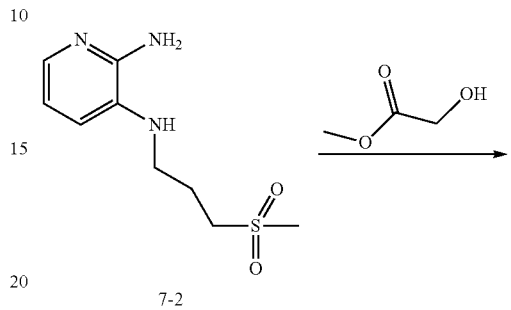

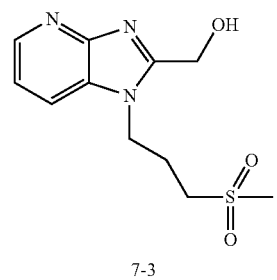

A mixture of intermediate 7-2 (1 g, 4.36 mmol) and methyl 2-hydroxyacetate (2 mL, 26 mmol) was stirred at 130° C. overnight. The resulting mixture was allowed to cool down to room temperature and diluted with dichloromethane. The resulting mixture was poured in water and extracted with dichloromethane. The organic layer was dried over MgSO$_4$ filtered and concentrated. The water layer was evaporated then both residues were mixed and purified by column chromatography dichloromethane/methanol. The product 7-3 was collected as a white powder (0.43 g, 36%). m/z=270 (M+H)$^+$.

Step 4: Synthesis of 1-cyclopropyl-3-((1-(3-(methylsulfonyl)propyl)-1H-imidazo[4,5-b]pyridin-2-yl)methyl)-1H-imidazo[4,5-c]pyridin-2(3H)-one 7

Compound 7 was prepared in the same manner as compound 1 using intermediates 7-3 and 10-d as starting material. m/z=427 (M+H)$^+$.

$^1$H NMR (400 MHz, DMSO-d$_6$) δ ppm 0.89-0.97 (m, 2 H), 1.03-1.12 (m, 2 H), 2.10-2.25 (m, 2 H), 3.00 (s, 3 H), 2.93-3.05 (m, 1 H), 3.19-3.27 (m, 2 H), 4.52 (t, J=7.4 Hz, 2 H), 5.48 (s, 2 H), 7.29 (m, J=5.0 Hz, 2 H), 8.10 (dd, J=8.0, 1.5 Hz, 1 H), 8.27 (d, J=5.3 Hz, 1 H), 8.38 (dd, J=4.8, 1.5 Hz, 1 H), 8.45 (s, 1 H)

EXAMPLE 13

Synthesis of 1-cyclopropyl-3-((1-(3-(methoxypropyl)-1H-imidazo[4,5-b]pyridin-2-yl)methyl)-1H-imidazo[4,5-c]pyridin-2(3H)-one 10

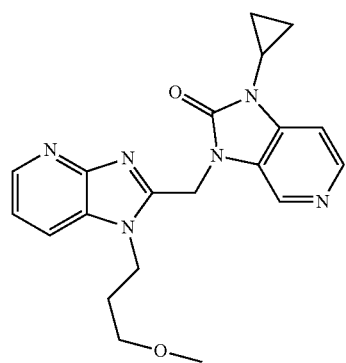

Step 1: Synthesis of N³-(3-methoxypropyl)pyridine-2,3-diamine 10-2

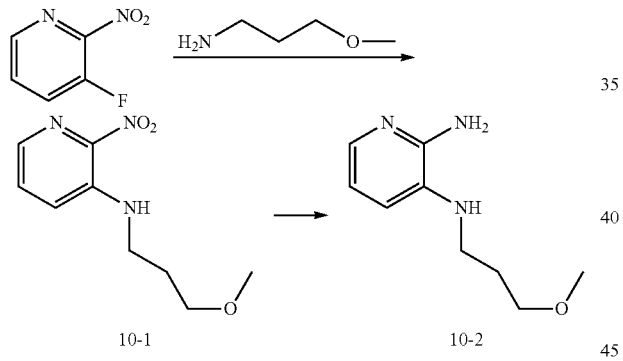

The intermediate 10-2 was prepared in the same manner as intermediate 7-2 using 3-methoxypropan-1-amine as starting material.

Step 2: Synthesis of 2-(diethoxymethyl)-1-(3-methoxypropyl)-1H-imidazo[4,5-b]pyridine 10-3

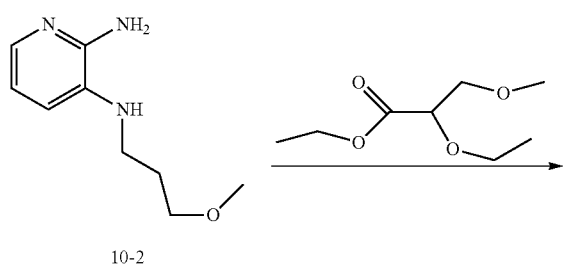

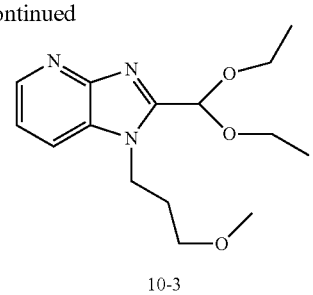

Intermediate 10-2 (10 g, 34.43 mmol) was dissolved in ethanol (70 mL). Then ethyl 2,2-diethoxyacetate (7.39 mL, 41.3 mmol) and sodium ethanolate (14.14 mL, 37.8 mmol) were added. The resulting mixture was refluxed for 4 days. The dark solution was allowed to cool down to room temperature then the solvent was removed under vacuum. The residue was dissolved in water (300 mL) and dichloromethane was added. The mixture was extracted with dichloromethane. The combined organic layers were dried over $Na_2SO_4$, filtered and evaporated. The residue was purified by column chromatography eluting with ethyl acetate/dichloromethane. The intermediate 10-3 was collected (5.15 g, 48%). m/z=294 (M+H)⁺.

Step 3: Synthesis of 1-(3-methoxypropyl)-1H-imidazo[4,5-b]pyridine-2-carbaldehyde 10-4

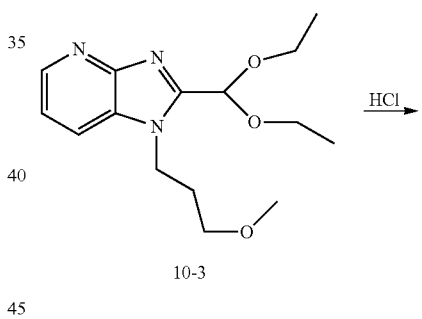

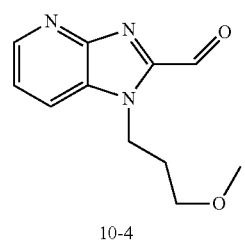

A solution of intermediate 10-3 (5.15 g, 17.55 mmol) in an aqueous solution of 1N hydrochloric acid (79 mL, 79 mmol) was stirred at 60° C. for 2 days. The resulting mixture was allowed to cool down to room temperature then ethyl acetate and water were added. A saturated solution of $Na_2CO_3$ was added to adjust the pH to basic and the mixture was extracted with ethyl acetate. The organic layer was washed with brine, dried over $Na_2SO_4$, filtered and evaporated under vacuum. Compound 10-4 was collected as a brown dark oil (3 g, 76%).

Step 4: Synthesis of 1-(3-methoxypropyl)-1H-imidazo[4,5-b]pyridin-2-yl)methanol 10-5

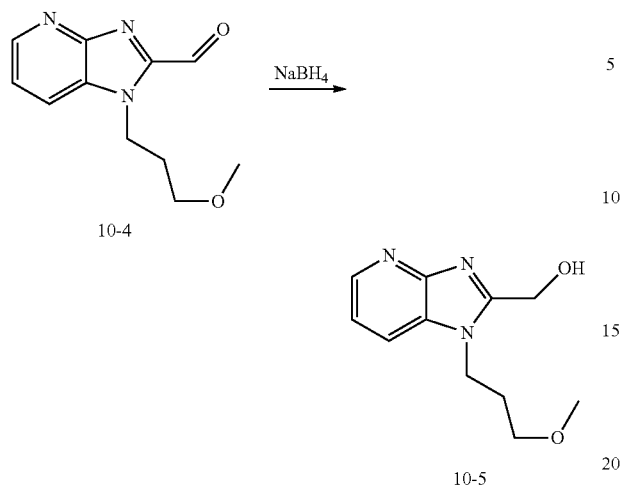

To a solution of intermediate 10-4 (3 g, 10.4 mmol) in THF (40 mL) and methanol (40 mL) sodium borohydride (0.8 g, 21 mmol) was added portionwise at 0° C. The resulting mixture was stirred at room temperature overnight. The solvent was removed then the residue was dissolved in ethyl acetate (50 mL), water was added (100 mL). The resulting mixture was extracted with ethyl acetate (3×50 mL). The separated organic layer was washed with brine, dried over $Na_2SO_4$, filtered and evaporated under vacuum. The residue was purified by column chromatography using dichloromethane/methanol. The title compound was collected as an orange oil (1 g, 42%). m/z=222 (M+H)$^+$.

Step 5: Synthesis of 1-cyclopropyl-3-((1-(3-(methoxypropyl)-1H-imidazo[4,5-b]pyridin-2-yl)methyl)-1H-imidazo[4,5-c]pyridin-2(3H)-one 10

Compound 10 was prepared in the same manner as compound 1 using intermediates 10-5 and 10-d as starting material m/z=379 (M+H)$^+$.

$^1$H NMR (400 MHz, DMSO-d$_6$) δ ppm 0.88-0.97 (m, 2 H), 1.03-1.14 (m, 2 H), 1.99 (quin, J=6.3 Hz, 2 H), 3.00 (tt, J=6.8, 3.6 Hz, 1 H), 3.23 (s, 3 H), 3.29 (t, J=5.9 Hz, 2 H), 4.44 (t, J=6.8 Hz, 2 H), 5.46 (s, 2 H), 7.26 (dd, J=8.0, 4.8 Hz, 1 H), 7.30 (d, J=5.3 Hz, 1 H), 7.97-8.06 (m, 1 H), 8.27 (d, J=5.3 Hz, 1 H), 8.33-8.39 (m, 1 H), 8.41 (s, 1 H).

EXAMPLE 14

Synthesis of 3-((1-(3-methoxypropyl)-1H-imidazo[4,5-b]pyridin-2-yl)methyl)-1-(oxetan-3-yl)-1H-imidazo[4,5-c]pyridin-2(3H)-one 12

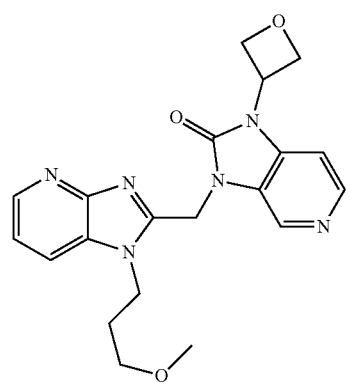

Compound 12 was prepared in the same manner as compound 10 using intermediate 11-d as starting material m/z=395 (M+H)$^+$.

$^1$H NMR (400 MHz, DMSO-d$_6$) δ ppm 2.01 (quin, J=6.3 Hz, 2 H), 3.23 (s, 3 H), 3.30 (t, J=1.0 Hz, 2 H), 4.45 (t, J=6.9 Hz, 2 H), 4.93-5.04 (m, 2 H), 5.09 (t, J=6.7 Hz, 2 H), 5.50 (s, 2 H), 5.53-5.64 (m, 1 H), 7.26 (dd, J=8.0, 4.8 Hz, 1 H), 7.55 (d, J=5.3 Hz, 1 H), 8.02 (dd, J=8.0, 1.3 Hz, 1 H), 8.32 (d, J=5.3 Hz, 1 H), 8.36 (dd, J=4.8, 1.3 Hz, 1 H), 8.50 (s, 1 H).

EXAMPLE 15

Synthesis of 1-cyclopropyl-5-fluoro-3-((1-(3-methoxypropyl)-1H-imidazo[4,5-b]pyridin-2-yl)methyl)-1H-benzo[d]imidazol-2(3H)-one 15

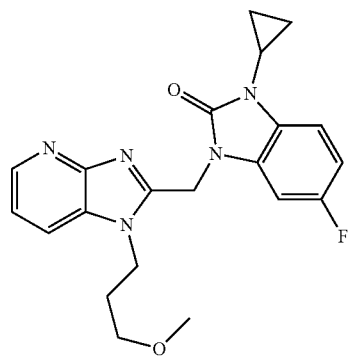

Compound 15 was prepared in the same manner as compound 10 using intermediate 12-d as starting material m/z=396 (M+H)$^+$.

$^1$H NMR (400 MHz, DMSO-d$_6$) δ ppm 0.84-0.95 (m, 2 H), 1.01-1.13 (m, 2 H), 1.97 (m, J=6.3, 6.3, 6.3, 6.3 Hz, 2 H), 2.94 (m, J=6.8, 6.8, 3.5, 3.5 Hz, 1 H), 3.23 (s, 3 H), 3.25-3.29 (m, 2 H), 4.43 (t, J=6.9 Hz, 2 H), 5.38 (s, 2 H), 6.84-6.99 (m, 1 H), 7.17 (dd, J=9.2, 2.4 Hz, 1 H), 7.22 (dd, J=1.0 Hz, 1 H), 7.26 (dd, J=1.0 Hz, 1 H), 8.00 (dd, J=8.0, 1.3 Hz, 1 H), 8.36 (dd, J=4.5, 1.3 Hz, 1 H).

EXAMPLE 16

Synthesis of 1-cyclopropyl-3-((1-(3-(fluoropropyl)-1H-imidazo[4,5-b]pyridin-2-yl)methyl)-1H-imidazo[4,5-c]pyridin-2(3H)-one 11

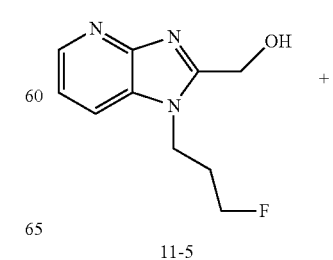

43
-continued

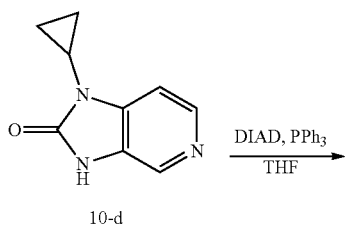

10-d

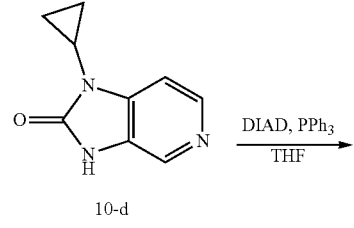

10-d

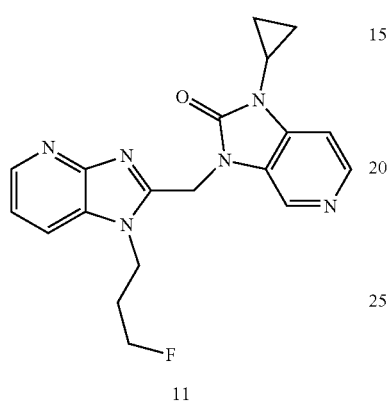

11

The intermediate 11-5 was prepared in the same manner as intermediate 10-5 using 3-fluoropropan-1-amine hydrochloride (CAS 64068-31-1) and 3-fluoro-2-nitropyridine (CAS 54231-35-35) as starting materials.

Compound 11 was prepared in the same manner as compound 10 using intermediates 11-5 and 10-d as starting material m/z=337 (M+H)+.

$^1$H NMR (400 MHz, DMSO-d$_6$) δ ppm 0.88-0.97 (m, 2 H), 1.02-1.11 (m, 2 H), 2.06-2.26 (m, 2 H), 3.00 (dt, J=6.9, 3.3 Hz, 1 H), 4.39-4.63 (m, 4 H), 5.46 (s, 2 H), 7.27 (dd, J=8.2, 4.6 Hz, 1 H), 7.30 (d, J=5.3 Hz, 1 H), 8.04 (dd, J=8.0, 1.5 Hz, 1 H), 8.27 (d, J=5.3 Hz, 1 H), 8.37 (dd, J=4.8, 1.5 Hz, 1 H), 8.41 (s, 1 H).

EXAMPLE 17

Synthesis of 3-((6-bromo-3-isopentyl-3H-imidazo[4,5-b]pyridin-2-yl)methyl)-1-cyclopropyl-1H-imidazo[4,5-c]pyridin-2(3H)-one 16

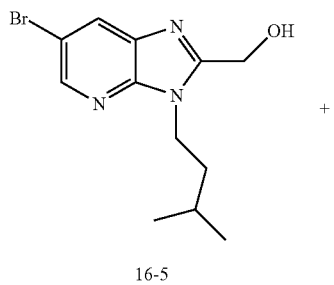

16-5

+

44
-continued

16

Intermediate 16-5 was prepared following the 5 steps synthesis reported for intermediate 10-5 using 5-bromo-2-chloro-3-nitropyridine (CAS 67443-38-3) and 3-methylbutane-1-amine (CAS 107-85-7) as starting material.

Compound 16 was prepared in the same manner as compound 10 using intermediates 16-5 and 10-d as starting material. m/z=456 (M+H)+.

$^1$H NMR (360 MHz, CHLOROFORM-d) δ ppm 0.97 (d, J=6.6 Hz, 6 H), 0.99-1.07 (m, 2 H), 1.18-1.21 (m, 2 H), 1.54-1.62 (m, 2 H), 1.68 (tt, J=13.3, 6.6 Hz, 1 H), 2.93 (tdd, J=6.9, 6.9, 3.7, 3.5 Hz, 1 H), 4.39 (m, J=8.1 Hz, 2 H), 5.36 (s, 2 H), 7.16 (dd, J=5.1, 0.7 Hz, 1 H), 8.15 (d, J=2.2 Hz, 1 H), 8.34 (d, J=5.1 Hz, 1 H), 8.41 (d, J=1.8 Hz, 1 H), 8.57 (d, J=0.7 Hz, 1 H).

EXAMPLE 18

Synthesis of 3-((6-bromo-3-isopentyl-3H-imidazo[4,5-b]pyridin-2-yl)methyl)-1-(oxetan-3-yl)-1H-imidazo[4,5-c]pyridin-2(3H)-one 18

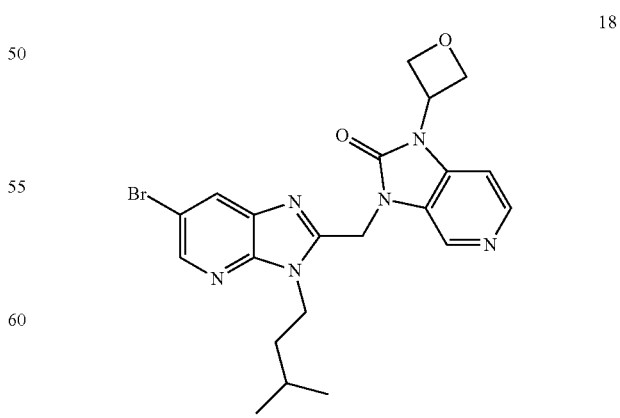

18

Compound 18 was prepared in the same manner as compound 16 using intermediates 16-5 and 11-d as starting material m/z=472 (M+H)+.

¹H NMR (400 MHz, CHLOROFORM-d) δ ppm 0.96 (d, J=6.5 Hz, 6 H), 1.50-1.61 (m, 2 H), 1.67 (m, J=6.5 Hz, 1 H), 4.26-4.49 (m, 2 H), 5.02-5.24 (m, 4 H), 5.38 (s, 2 H), 5.65 (tdd, J=7.6, 7.6, 5.9, 5.8 Hz, 1 H), 7.61 (d, J=5.3 Hz, 1 H), 8.14 (d, J=2.0 Hz, 1 H), 8.31-8.50 (m, 2 H), 8.66 (s, 1 H)

EXAMPLE 19

Synthesis of 1-((6-bromo-3-isopentyl-3H-imidazo[4,5-b]pyridin-2-yl)methyl)-3-cyclopropyl-1H-benzo[d]imidazol-2(3H)-one 30

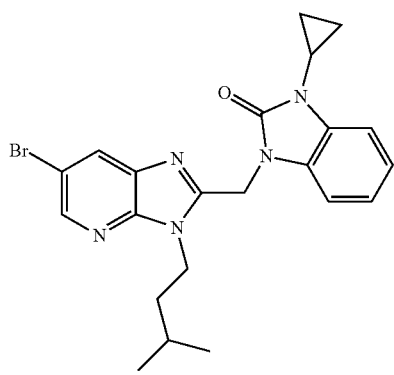

30

Compound 30 was prepared in the same manner as compound 16 using intermediates 16-5 and 13-d as starting material m/z=455 (M+H)⁺.

¹H NMR (400 MHz, CHLOROFORM-d) δ ppm 0.94 (d, J=6.5 Hz, 6 H), 1.00-1.07 (m, 2 H), 1.14 (m, J=7.3, 1.5 Hz, 2 H), 1.41-1.54 (m, 2 H), 1.66 (m, J=13.4, 6.6, 6.6, 6.6 Hz, 1 H), 2.90 (tdd, J=6.9, 6.9, 3.8, 3.5 Hz, 1 H), 4.32-4.46 (m, 2 H), 5.34 (s, 2 H), 7.03 (m, J=7.7, 1.4 Hz, 1 H), 7.09 (td, J=7.7, 1.3 Hz, 1 H), 7.20 (dd, J=7.7, 0.6 Hz, 1 H), 7.28 (dd, J=7.7, 0.6 Hz, 1 H), 8.15 (d, J=2.0 Hz, 1 H), 8.40 (d, J=2.0 Hz, 1 H)

EXAMPLE 20

Synthesis of 1-cyclopropyl-3-((3-isopentyl-3H-imidazo[4,5-b]pyridin-2-yl)methyl)-1H-imidazo[4,5-c]pyridin-2(3H)-one 24

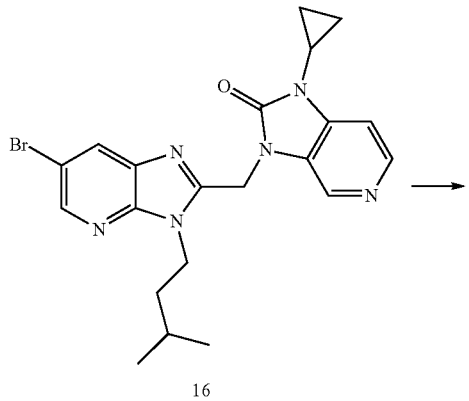

16

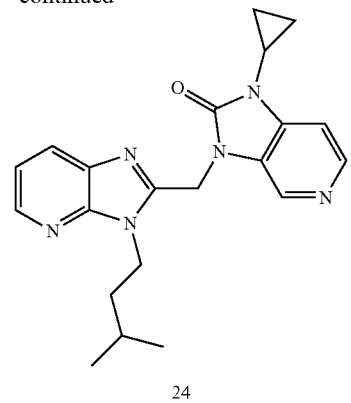

24

To intermediate 16 (0.49 g, 1.09 mmol) in methanol (30 mL) were added potassium acetate (0.128 g, 1.3 mmol), thiophenol (0.5 mL) and wet 10% Pd/C (0.2 g). The reaction mixture was stirred at 25° C. under hydrogen atmosphere. After uptake of H₂ (1 eq), the catalyst was filtered off and the filtrate was evaporated. The residue was dissolved in water and dichloromethane. The resulting mixture was successively extracted with dichloromethane dried over MgSO₄ and concentrated. The residue was purified by column chromatography using dichloromethane/ methanol. The title compound 24 was collected as a white powder (333 mg, 81%). m/z=377 (M+H)⁺.

¹H NMR (400 MHz, CHLOROFORM-d) δ ppm 0.97 (d, J=6.8 Hz, 6 H), 1.03-1.06 (m, 2 H), 1.15-1.21 (m, 2 H), 1.51-1.60 (m, 2 H), 1.67-1.71 (m, 1 H), 2.9-2.95 (m, 1 H), 4.37-4.44 (m, 2 H), 5.38 (s, 1 H), 7.14 (dd, J=5.3, 0.8 Hz, 1 H), 7.22 (dd, J=8.0, 4.8 Hz, 1 H), 8.02 (dd, J=8.2, 1.4 Hz, 1 H), 8.33 (d, J=5.3 Hz, 1 H), 8.38 (dd, J=4.8, 1.5 Hz, 1 H), 8.58 (s, 1 H)

EXAMPLE 21

Synthesis of methyl 2-((1-cyclopropyl-2-oxo-1H-imidazo[4,5-c]pyridin-3(2H)-yl)methyl)-3-isopentyl-3H-imidazo[4,5-b]pyridine-6-carboxylate 26

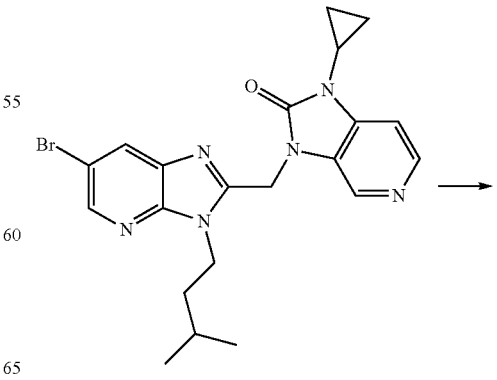

16

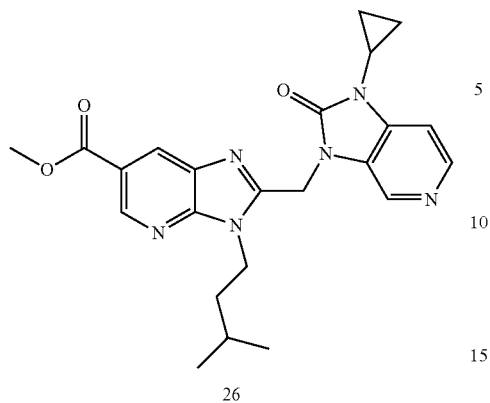

26

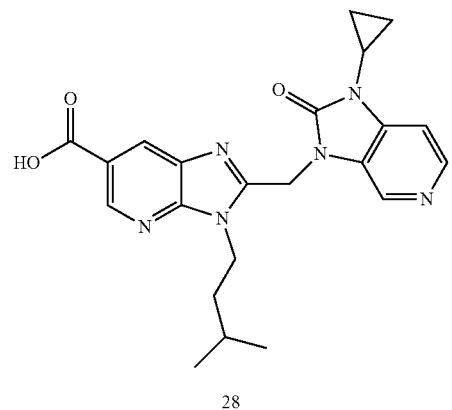

28

The mixture of compound 16 (1 g, 2.15 mmol), palladium acetate (9.8 mg, 0.043 mmol), 1,3-bis(diphenylphosphino)propane (35.4 mg, 0.086 mmol), potassium acetate (316 mg, 3.22 mmol) and methanol (10 mL) in THF (100 mL) was charged in an autoclave under nitrogen atmosphere.

The autoclave was closed and pressurized to 20 bar of carbon monoxide and the reaction was carried out for 16 hours at 125° C. The reaction mixture was allowed to cool down to room temperature and filtered over an acrodisk. The solvent was evaporated and the residue was purified by column chromatography using ethyl acetate/ methanol. The title compound 26 was collected as a white powder (870 mg, 91%). m/z=435 (M+H)$^+$.

$^1$H NMR (360 MHz, CHLOROFORM-d) δ ppm 0.98 (d, J=6.6 Hz, 6 H), 1.18 (m, J=5.9 Hz, 2 H), 1.52-1.61 (m, 2 H), 1.61-1.78 (m, 1 H), 2.93 (tdd, J=6.9, 6.9, 3.7, 3.5 Hz, 1 H), 3.97 (s, 3 H), 4.35-4.50 (m, 2 H), 5.39 (s, 2 H), 7.16 (d, J=5.1 Hz, 1 H), 8.35 (d, J=5.1 Hz, 1 H), 8.58 (s, 1 H), 8.64 (d, J=1.8 Hz, 1 H), 9.06 (d, J=1.8 Hz, 1 H)

EXAMPLE 22

Synthesis of 2-((1-cyclopropyl-2-oxo-1H-imidazo[4,5-c]pyridin-3(2H)-yl)methyl)-3-isopentyl-3H-imidazo[4,5-b]pyridine-6-carboxylic acid 28

Compound 26 (0.84 g, 1.89 mmol) was dissolved in THF (15 mL) and lithium hydroxide (544 mg, 22.7 mmol) dissolved in water (10 mL) was added. The resulting mixture was stirred at room temperature overnight. The pH of the resulting mixture was adjusted to pH=4 by addition of a 1 M solution of hydrochloric acid. Then the mixture was extracted with ethyl acetate. The organic layer was dried over MgSO$_4$ and concentrated. The title compound 28 was isolated as a white powder (690 mg, 84%).

m/z=421 (M+H)$^+$.

$^1$H NMR (400 MHz, DMSO-d$_6$) δ ppm 0.94 (d, J=5.8 Hz, 8 H), 1.081-1.12 (m, 2 H), 1.60-1.65 (m, 3 H), 3.00 (br. s., 1 H), 4.40-4.45 (m, 2 H), 5.48 (s, 2 H), 7.30 (d, J=5.3 Hz, 2 H), 8.27 (d, J=5.0 Hz, 1 H), 8.39 (s, 1 H), 8.43 (d, J=1.3 Hz, 1 H), 8.91 (d, J=1.3 Hz, 1 H)

EXAMPLE 23

Synthesis of 2-((1-cyclopropyl-2-oxo-1H-imidazo[4,5-c]pyridin-3(2H)-yl)methyl)-3-isopentyl-3H-imidazo[4,5-b]pyridine-6-carbonitrile 27

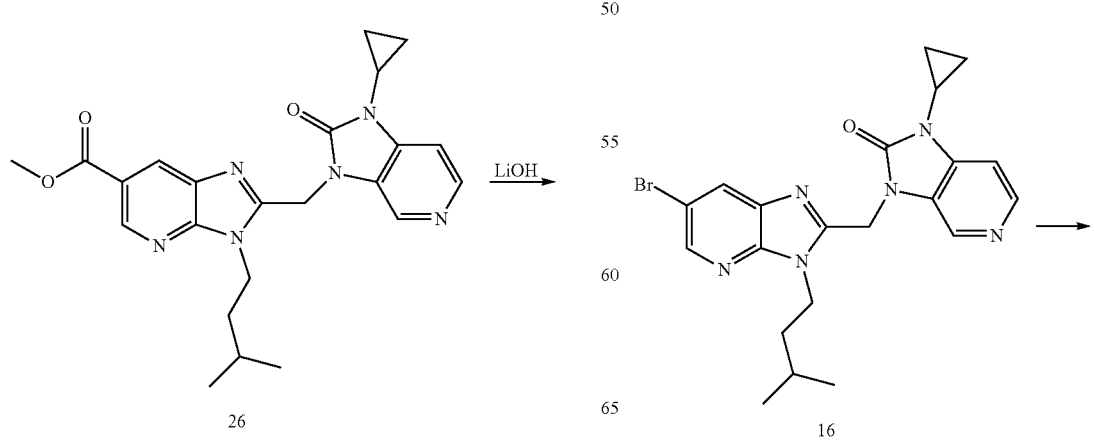

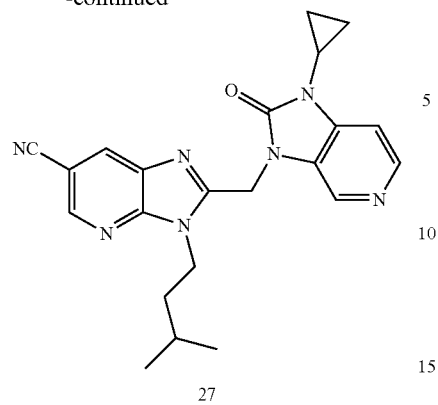

27

The mixture of compound 16 (0.5 g, 1 mmol), Dichloro(diphenylphosphinoferrocene)palladium (78.7 mg, 0.108 mmol), dicyanozinc (0.505 g, 4.3 mmol) and triethyl amine (0.6 mL, 4.3 mmol) in dioxane (10 mL) under nitrogen atmosphere was irradiated for 1 h in a microwave reactor at 125° C. The resulting mixture was allowed to cool down to room temperature then filtered over dicalite. The filtrate was evaporated to dryness. The peσιδνε was purified by column chromatography using EtOAc/MeOH 8-2. The title compound 27 was isolated as a white solid (200 mg, 45%). m/z=402 (M+H)⁺.

¹H NMR (360 MHz, CHLOROFORM-d) δ ppm 0.95-1.08 (m, 2 H), 1.03 (d, J=6.2 Hz, 6 H), 1.17-1.29 (m, 3 H), 1.64-1.80 (m, 2 H), 2.91-3.05 (m, 1 H), 4.38-4.49 (m, 2 H), 5.44 (s, 2 H), 7.27-7.31 (m, 1 H), 8.17-8.33 (m, 1 H), 8.49-8.58 (m, 1 H), 8.62 (d, J=1.8 Hz, 1 H), 8.89-8.99 (m, 1 H)

EXAMPLE 24

Synthesis of 3-((6-(aminomethyl)-3-isopentyl-3H-imidazo[4,5-b]pyridine-2-yl)methyl)-1-cyclopropyl-1H-imidazo[4,5-c]pyridin-2(3H)-one 17

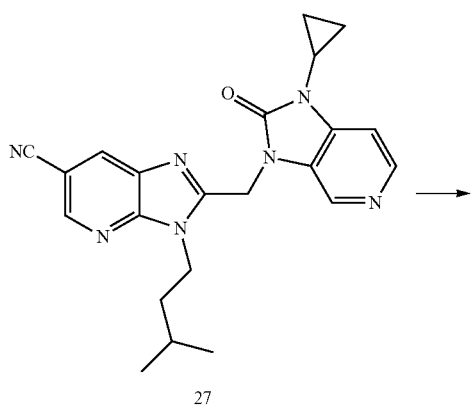

27

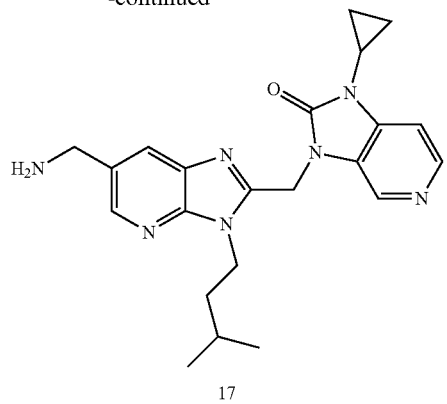

17

Compound 27 (125 mg, 0.31 mmol) in methanol/NH₃ (100 mL) was hydrogenated at 20° C. with Raney Nickel (50 mg) as a catalyst overnight. After uptake of H₂ (2 eq), the catalyst was filtered off and the filtrate was evaporated. The residue was purified by column chromatography using dichloromethane/MeOH/NH₃. The title compound 17 was isolated as a white solid (25.5 mg, 20%). m/z=406 (M+H)⁺.

¹H NMR (400 MHz, DMSO-d₆) δ ppm 0.92 (d, J=6.3 Hz, 8 H), 1.03-1.13 (m, 2 H), 1.45-1.69 (m, 3 H), 2.99 (tdd, J=7.0, 7.0, 3.6, 3.5 Hz, 1 H), 3.81 (s, 2 H), 4.26-4.41 (m, 2 H), 5.42 (s, 2 H), 7.29 (dd, J=5.3, 0.8 Hz, 1 H), 7.96 (d, J=2.0 Hz, 1 H), 8.25 (d, J=5.3 Hz, 1 H), 8.30 (d, J=2.0 Hz, 1 H), 8.37 (s, 1 H)

EXAMPLE 25

Synthesis of 2-((1-cyclopropyl-2-oxo-1H-imidazo[4,5-c]pyridin-3(2H)-yl)methyl)-3-isopentyl-3H-imidazo[4,5-b]pyridin-6-ylboronic acid 23

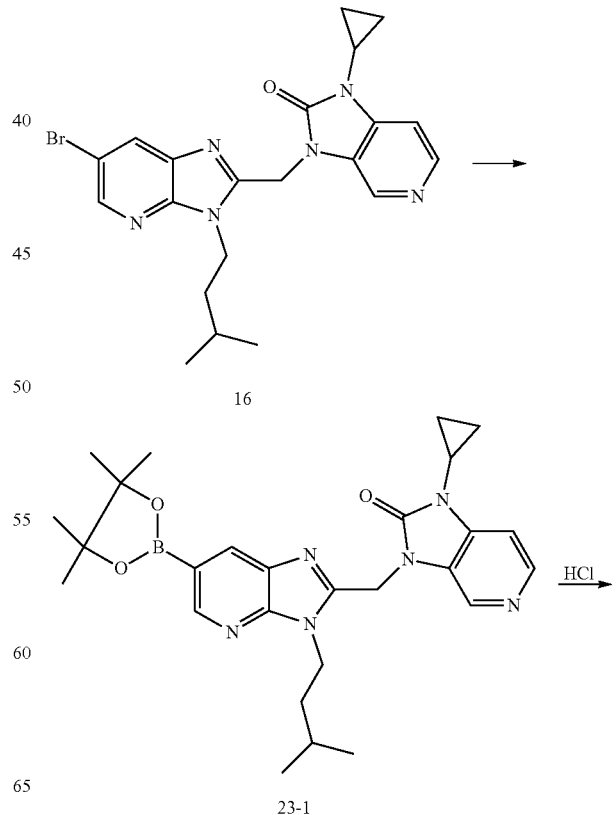

-continued

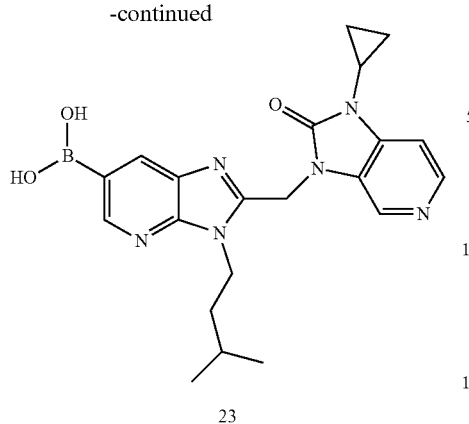

23

The mixture of compound 16 (0.5 g, 1 mmol), 4,4,4',4',5,5,5',5'-octamethyl-2,2'-bi(1,3,2-dioxaborolane (0.382 g, 1.5 mmol) and potassium acetate (0.16 g, 1.6 mmol) in dioxane (20 mL) under argon atmosphere was stirred at room temperature for 10 minutes. To the resulting mixture dichloro (diphenylphosphinoferrocene)palladium (39 mg, 0.05 mmol) was added. The resulting mixture was warmed to 115° C. for 3 hours. The mixture was allowed to cool down to room temperature then the solvent was removed. The residue (23-1) was dissolved in acetonitrile (40 mL) and an aqueous solution of hydrochloric acid 6 M (1.7 mL, 10 mmol) was added. The resulting mixture was stirred at 110° C. for 2 hours. The mixture was allowed to cool down to room temperature and water (30 mL) was added the pH was adjusted to pH=7 by addition of a solution 7N of ammoniac in methanol. The resulting mixture was concentrated and the residue was purified by preparative HPLC. The title compound 23 was isolated as a white solid (309 mg, 67%). m/z=421 (M+H)$^+$.

$^1$H NMR (400 MHz, DMSO-d$_6$) δ ppm 0.92 (d, J=6.5 Hz, 8 H), 1.08-1.16 (m, 2 H), 1.47-1.71 (m, 3 H), 2.99 (tdd, J=7.0, 7.0, 3.6, 3.5 Hz, 1 H), 4.35 (m, J=7.8 Hz, 2 H), 5.43 (s, 2 H), 7.29 (d, J=5.0 Hz, 1 H), 8.21 (s, 2 H), 8.25 (d, J=5.3 Hz, 1 H), 8.32 (d, J=1.5 Hz, 1 H), 8.38 (s, 1 H), 8.68 (d, J=1.5 Hz, 1 H)

EXAMPLE 26

Synthesis of 3-((6-bromo-3-(4-hydroxybutyl)-3H-imidazo[4,5-b]pyridin-2-yl)methyl)-1-cyclopropyl-1H-imidazo[4,5-c]pyridin-2(3H)-one 19

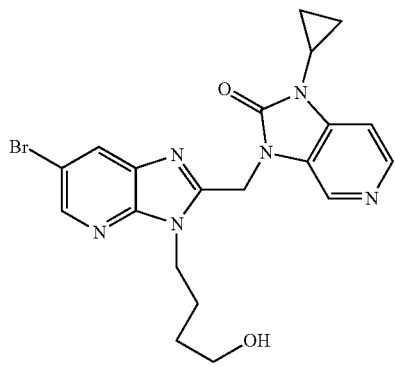

19

Step 1: Synthesis of 5-bromo-N-(4-(tert-butyldiphenylsilyloxy)butyl)-3-nitropyridin-2amine 19-1

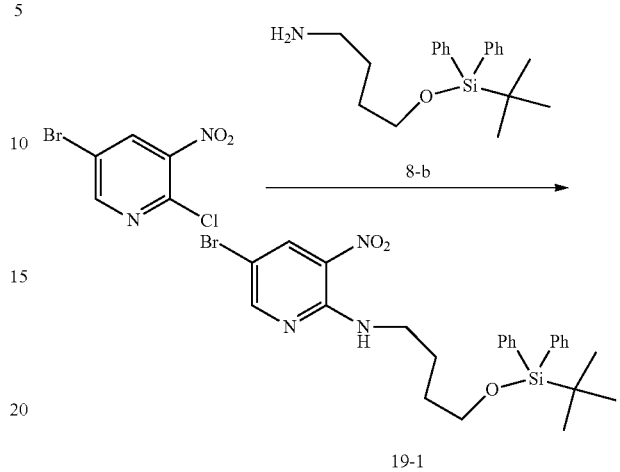

19-1

A mixture of 5-bromo-2-chloro-3-nitropyridine (CAS 67443-38-3) (33 g, 101 mmol), 4-(tert-butyldiphenylsilyloxy)butan-1-amine 8-b (20 g, 84.2 mmol), potassium carbonate (23.3 g, 168 mmol) and potassium iodide (1.4 g, 8.4 mmol) in CH$_3$CN (200 mL) was stirred at 20° C. for 15 h. The resulting mixture was treated with CH$_2$Cl$_2$ (400 mL) and water (400 mL). The separated aqueous layer was extracted with CH$_2$Cl$_2$ (2×200 mL). The combined organic layers were washed with brine (400 mL), dried over Na$_2$SO$_4$, filtered and evaporated under vacuum. The intermediate 19-1 was obtained (44 g, 90%). m/z=530 (M+H)$^+$.

Step 2: Synthesis of 5-bromo-N$^2$-(4-(tert-butyldiphenylsilyloxy)butyl)pyridine-2,3-diamine 19-2

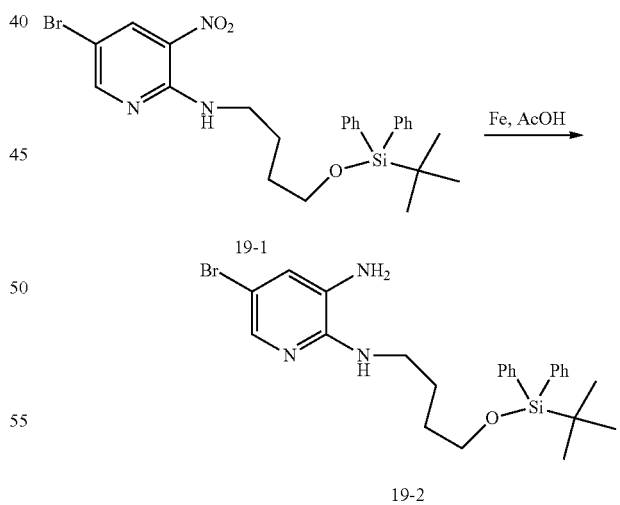

19-2

Intermediate 19-1 (48 g, 84 mmol) was dissolved in acetic acid (270 mL) and water (25 mL). The resulting mixture was warmed to 50° C. Iron (Fe) (36.1 g, 647 mmol) was added very slowly to the mixture in 20 min. The mixture was stirred at 50° C. for 2 h and allowed to cool down to room temperature. Water (400 mL) was added and the mixture was filtered through a celite pad. The residue collected on the filter was washed with water. The filtrate was treated with ethyl acetate (2×300 mL). The organic layer was separated and washed with water (2×400 mL) and brine (500 mL). The organic layer was dried over Na$_2$SO$_4$, filtered and evaporated under vacuum. The residue was co-evaporated with toluene under vacuum to give intermediate 19-2 (40 g, 90%).

Step 3, 4 and 5: Synthesis of (6-bromo-3-(4-(tert-butyldiphenylsilyloxy)butyl)-3H-imidazo[4,5-b]pyridin-2-yl)methanol 19-5

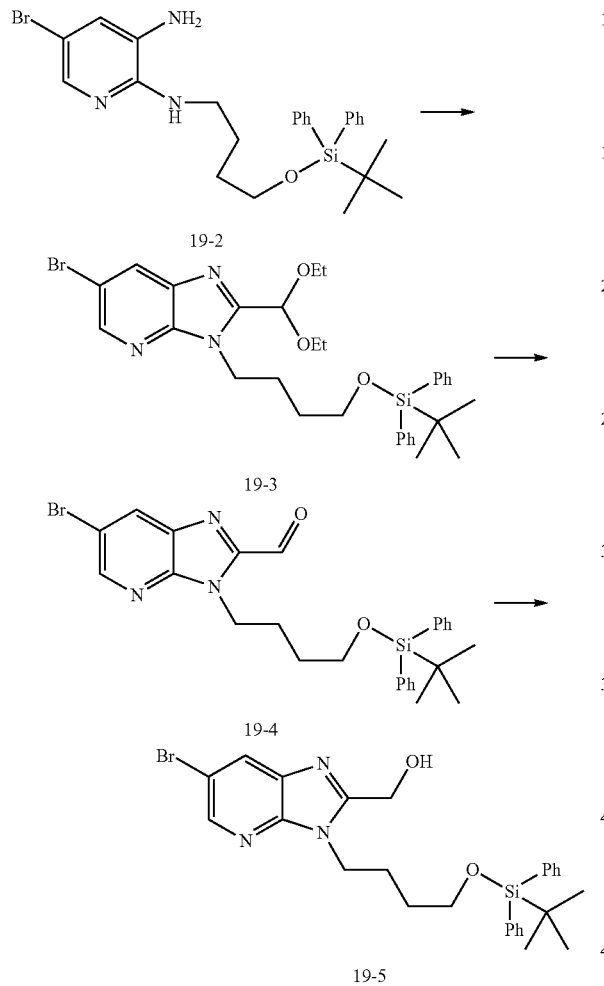

Intermediate 19-5 was prepared in the same manner as intermediate 10-5 in 3 steps synthesis starting from intermediate 19-2

Step 6: Synthesis of 3-((6-bromo-3-(4-(tert-butyldiphenylsilyloxy)butyl)-3H-imidazo[4,5-b]pyridin-2-yl)methyl)-1-cyclopropyl-1H-imidazo[4,5-c]pyridin-2(3H)-one 19-6

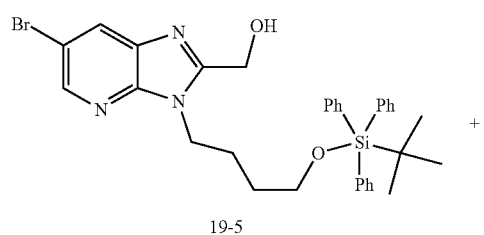

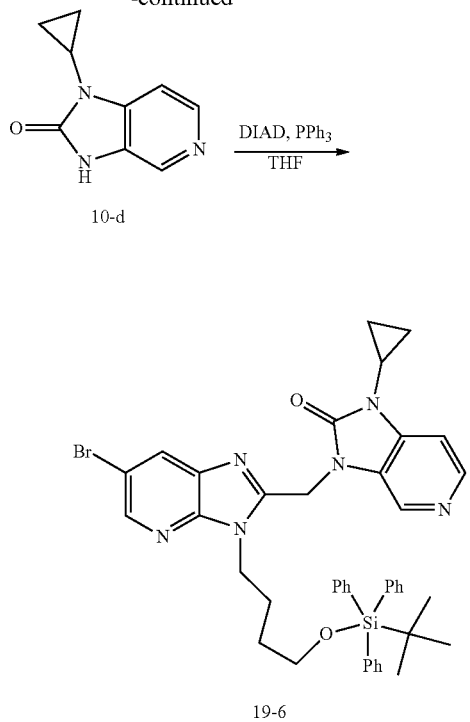

The intermediate 19-6 was prepared in the same manner as compound 10 using intermediates 19-5 and 10-d as starting material m/z=696 (M+H)$^+$.

$^1$H NMR (400 MHz, CHLOROFORM-d) δ ppm 0.94-1.05 (m, 11 H), 1.13-1.21 (m, 2 H), 1.51-1.58 (m, 2 H), 1.73-1.91 (m, 2 H), 2.87 (tdd, J=6.9, 6.9, 3.8, 3.5 Hz, 1 H), 3.63 (t, J=6.1 Hz, 2 H), 4.42 (t, J=7.5 Hz, 2 H), 5.31 (s, 2 H), 7.09 (dd, J=5.3, 0.5 Hz, 1 H), 7.30-7.36 (m, 4 H), 7.38 (m, J=7.3 Hz, 2 H), 7.55-7.65 (m, 4 H), 8.15 (d, J=2.0 Hz, 1 H), 8.33 (d, J=5.3 Hz, 1 H), 8.38 (d, J=2.3 Hz, 1 H), 8.58 (s, 1 H)

Step 7: Synthesis of 3-((6-bromo-3-(4-hydroxybutyl)-3H-imidazo[4,5-b]pyridin-2-yl)methyl)-1-cyclopropyl-1H-imidazo[4,5-c]pyridin-2(3H)-one 19

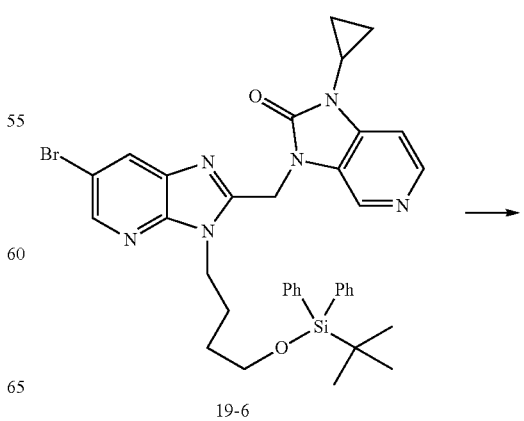

-continued

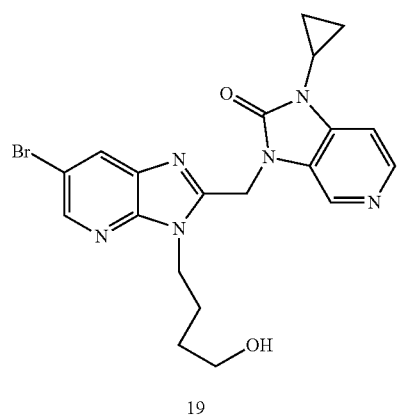

19

The intermediate 19-6 (1.65 g, 2.32 mmol) was dissolved in methanol (40 mL), then ammonium fluoride (0.206 g, 5.58 mmol) was added. The resulting mixture was stirred at reflux for 56 hours. The reaction mixture was allowed to cool down to room temperature, then the solvent was removed. The residue was purified by column chromatography using dichloromethane/methanol to yield the product as a white solid (1 g, 92%). m/z=458 (M+H)$^+$.

$^1$H NMR (400 MHz, DMSO-d$_6$) δ ppm 0.87-0.96 (m, 2 H), 1.07 (m, J=2.0 Hz, 2 H), 1.37-1.51 (m, 2 H), 1.69-1.83 (m, 2 H), 3.00 (tdd, J=7.0, 7.0, 3.6, 3.5 Hz, 1 H), 3.35-3.44 (m, 2 H), 4.37 (t, J=7.5 Hz, 2 H), 4.44 (t, J=5.1 Hz, 1 H), 5.45 (s, 2 H), 7.29 (dd, J=5.3, 0.8 Hz, 1 H), 8.26 (d, J=5.3 Hz, 1 H), 8.32 (d, J=2.0 Hz, 1 H), 8.37 (d, J=0.5 Hz, 1 H), 8.44 (d, J=2.0 Hz, 1 H)

EXAMPLE 27

Synthesis of 3-((6-bromo-3-(4-hydroxybutyl)-3H-imidazo[4,5-b]pyridin-2-yl)methyl)-1-(oxetan-3-yl)-1H-imidazo[4,5-c]pyridin-2(3H)-one 20

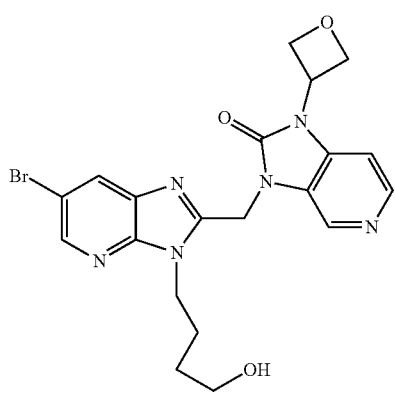

20

Step 1: Synthesis of 3-((6-bromo-3-(4-(tert-butyl-diphenylsilyloxy)butyl)-3H-imidazo[4,5-b]pyridin-2-yl)methyl)-1-(oxetan-3-yl)-1H-imidazo[4,5-c]pyridin-2(3H)-one 20-1

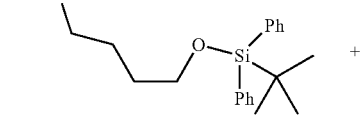

19-5

+

[structure]

11-d

→ DIAD, PPh$_3$ / THF

[structure]

20-1

Intermediate 20-1 was prepared in the same manner as intermediate 19-6 using intermediates 19-5 and 11-d as starting material. m/z=712 (M+H)$^+$.

$^1$H NMR (400 MHz, CHLOROFORM-d) δ ppm 1.01 (s, 9 H), 1.56 (s, 2 H), 1.86 (m, J=7.6, 7.6, 7.6, 7.6 Hz, 2 H), 3.64 (t, J=6.1 Hz, 2 H), 4.40 (t, J=7.4 Hz, 2 H), 5.03-5.13 (m, 4 H), 5.33 (s, 2 H), 5.51-5.63 (m, 1 H), 7.31-7.37 (m, 4 H), 7.39 (d, J=7.0 Hz, 2 H), 7.54-7.58 (m, 1 H), 7.61 (dd, J=8.0, 1.5 Hz, 4 H), 8.15 (d, J=2.0 Hz, 1 H), 8.39 (d, J=2.0 Hz, 1 H), 8.41 (d, J=5.3 Hz, 1 H), 8.66 (s, 1 H)

Step 2: Synthesis of 3-((6-bromo-3-(4-hydroxybutyl)-3H-imidazo[4,5-b]pyridin-2-yl)methyl)-1-(oxetan-3-yl)-1H-imidazo[4,5-c]pyridin-2(3H)-one 20

Step 1: Synthesis of 3-((3-(4-(tert-butyldiphenylsilyloxy)butyl)-6-chloro-3H-imidazo[4,5-b]pyridin-2-yl)methyl)-1-cyclopropyl-1H-imidazo[4,5-c]pyridin-2(3H)-one 21-2

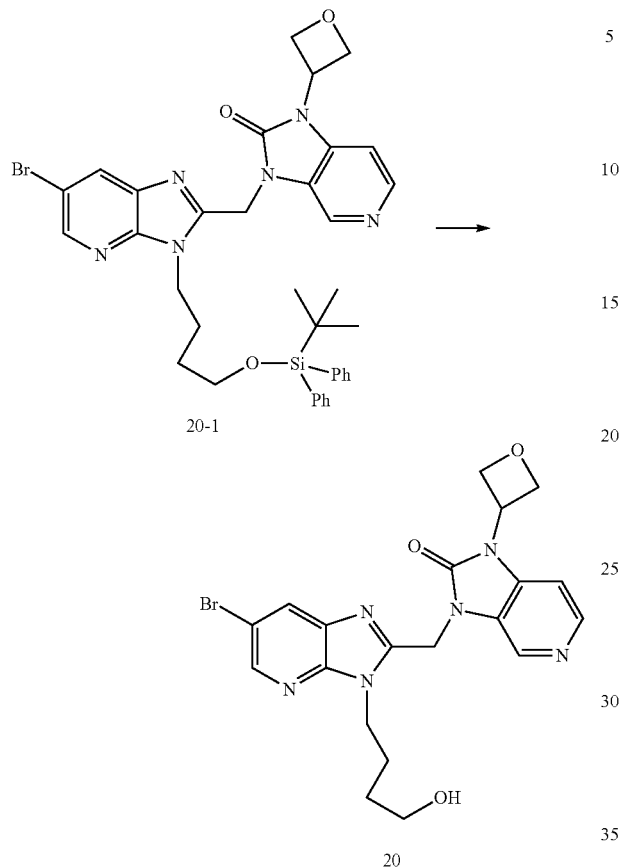

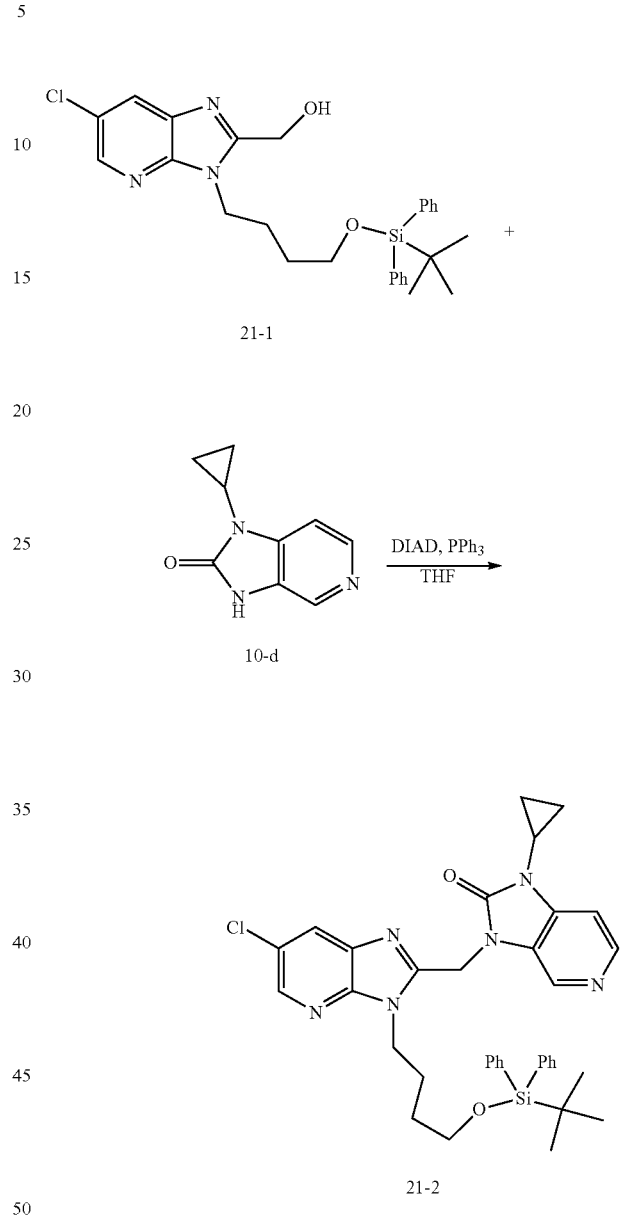

Compound 20 was prepared in the same manner as compound 19 using intermediates 20-1 as starting material m/z=474 (M+H)+.

$^1$H NMR (400 MHz, CHLOROFORM-d) δ ppm 1.56-1.67 (m, 2 H), 1.86 (qd, J=7.6, 7.4 Hz, 2 H), 2.22 (br. s, 1 H), 3.69 (t, J=6.0 Hz, 2 H), 4.38-4.51 (m, 2 H), 5.04-5.21 (m, 4 H), 5.40 (s, 2 H), 5.62 (tt, J=7.7, 5.8 Hz, 1 H), 7.61 (dd, J=5.4, 0.6 Hz, 1 H), 8.16 (d, J=2.3 Hz, 1 H), 8.32-8.49 (m, 2 H), 8.73 (d, J=0.5 Hz, 1 H)

EXAMPLE 28

Synthesis of 3-((6-chloro-3-(4-hydroxybutyl)-3H-imidazo[4,5-b]pyridin-2-yl)methyl)-1-cyclopropyl-1H-imidazo[4,5-c]pyridin-2(3H)-one 21

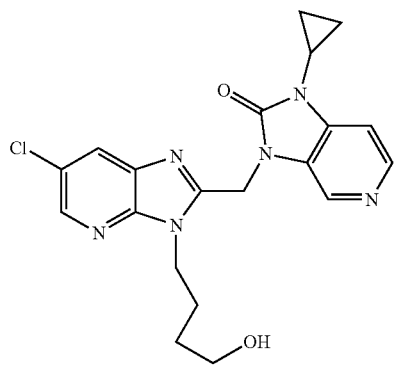

Intermediate 21-1 was prepared in the same manner as intermediate 19-5 in 5 steps synthesis using 2,5-dichloro-3-nitropyridine (CAS 21427-62-3) as starting material. Intermediate 21-2 was prepared in the same manner as intermediate 19-6 using intermediates 21-1 and 10-d as starting material m/z=652 (M+H)+.

$^1$H NMR (400 MHz, CHLOROFORM-d) δ ppm 0.97-1.04 (m, 1 H), 1.13-1.21 (m, 2 H), 1.46-1.64 (m, 2 H), 1.82-1.91 (m, 2 H), 2.88 (tdd, J=7.0, 7.0, 3.6, 3.5 Hz, 1 H), 3.63 (t, J=6.1 Hz, 2 H), 4.43 (t, J=7.4 Hz, 2 H), 5.31 (s, 2 H), 7.09 (d, J=5.3 Hz, 1 H), 7.29-7.36 (m, 4 H), 7.38 (m, J=7.3 Hz, 2 H), 7.60 (dd, J=7.9, 1.4 Hz, 4 H), 8.00 (d, J=2.0 Hz, 1 H), 8.30 (d, J=2.0 Hz, 1 H), 8.33 (d, J=5.3 Hz, 1 H), 8.59 (s, 1 H)

Step 2: Synthesis of 3-((6-chloro-3-(4-hydroxybutyl)-3H-imidazo[4,5-b]pyridin-2-yl)methyl)-1-cyclopropyl-1H-imidazo[4,5-c]pyridin-2(3H)-one 21

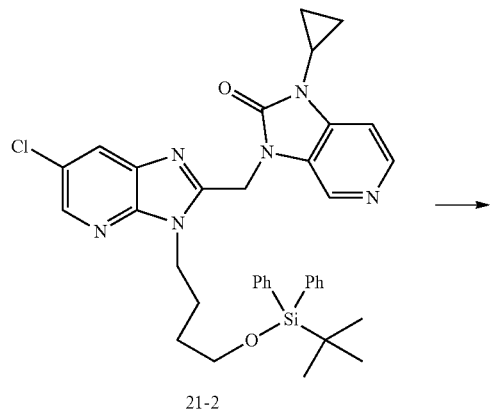

21-2

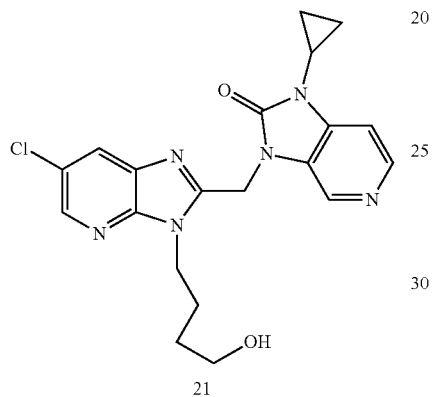

21

Compound 21 was prepared in the same manner as compound 19 using intermediates 21-2 as starting material. m/z=414 (M+H)$^+$.

$^1$H NMR (400 MHz, CHLOROFORM-d) δ ppm 0.98-1.06 (m, 2 H), 1.17-1.21 (m, 2 H), 1.64-1.68 (m, 2 H), 1.84-1.91 (m, 2 H), 2.36-2.41 (m, 1 H), 2.95-3.01 (tdd, J=7.0, 7.0, 3.6, 3.5 Hz, 1 H), 3.71 (q, J=5.9 Hz, 2 H), 4.41-4.50 (m, 2 H), 5.37 (s, 2H), 7.15 (dd, J=5.3, 0.8 Hz, 1 H), 8.02 (d, J=2.0 Hz, 1 H), 8.32 (d, J=2.0 Hz, 1 H), 8.35 (d, J=5.3 Hz, 1 H), 8.66 (d, J=0.8 Hz, 1 H)

EXAMPLE 29

Synthesis of 1-cyclopropyl-3-((6-fluoro-3-(4-hydroxybutyl)-3H-imidazo[4,5-b]pyridin-2-yl)methyl)-1H-imidazo[4,5-c]pyridin-2(3H)-one 22

22

Step 1: Synthesis of 5-fluoro-3-nitropyridin-2-yl 4-methylbenzenesulfonate 22-1

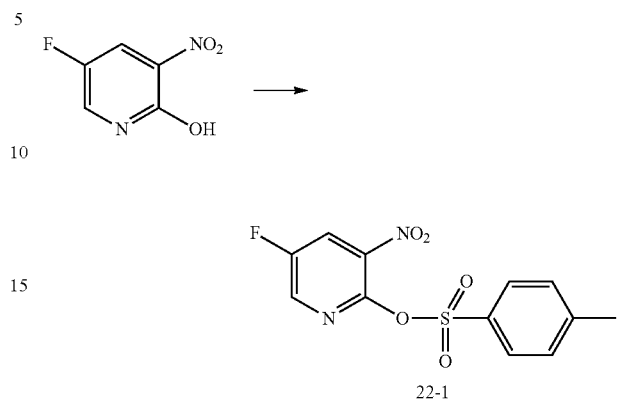

22-1

To a mixture of 5-fluoro-3-nitropyridin-2-ol (24.2 g, 153 mmol, CAS 136888-20-3), tosyl-chloride (33.4 g, 176 mmol) in dichloromethane (1000 mL) was added at room temperature, under nitrogen atmosphere, triethyl amine (44 mL, 304 mmol). At the end of the addition, DMAP (3.7 g, 30 mmol) was added. The resulting mixture was stirred at 25° C. for 16 h. Dichloromethane (500 mL) was added and the mixture was successively washed with an aqueous solution 1N of hydrochloric acid (2×500 mL) and brine (500 mL). The separated aqueous layer was extracted with CH$_2$Cl$_2$ (400 mL). The combined organic layers were dried over Na$_2$SO$_4$ and filtered through a silica pad (50 g). The filtrate was purified by flash chromatography (eluent: CH$_2$Cl$_2$) to give intermediate 22-1 (34 g, 67%).

Step 2: Synthesis of N-(4-(tert-butyldiphenylsilyloxy)butyl)-5-fluoro-3-nitropyridin-2-amine 22-2

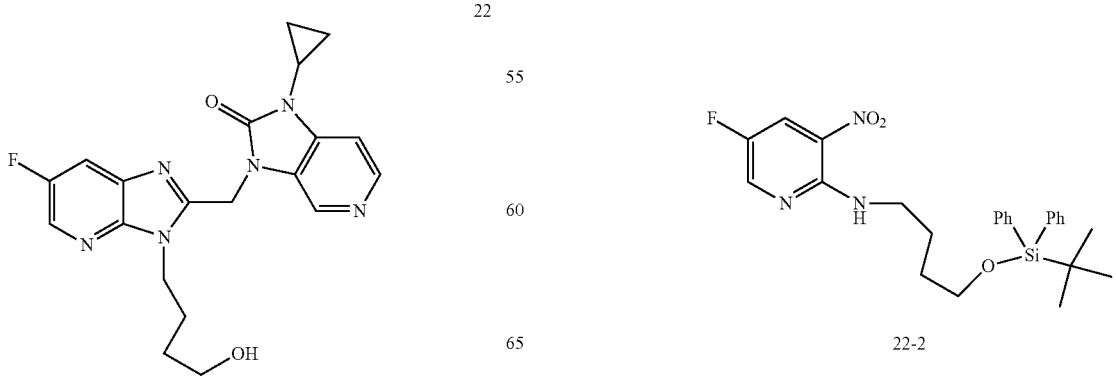

22-2

Intermediate 22-2 was prepared in the same manner as intermediate 19-1 using intermediates 22-1 and 8-b as starting material Steps 3,4,5,6 and 7: synthesis of 3-((3-(4-(tert-butyl-diphenylsilyloxy)butyl)-6-fluoro-3H-imidazo[4,5-b]pyridin-2-yl)methyl)-1-cyclopropyl-1H-imidazo[4,5-c]pyridin-2(3H)-one 22-7

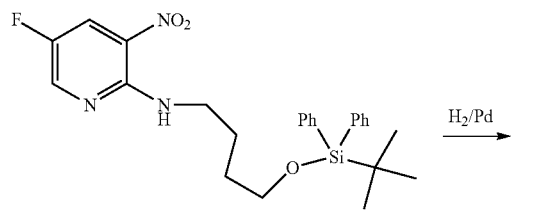

22-2

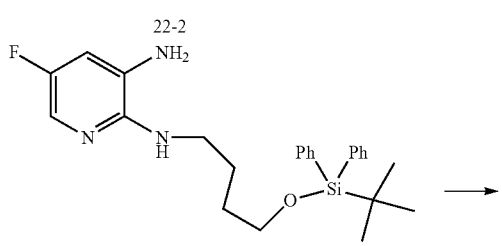

22-3

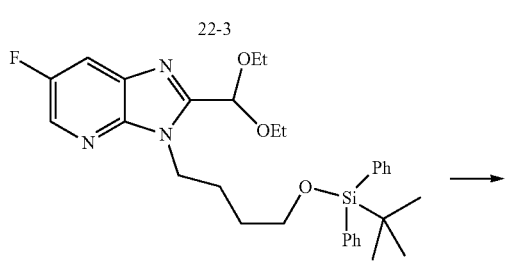

22-4

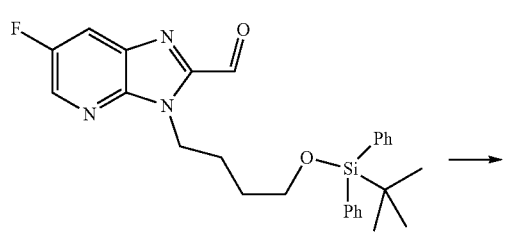

22-5

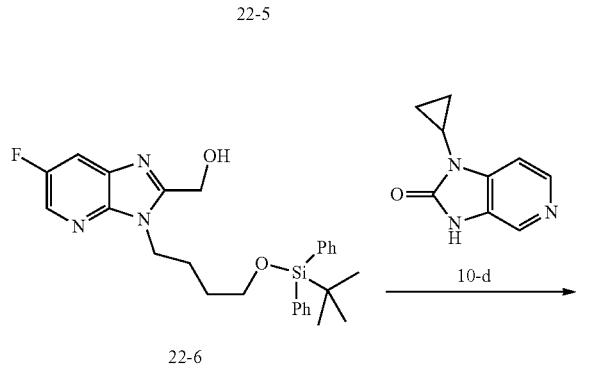

22-6

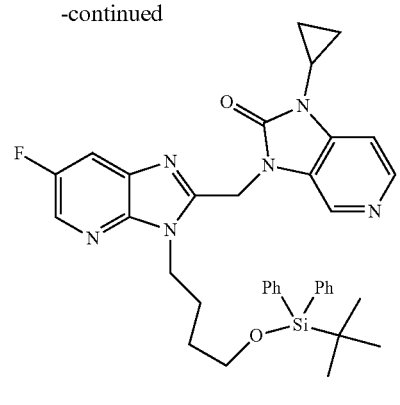

22-7

Intermediate 22-7 was prepared in the same manner as intermediate 19-5 in 5 steps synthesis using intermediate 22-2 as starting material. m/z=635 (M+H)+. $^1$H NMR (400 MHz, CHLOROFORM-d) δ ppm 0.95-1.12 (m, 2H), 1.00 (s, 9 H), 1.09-1.17 (m, 2 H), 1.52-1.64 (m, 2 H), 1.76-1.89 (m, 2 H), 2.88 (tdd, J=7.0, 7.0, 3.6, 3.5 Hz, 1H), 3.64 (t, J=6.3 Hz, 2 H), 4.43 (t, J=7.4 Hz, 2 H), 5.31 (s, 2 H), 7.09 (dd, J=5.3, 0.8 Hz, 1 H), 7.30-7.42 (m, 6 H), 7.58-7.64 (m, 4 H), 7.72 (dd, J=8.7, 2.6 Hz, 1 H), 8.24 (dd, J=2.5, 1.8 Hz, 1 H) 8.33 (d, J=5.3 Hz, 1 H), 8.60 (s, 1 H)

Step 8: Synthesis of 1-cyclopropyl-3-((6-fluoro-3-(4-hydroxybutyl)-3H-imidazo[4,5-b]pyridin-2-yl)methyl)-1H-imidazo[4,5-c]pyridin-2(3H)-one 22

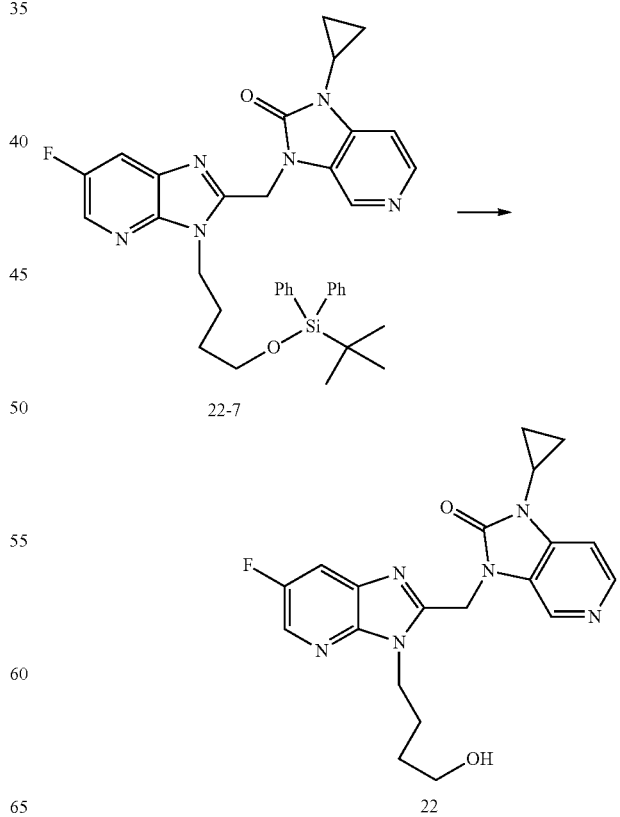

Compound 22 was prepared in the same manner as compound 19 using intermediate 22-7 as starting material. m/z=397 (M+H)+.

$^1$H NMR (400 MHz, CHLOROFORM-d) δ ppm 0.99-1.07 (m, 2 H), 1.14-1.21 (m, 2 H), 1.65 (quin, J=6.6 Hz, 2 H), 1.85 (qd, J=7.5, 7.3 Hz, 2 H), 2.48 (t, J=5.3 Hz, 1 H), 2.95 (tdd, J=7.0, 7.0, 3.6, 3.5 Hz, 1 H), 3.71 (m, J=4.0 Hz, 2 H), 4.41-4.51 (m, 2 H), 5.37 (s, 2 H), 7.15 (dd, J=5.3, 0.8 Hz, 1 H), 7.74 (dd, J=8.5, 2.5 Hz, 1 H), 8.26 (dd, J=2.5, 1.8 Hz, 1 H), 8.34 (d, J=5.5 Hz, 1 H), 8.66 (d, J=0.5 Hz, 1 H)

EXAMPLE 30

Synthesis of 4-chloro-3-((3-isopentyl-3H-imidazo[4,5-b]pyridin-2-yl)methyl)-1-isopropyl-1H-imidazo[4,5-c]pyridin-2(3H)-one 25

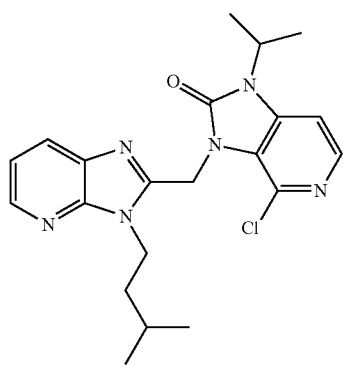

Step 1: Synthesis of N-isopentyl-3-nitropyridin-2-amine 25-1

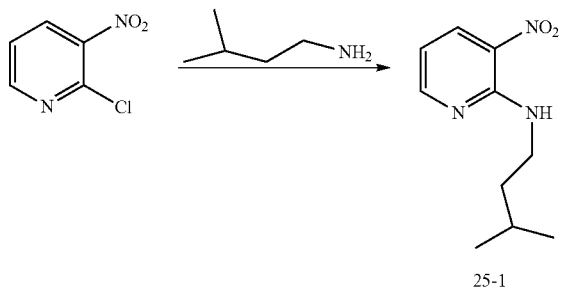

Intermediate 25-1 was prepared in the same manner as intermediate 7-1 using the commercially available 2-chloro-3-nitropyridine (CAS 5470-18-8) and isopentylamine (CAS 107-85-7). m/z=210 (M+H)+.

Step 2: Synthesis of N²-isopentylpyridine-2,3-diamine 25-2

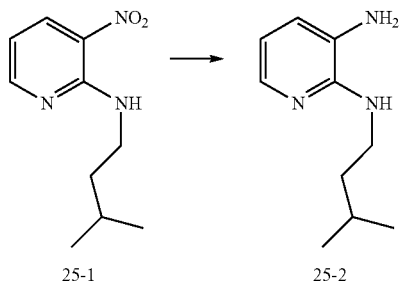

Intermediate 25-2 was prepared in the same manner as intermediate 7-2 using intermediates 25-1 as starting material m/z=178 (M+H)+.

Step 3: Synthesis of 3-isopentyl-2-(trichloromethyl)-3H-imidazo[4,5-b]pyridine 25-3

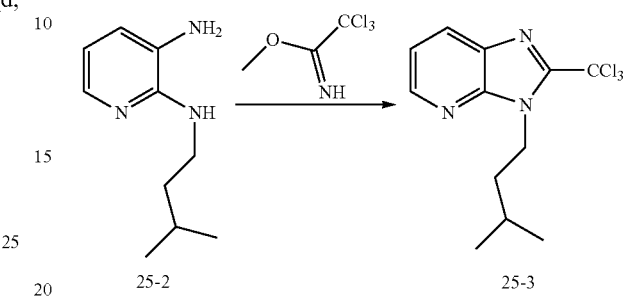

Intermediate 25-2 (17.5 g, 97.6 mmol) was dissolved in acetic acid (220 mL). To the resulting mixture methyl 2,2,2-trichloroacetimidate (CAS 2533-69-9) (12.13 mL, 97.6 mmol) was added at once. The resulting mixture was stirred at 50° C. for 48 h. The mixture was allowed to cool to room temperature and poured onto ice/water solution. The pH was adjusted to pH=5 by addition of sodium carbonate. The resulting mixture was extracted with dichloromethane (3×100 mL). The combined organic layers were successively washed with saturated NaHCO$_3$, dried over MgSO$_4$ and evaporated. The residue was purified by column chromatography using CH$_2$Cl$_2$ to CH$_2$Cl$_2$/EtOAc as the eluent to give an oil which solidified on drying in vacuo (23 g, 77%). m/z=307 (M+H)+.

Step 4: Synthesis of methyl 3-isopentyl-3H-imidazo[4,5-b]pyridine-2-carboxylate 25-4

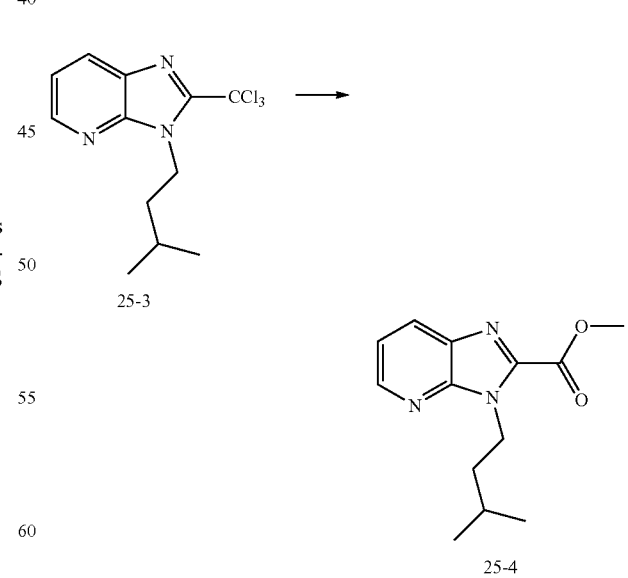

Intermediate 25-3 (20 g, 65.22 mmol) was dissolved in MeOH (400 mL) and sodium carbonate (6.9 g, 65.22 mmol) was added. The resulting mixture was stirred at room temperature for 1 hour and sodium methanolate (25%, 6 mL, 26.1 mmmol) was added. The resulting mixture was refluxed for 48 hours. The mixture was allowed to cool to room temperature and filtered. The filtrate was evaporated to dryness. The residue was purified by column chromatography using CH₂Cl₂ to CH₂Cl₂/EtOAc 1/1 as the eluent. After evaporation intermediate 25-4 was isolated as a white powder (9.52 g, 59%). m/z=248 (M+H)⁺.

Step 5: Synthesis of (3-isopentyl-3H-imidazo[4,5-b]pyridin-2-yl)methanol 25-5

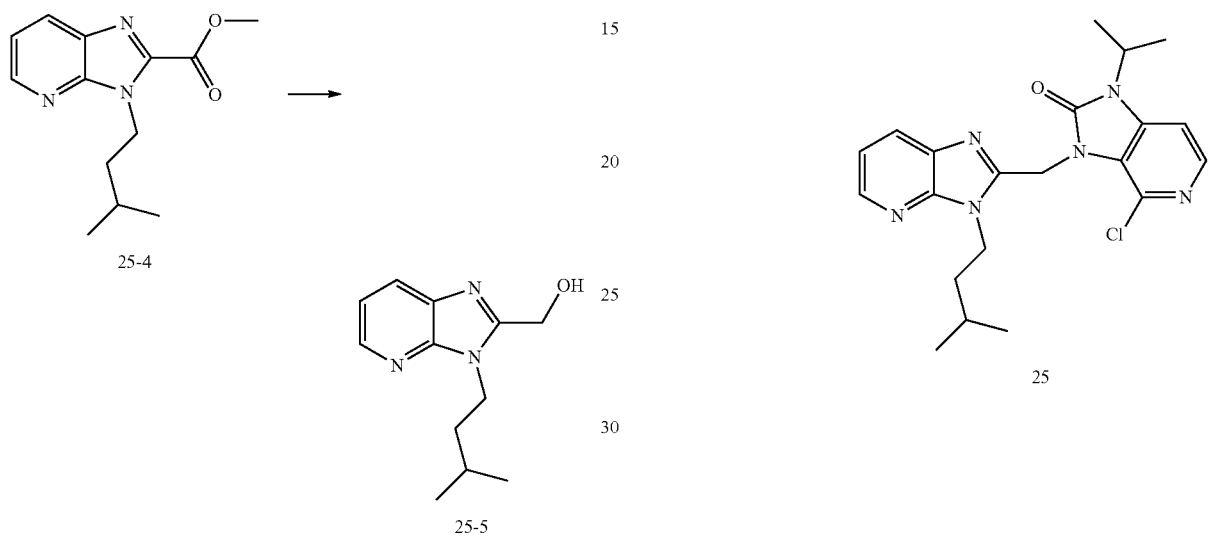

Intermediate 25-4 (9.52 g, 38.5 mmol) was dissolved in dry THF (125 mL). The mixture was cooled to 0° C. in an ice-bath. Lithium aluminum hydride (1.46 g, 38.5 mmol) was added portion wise. The resulting mixture was stirred at 0° C. for 10 minutes and then at room temperature overnight. A solution of saturated NaHCO₃ (10 mL) was added dropwise to the reaction mixture. The resulting mixture was stirred at room temperature for 1 h. Then EtOAc (200 mL) was added. The organic layer was then washed with water (100 mL) dried over MgSO₄ and evaporated. The residue was purified by column chromatography using EtOAc/MeOH/NH₃ 9/1 as the eluent. After evaporation intermediate 25-5 was isolated as a white powder (0.58 g, 7%). m/z=220 (M+H)⁺.

Step 6: Synthesis of 4-chloro-3-((3-isopentyl-3H-imidazo[4,5-b]pyridin-2-yl)methyl)-1-isopropyl-1H-imidazo[4,5-c]pyridin-2(3H)-one 25

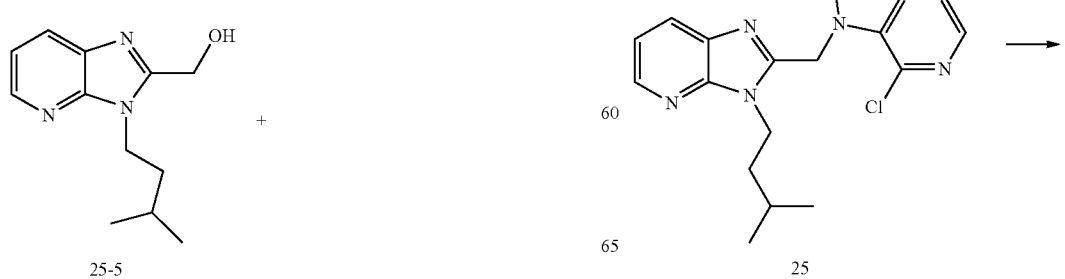

Compound 25 was prepared in the same manner as compound 10 using intermediates 25-5 and 14-d as starting material m/z=414 (M+H)⁺.

¹H NMR (400 MHz, CHLOROFORM-d) δ ppm 1.04 (d, J=6.4 Hz, 6 H), 1.59 (d, J=7.0 Hz, 6 H), 1.68-1.85 (m, 3 H), 4.37-4.44 (m, 2 H), 4.76 (spt, J=7.1 Hz, 1 H), 5.66 (s, 2 H), 7.10 (d, J=5.5 Hz, 1 H), 7.15 (dd, J=8.0, 4.7 Hz, 1 H), 7.88 (dd, J=8.0, 1.6 Hz, 1 H), 8.09 (d, J=5.5 Hz, 1 H), 8.34 (dd, J=4.8, 1.5 Hz, 1 H)

Synthesis of 3-((3-isopentyl-3H-imidazo[4,5-b]pyridin-2-yl)methyl)-1-isopropyl-2-oxo-2,3-dihydro-1H-imidazo[4,5-c]pyridine-4-carbonitrile 29

-continued

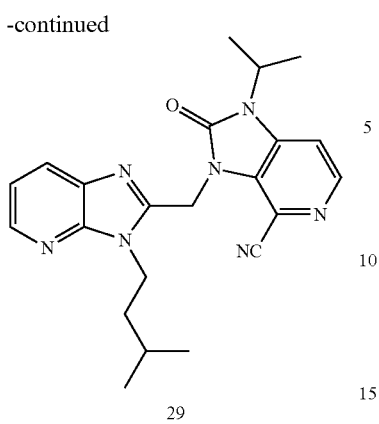
29

The mixture of compound 25 (0.075 g, 0.182 mmol), tetrakis(triphenyl-phosphine)palladium (41 mg, 0.036 mmol) and dicyanozinc (0.042 g, 0.363 mmol) in DMF (3 mL) under nitrogen atmosphere was irradiated for 30 minutes in a microwave reactor at 170° C. The resulting mixture was allowed to cool down to room temperature then filtered through an acrodisk filter and evaporated to dryness. The residue was purified by column chromatography using EtOAc. The title compound 29 was isolated as a white solid (60 mg, 81%).
m/z=404 (M+H)$^+$.

$^1$H NMR (400 MHz, DMSO-d$_6$) δ ppm 1.00 (d, J=6.6 Hz, 6 H), 1.52 (d, J=7.0 Hz, 6H), 1.68 (spt, J=6.6 Hz, 1 H), 1.74-1.83 (m, 2 H), 4.38-4.46 (m, 2 H), 4.74 (spt, J=7.2 Hz, 1 H), 5.71 (s, 2 H), 7.23 (dd, J=8.0, 4.7 Hz, 1 H), 7.81 (d, J=5.3 Hz, 1 H), 7.94 (dd, J=8.0, 1.6 Hz, 1 H), 8.34 (dd, J=4.9, 1.4 Hz, 1 H), 8.37 (d, J=5.3 Hz, 1 H)

EXAMPLE 31

Synthesis of 1-cyclopropyl-3-((1-isopentyl-1H-imidazo[4,5-c]pyridin-2-yl)methyl-1H-imidazo[4,5-c]pyridin-2(3H)-one 33

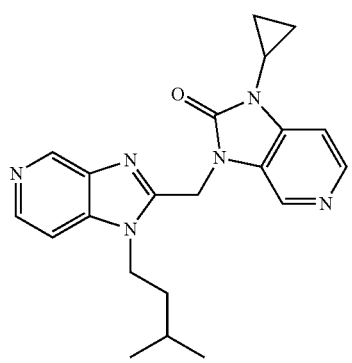
33

Compound 33 was prepared in the same manner as compound 7 using 4-chloro-3-nitropyridine (CAS 13091-23-1) and isopentylamine (CAS 107-85-7) as starting material. m/z=377 (M+H)$^+$.

$^1$H NMR (400 MHz, CHLOROFORM-d) δ ppm 0.99 (d, J=6.6 Hz, 6 H), 1.00-1.05 (m, 2 H), 1.13-1.23 (m, 2 H), 1.44-1.55 (m, 1 H), 1.65-1.78 (m, 1 H), 2.86-2.98 (m, 1 H), 4.28-4.36 (m, 2 H), 5.38 (s, 2 H), 7.14 (dd, J=5.4, 0.7 Hz, 1 H), 7.25 (d, J=1.2 Hz, 1 H), 8.34 (d, J=5.3 Hz, 1 H), 8.43 (d, J=5.7 Hz, 1 H), 8.64 (s, 1 H), 9.08 (d, J=1.0 Hz, 1 H)

EXAMPLE 32

Synthesis of 1-cyclopropyl-3-((1-isopentyl-1H-imidazo[4,5-c]pyridin-2-yl)methyl-1H-benzo[d]imidazol-2(3H)-one 31

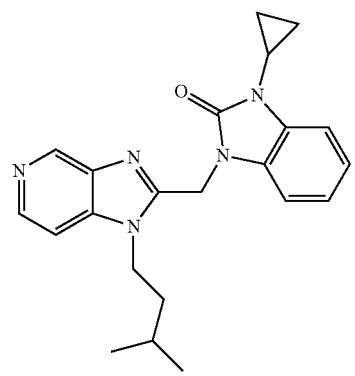
31

Compound 31 was prepared in the same manner as compound 33 using intermediate 13-d as starting material in the last step. m/z=376 (M+H)$^+$.

$^1$H NMR (400 MHz, CHLOROFORM-d) δ ppm 0.96 (d, J=6.5 Hz, 6 H), 0.99-1.07 (m, 2 H), 1.08-1.20 (m, 2 H), 1.37-1.48 (m, 2 H), 1.68 (dquin, J=13.3, 6.7, 6.7, 6.7, 6.7 Hz, 1 H), 2.90 (tdd, J=6.9, 6.9, 3.8, 3.5 Hz, 1 H), 4.25-4.41 (m, 2 H), 5.37 (s, 2 H), 7.07-7.15 (m, 2 H), 7.16-7.23 (m, 1 H), 7.25 (dd, J=5.8, 1.0 Hz, 1 H), 7.32-7.43 (m, 1 H), 8.41 (d, J=5.8 Hz, 1 H), 9.09 (d, J=0.8 Hz, 1 H)

EXAMPLE 33

Synthesis of 1-cyclopropyl-5-fluoro-3-((1-isopentyl-1H-imidazo[4,5-c]pyridin-2-yl)methyl-1H-benzo[d]imidazol-2(3H)-one 32

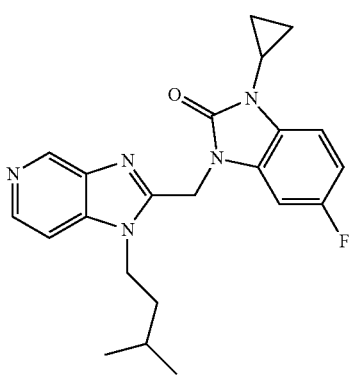
32

Compound 32 was prepared in the same manner as compound 33 using intermediate 12-d as starting material in the last step. m/z=394 (M+H)$^+$.

$^1$H NMR (400 MHz, CHLOROFORM-d) δ ppm 0.97 (d, J=6.5 Hz, 6 H), 1.00-1.05 (m, 2 H), 1.10-1.17 (m, 2 H), 1.40-1.50 (m, 2 H), 1.70-1.73 (m, 1 H), 2.88-3.02 (m, 1 H), 4.29-4.39 (m, 2 H), 5.33 (s, 2 H), 6.74-6.84 (m, 1 H), 7.09 (dd, J=8.5, 4.5 Hz, 1 H), 7.19 (dd, J=8.5, 2.3 Hz, 1 H), 7.24-7.27 (m, 1 H), 8.42 (d, J=5.5 Hz, 1 H), 9.10 (s, 1 H)

EXAMPLE 34

Synthesis of 3-((1-isopentyl-1H-imidazo[4,5-c]pyridin-2-yl)methyl-1-(oxetan-3-yl)-1H-imidazo[4,5-c]pyridin-2(3H)-one 36

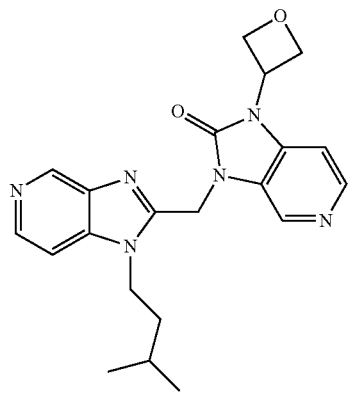

36

Compound 36 was prepared in the same manner as compound 33 using intermediate 11-d as starting material in the last step. m/z=393 (M+H)+.

Synthesis of 3-((1-(4-benzyloxy)butyl)-4-chloro-1H-imidazo[4,5-c]pyridin-2-yl)methyl-1-cyclopropyl-1H-imidazo[4,5-c]pyridin-2(3H)-one 38

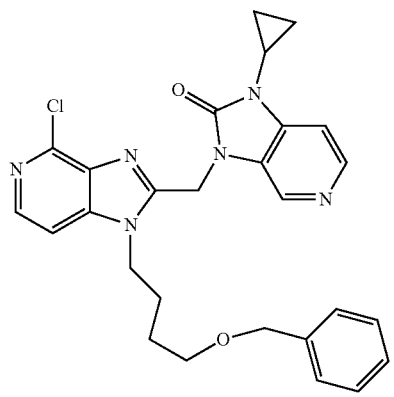

38

Step 1: Synthesis of 1-(4-benzyloxy)butyl)-4-chloro-2-(diethoxymethyl)-1H-imidazo[4,5-c]pyridine 38-2

Intermediate 38-1 was prepared in the same manner as intermediate 10-3 in a three step synthesis using 2,4-dichloro-3-nitropyridine (CAS 5975-12-2) and 4-aminobutan-1-ol (CAS 13325-10-5) as starting material.

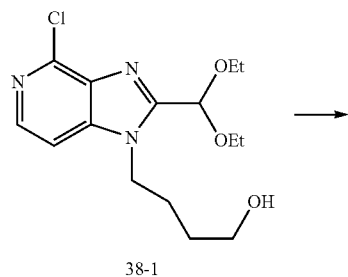

38-1

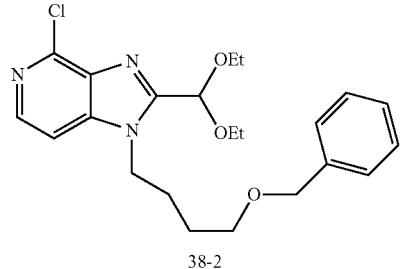

38-2

To a solution of intermediate 38-1 (8.05 g, 24.55 mmol) in dry THF (100 mL). stirred and cooled at 0° C. were added benzyl bromide (3.06 mL, 25.8 mmol), tetrabutyl ammonium iodide (90.7 mg, 0.24 mmol). To the resulting mixture sodium hydride (1.08 g, 27.02 mmol) was added portionwise. The resulting mixture was stirred at room temperature overnight. The solvent was removed and the residue was dissolved in dichloromethane (200 mL). The resulting mixture was poured in ice/water and stirred for 10 minutes. The organic layer was separated and the aqueous layer was extracted with dichloromethane (2×100 mL). The combined organic layers were dried over Na$_2$SO$_4$ and evaporated. The residue was purified by column chromatography using EtOAc. The title intermediate 38-2 was isolated as a yellow oil (8.75 g, 85%). m/z=419 (M+H)+.

Compound 38 was prepared in the same manner as compound 10 in a 3 step synthesis using intermediate 38-2 as starting material. m/z=504 (M+H)+.

$^1$H NMR (400 MHz, CHLOROFORM-d) δ ppm 0.94-1.02 (m, 2 H), 1.13-1.21 (m, 2 H), 1.59-1.76 (m, 4 H), 2.88 (tdd, J=7.0, 7.0, 3.6, 3.5 Hz, 1 H), 3.45 (t, J=5.5 Hz, 2 H), 4.35 (t, J=7.4 Hz, 2 H), 4.44 (s, 2 H), 5.40 (s, 2 H), 7.01-7.09 (m, 1 H), 7.18 (d, J=5.8 Hz, 1 H), 7.22-7.37 (m, 5 H), 8.15 (d, J=5.8 Hz, 1 H), 8.33 (d, J=5.3 Hz, 1 H), 8.68 (d, J=0.5 Hz, 1 H)

EXAMPLE 35

Synthesis of 1-cyclopropyl-3-((1-(4-hydroxybutyl)-1H-imidazo[4,5-c]pyridin-2-yl)methyl-1H-imidazo[4,5-c]pyridin-2(3H)-one 35

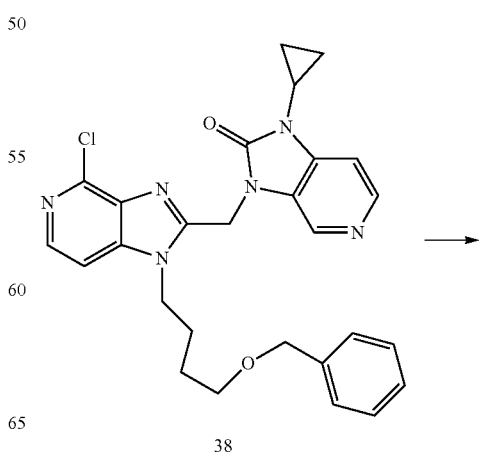

38

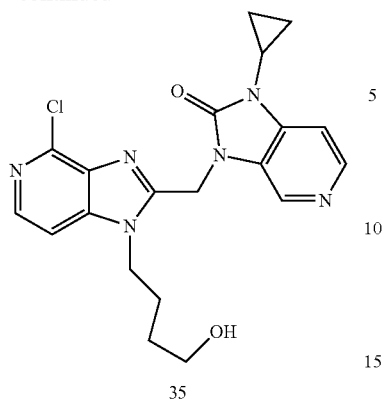

35

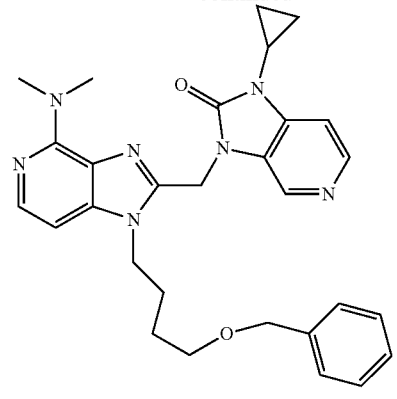

37-1

To intermediate 38 (0.5 g, 0.99 mmol) in methanol (100 mL), potassium acetate (0.146 g, 1.5 mmol) and wet 10% Pd/C (0.2 g) were added. The reaction mixture was stirred at 25° C. under hydrogen atmosphere. After uptake of $H_2$ (1 eq), the catalyst was filtered off and the filtrate was evaporated. The residue was dissolved in water and dichloromethane. The resulting mixture was successively extracted with dichloromethane, dried over $MgSO_4$ and concentrated. The residue was purified by column chromatography using dichloromethane/methanol. The title compound 35 was collected as a white powder (125 mg, 31%). m/z=379 $(M+H)^+$. $^1H$ NMR (400 MHz, DMSO-$d_6$) δ ppm 0.86-0.99 (m, 2 H), 1.08 (m, J=5.3 Hz, 2 H), 1.37-1.54 (m, 2 H), 1.71 (ddd, J=14.6, 7.7, 7.4 Hz, 2 H), 3.01 (tt, J=6.9, 3.2 Hz, 1 H), 3.37-3.48 (m, 2 H), 4.38 (t, J=7.4 Hz, 2 H), 4.48 (t, J=5.0 Hz, 1 H), 5.45 (s, 2 H), 7.29 (d, J=5.3 Hz, 1 H), 7.66 (d, J=5.5 Hz, 1 H), 8.26 (d, J=5.3 Hz, 1 H), 8.34 (d, J=5.5 Hz, 1 H), 8.39 (s, 1 H), 8.87 (s, 1 H)

EXAMPLE 36

Synthesis of 1-cyclopropyl-3-((4-(dimethylamino)-1-(4-hydroxybutyl)-1H-imidazo[4,5-c]pyridin-2-yl) methyl-1H-imidazo[4,5-c]pyridin-2(3H)-one 37

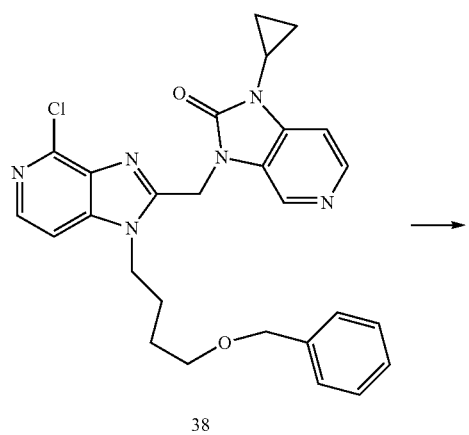

38

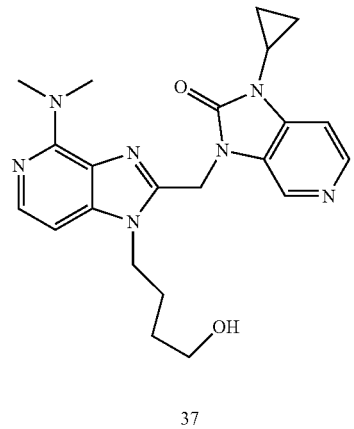

37

Compound 38 (0.5 g, 0.99 mmol) was put in a microwave tube and dimethyl amine (2M solution in MeOH, 10 mL) was added. The resulting mixture was heated to 125° C. in a microwave oven for 4 hours. The reaction mixture was allowed to cool to room temperature then evaporated to dryness. The residue (510 mg) containing the intermediate 37-1 was dissolved in methanol (50 mL) and potassium acetate (0.195 g, 1.99 mmol) and wet 10% Pd/C (0.2 g) were added. The reaction mixture was stirred at 50° C. under hydrogen atmosphere for 48 hours. After uptake of $H_2$ (1 eq), the catalyst was filtered off and the filtrate was evaporated. The residue was dissolved in a mixture of water and dichloromethane. The resulting mixture was successively extracted with dichloromethane, dried over $MgSO_4$ and concentrated. The residu was purified by column chromatography using dichloromethane/methanol. The title compound 37 was collected as a white powder (140 mg, 32%). m/z=422 $(M+H)^+$.

$^1H$ NMR (400 MHz, DMSO-$d_6$) δ ppm 0.86-0.93 (m, 2 H), 1.07-1.12 (m, 2 H), 1.33-1.44 (m, 2 H), 1.48-1.62 (m, 2 H), 2.97 (tdd, J=7.0, 7.0, 3.6, 3.5 Hz, 1 H), 3.33 (s, 6 H), 3.3-3.38 (m, 2 H), 4.22 (t, J=7.5 Hz, 2 H), 4.43 (t, J=4.9 Hz, 1 H), 5.34

(s, 2 H), 6.80 (d, J=5.5 Hz, 1 H), 7.26 (d, J=5.3 Hz, 1 H), 7.78 (d, J=5.8 Hz, 1 H), 8.23 (d, J=5.3 Hz, 1 H), 8.44 (s, 1 H)

EXAMPLE 37

Synthesis of 1-cyclopropyl-3-((3-isopentyl-3H-imidazo[4,5-c]pyridin-2-yl)methyl-1H-imidazo[4,5-c]pyridin-2(3H)-one 34

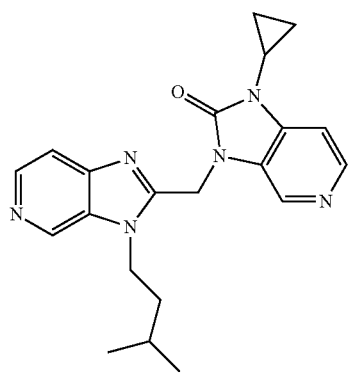

Step 1: Synthesis of 3-(isopentylamino)-4-nitropyridine 1-oxide 34-1

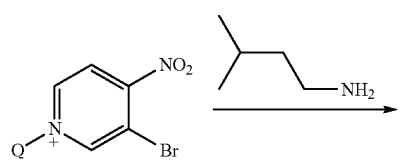

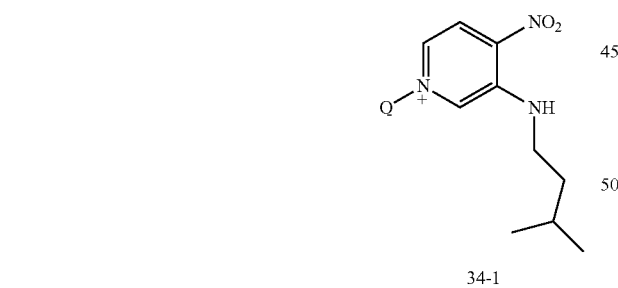

3-bromo-4-nitropyridine 1-oxide (CAS 1678-49-5, 10 g, 46 mmol) was dissolved in ethanol (400 mL). To the resulting mixture 3-methylbutan-1-amine (21.8 g, 250 mmol) was slowly added. The reaction mixture was stirred overnight at room temperature and concentrated under reduced pressure. The residue was dissolved in CH$_2$Cl$_2$ (500 mL) and washed with a saturated aqueous solution of NaHCO$_3$ (500 mL). The combined aqueous layers were extracted with CH$_2$Cl$_2$ (3×150 mL). The combined organic layers were dried over Na$_2$SO$_4$ and concentrated to give the intermediate 34-1 (9.8 g, 94%).

Step 2: Synthesis of N$^3$-isopentylpyridine-3,4-diamine 34-2

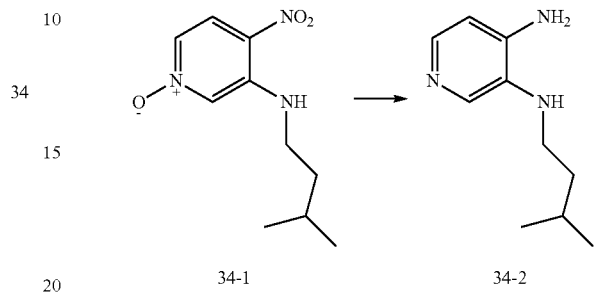

Intermediate 34-1 (15 g, 66 mmol) in methanol (600 mL) was hydrogenated (1 atm) with Raney Ni (6 g) as a catalyst at 20° C. overnight. After uptake of H$_2$ (4 eq.), the catalyst was removed by filtration. The filtrate was concentrated to a pink residue which was washed with tert-butyl methyl ether and CH$_3$CN to give the intermediate 34-2 (7 g, 59%).

Compound 34 was prepared in the same manner as compound 10 in a 4 step synthesis using intermediate 34-2 as starting material. m/z=377 (M+H)$^+$.

$^1$H NMR (360 MHz, CHLOROFORM-d) δ ppm 0.9-1.1 (m, 2H), 1.00 (d, J=6.6 Hz, 6 H), 1.13-1.23 (m, 2 H), 1.49-1.63 (m, 2 H), 1.66-1.82 (m, 1 H), 2.85-3.00 (m, 1 H), 4.33-4.50 (m, 2 H), 5.38 (s, 2 H), 7.15 (d, J=5.5 Hz, 1 H), 7.67 (d, J=5.5 Hz, 1 H), 8.34 (d, J=5.1 Hz, 1 H), 8.45 (d, J=5.5 Hz, 1 H), 8.64 (s, 1 H), 8.78 (s, 1 H)

EXAMPLE 38

Synthesis of 3-((5-chloro-1-(4,4,4-trifluorobutyl)-1H-imidazo[4,5-b]pyridin-2-yl)methyl)-1-cyclopropyl-1H-imidazo[4,5-c]pyridin-2(3H)-one 39

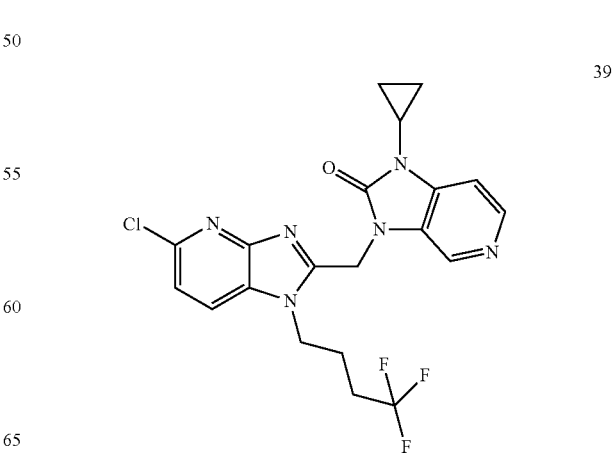

Step 1: Synthesis of (5-chloro-1-(4,4,4-trifluorobutyl)-1H-imidazo[4,5-b]pyridin-2-yl)methanol 39-3

This was prepared in the same manner as the intermediate 1-3 using 1-1 and 4,4,4-trifluorobutanal as starting materials.

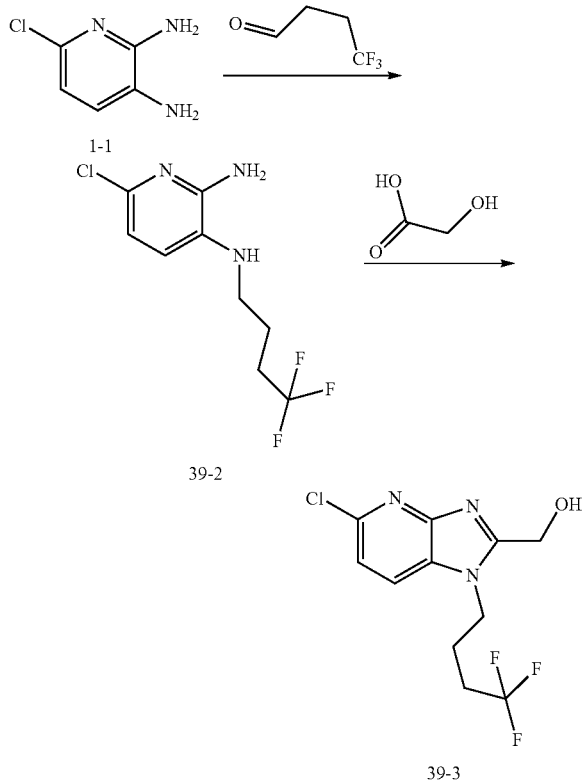

Step 2:

Compound 39 was prepared in the same manner as compound 1 using intermediates 39-3 and 10-d as starting materials. m/z=451 (M+H)+.

$^1$H NMR (400 MHz, CHLOROFORM-d) δ ppm 1.00 (s, 2 H), 1.12-1.23 (m, 2 H), 1.83-1.99 (m, 2 H), 2.12-2.31 (m, 2 H), 2.91 (spt, J=3.50 Hz, 1 H), 4.38-4.54 (m, 2 H), 5.38 (s, 2 H), 7.13 (dd, J=5.27, 0.50 Hz, 1 H), 7.27 (d, J=8.28 Hz, 1 H), 7.61 (d, J=8.53 Hz, 1 H), 8.36 (d, J=5.27 Hz, 1 H), 8.77 (s, 1 H)

EXAMPLE 39

Synthesis of 3-((5-chloro-1-(4-fluorobutyl)-1H-imidazo[4,5-b]pyridin-2-yl)methyl)-1-cyclopropyl-1H-imidazo[4,5-c]pyridin-2(3H)-one 40

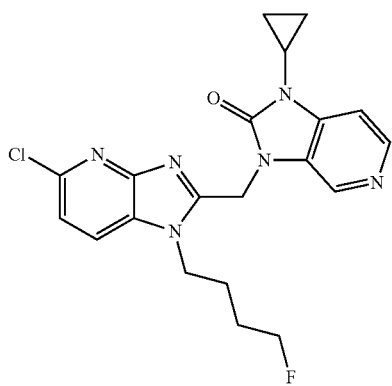

Compound 40 was made by a two step fluorination of compound 14.

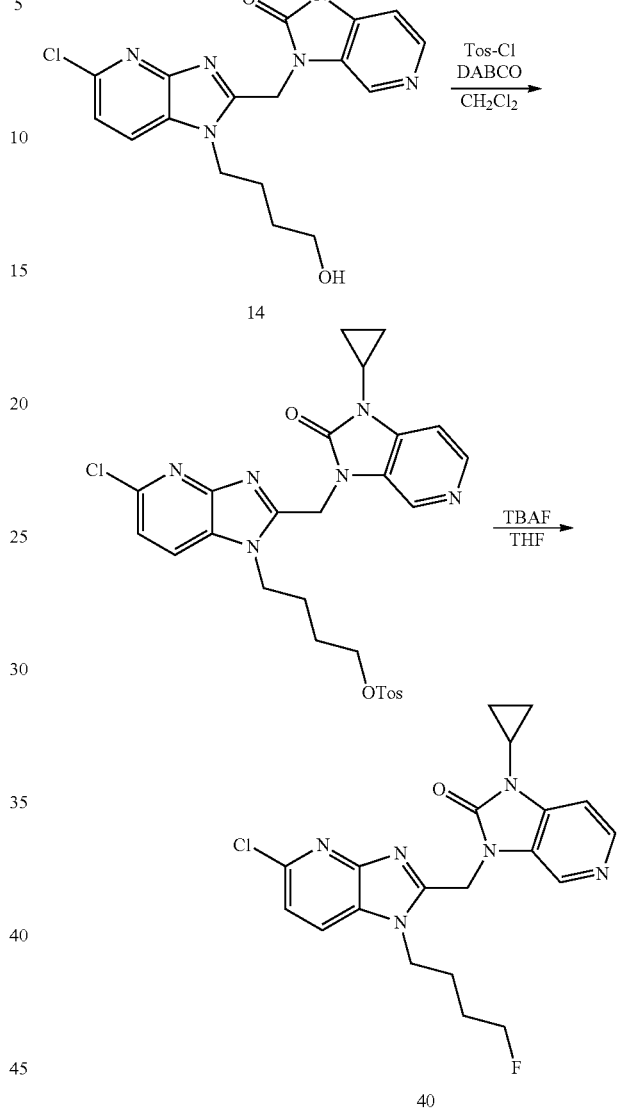

Compound 14 (5.4 g, 13.1 mmol) and DABCO (4.4 g, 39.2 mmol) were added to dry CH$_2$Cl$_2$ (50 ml) and the resulting solution was stirred at 0° C. under N$_2$. Tos-Cl (5.0 g, 26.2 mmol) was added portion wise to the mixture at 0° C. The mixture was stirred for 2 h at 15° C. The mixture was washed with 1N HCl (2×20 ml), saturated NaHCO$_3$ (40 ml) and brine (20 ml), dried over NaSO$_4$ and evaporated to dryness. 7.3 g of product was obtained as white powder. (Purity 85%, yield 98%). The tosylated intermediate (7.3 g, 12.9 mmol) was added to CH$_3$CN (HPLC grade, 70 ml). TBAF (6.7 g, 25.7 mmol, dried by co-evaporation with toluene) was added to the mixture. The mixture was refluxed for 15 min. The solvent was removed under vacuum. Water (200 ml) was added to the mixture and the mixture was extracted with CH$_2$Cl$_2$ (2*200 ml). The extractions were combined and concentrated under vacuum. The resulting residue was combined with 1.1 g of product (Purity 80%) obtained previously and then purified by high-performance liquid chromatography (C18, eluent: CH$_3$CN/H$_2$O from 15/85 to 35/65 with 0.5% of TFA as buffer). The collected fractions were combined and neutralized with NaHCO$_3$. The organic solvent was removed under vacuum. The mixture was filtered and the solid was washed with H$_2$O (200 ml). After drying under high vacuum, 3.075 g of product was obtained as white powder. (Purity 98%). m/z=415 (M+H)$^+$. $^1$H NMR (400 MHz, DMSO-d$_6$) δ ppm 0.88-0.96 (m, 2 H) 1.07 (m, J=5.02 Hz, 2 H) 1.60-1.85 (m, 4 H) 2.99 (tt, J=6.96, 3.58 Hz, 1 H) 4.45 (m, J=5.65, 5.65 Hz, 4 H) 5.46 (s, 2 H) 7.30 (d, J=5.27 Hz, 1 H) 7.36 (d, J=8.28 Hz, 1 H) 8.19 (d, J=8.53 Hz, 1 H) 8.27 (d, J=5.27 Hz, 1 H) 8.41 (s, 1 H).

EXAMPLE 40

Synthesis of 1-cyclopropyl-3-((1-(4,4,4-trifluorobutyl)-1H-imidazo[4,5-b]pyridin-2-yl)methyl)-1H-imidazo[4,5-c]pyridin-2(3H)-one 41

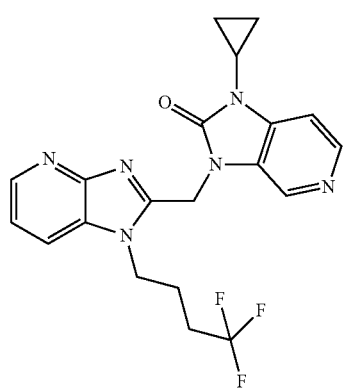

Compound 41 was prepared by Pd catalysed reduction of compound 39.

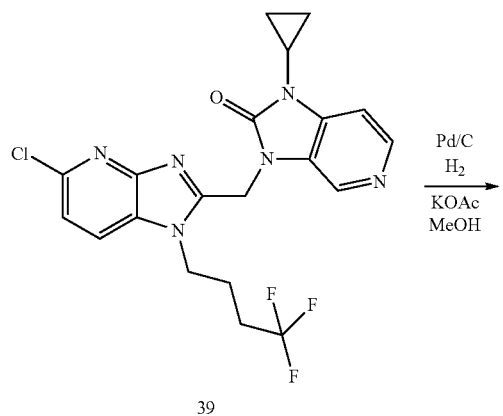

Compound 39 (1000 mg, 2.22 mmol) was dissolved in 30 mL MeOH. Pd/C (10%) and KOAc (218 mg, 2.22 mol) were added. The mixture was placed under H$_2$ and hydrogenated overnight. The mixture was filtrated over a plug of dicalite and evaporated. Compound 41 was purified by column chromatography on silicagel using CH$_2$Cl$_2$ to CH$_2$Cl$_2$/MeOH (NH$_3$) 9-1 as the eluent. After evaporation 550 mg (59% yield) of 41 was obtained as a white solid with a purity of 99%. m/z=417 (M+H)$^+$. $^1$H NMR (400 MHz, CHLOROFORM-d) δ ppm 0.93-1.05 (m, 2 H), 1.18 (s, 2 H), 1.91 (s, 2 H), 2.12-2.31 (m, 2 H), 2.91 (tt, J=6.93, 3.48 Hz, 1 H), 4.46 (t, J=7.80 Hz, 2 H), 5.42 (s, 2 H), 7.14 (d, J=5.27 Hz, 1 H), 7.25 (dd, J=8.28, 4.77 Hz, 1 H), 7.66 (dd, J=8.16, 1.38 Hz, 1 H), 8.36 (d, J=5.27 Hz, 1 H), 8.59 (dd, J=4.77, 1.51 Hz, 1 H), 8.80 (s, 1 H).

EXAMPLE 41

Synthesis of 1-cyclopropyl-3-((1-(4-fluorobutyl)-1H-imidazo[4,5-b]pyridin-2-yl)methyl)-1H-imidazo[4,5-c]pyridin-2(3H)-one 42

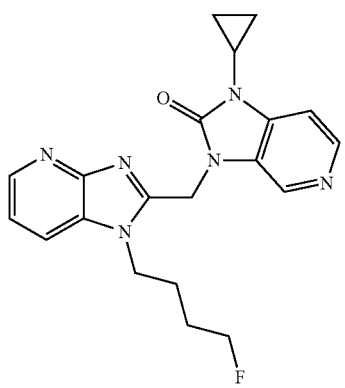

Compound 42 was prepared in the same manner as compound 11 using intermediates 42-5 and 10-d as starting materials.

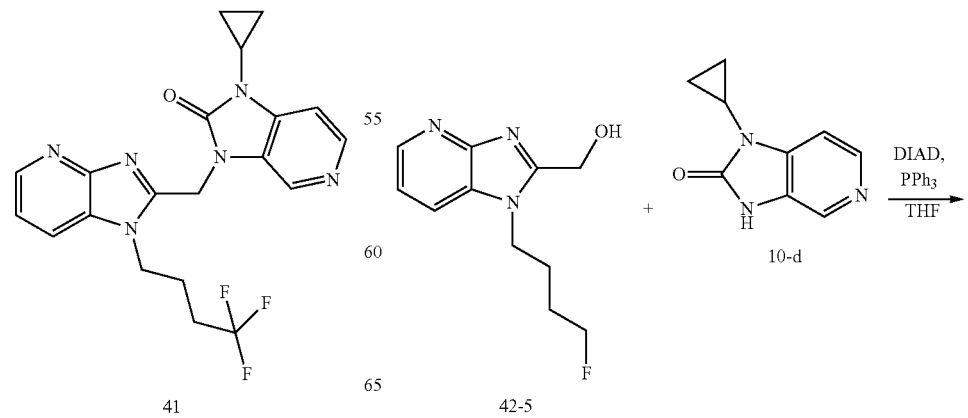

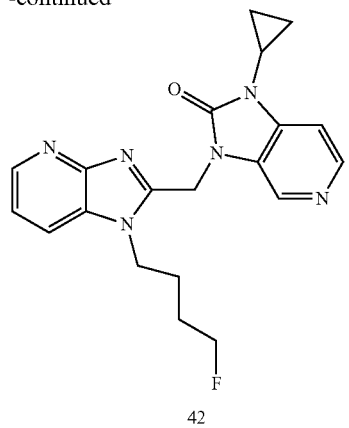

42

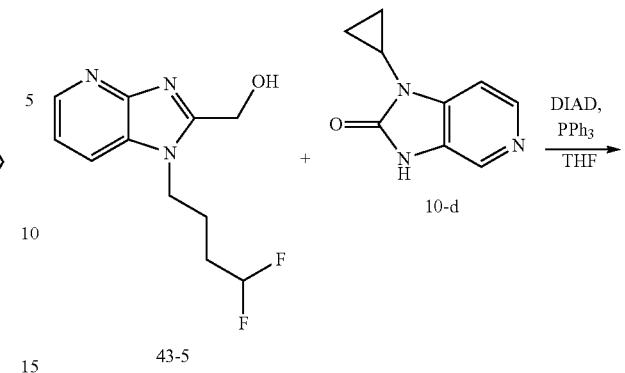

43-5

To a suspension of (1-(4-fluorobutyl)-1H-imidazo[4,5-b]pyridin-2-yl)methanol 42-5 (958 mg, 4.3 mmol), 1-cyclopropyl-1H-imidazo[4,5-c]pyridin-2(3H)-one 10-d (950 mg, 5.15 mmol) and triphenylphosphine (1350 mg, 5.15 mmol) in 30 ml dry THF was added (E)-diisopropyl diazene-1,2-dicarboxylate (1.26 ml, 6.43 mmol) at room temperature. The reaction mixture was stirred at room temperature for 16 hours. The precipitate was filtered off and washed with some diethyl ether to obtain the title product as a white powder (1036 mg, 63%).

m/z=381 (M+H)+. 1H NMR (400 MHz, DMSO-d6) δ ppm 0.88-0.96 (m, 2 H) 1.04-1.12 (m, 2 H) 1.60-1.86 (m, 4 H) 3.00 (tt, J=6.78, 3.26 Hz, 1 H) 4.34-4.56 (m, 4 H) 5.45 (s, 2 H) 7.27 (dd, J=8.16, 4.64 Hz, 1 H) 7.30 (d, J=5.27 Hz, 1 H) 8.08 (d, J=7.28 Hz, 1 H) 8.26 (d, J=5.27 Hz, 1 H) 8.37 (d, J=4.02 Hz, 1 H) 8.42 (s, 1 H)

Intermediate 42-5 was prepared in the same manner as intermediate 11-5 using the TFA salt of 4-fluorobutan-1-amine and 3-fluoro-2-nitropyridine as starting materials.

EXAMPLE 42

Synthesis of 1-cyclopropyl-3-((1-(4,4-difluorobutyl)-1H-imidazo[4,5-b]pyridin-2-yl)methyl)-1H-imidazo[4,5-c]pyridin-2(3H)-one 43

43

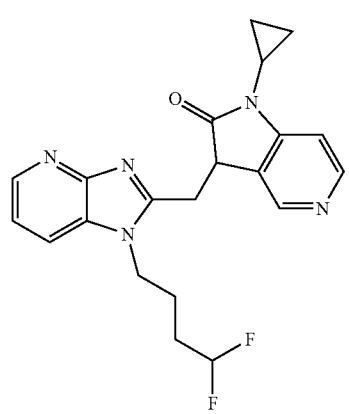

This compound was prepared in a similar way as compound 11 using intermediates 43-5 and 10-d as starting materials.

To a suspension of (1-(4,4-difluorobutyl)-1H-imidazo[4,5-b]pyridin-2-yl)methanol 43-5 (470 mg, 1.9 mmol), 1-cyclopropyl-1H-imidazo[4,5-c]pyridin-2(3H)-one 10-d (431 mg, 2.3 mmol) and triphenylphosphine (613 mg, 2 3 mmol) in 14 ml dry THF was added (E)-diisopropyl diazene-1,2-dicarboxylate (0.6 ml, 2.9 mmol) at room temperature. The reaction mixture was stirred at room temperature for 16 hours. The precipitate was filtered off and washed with some diethyl ether to obtain the title product as a white powder (450 mg, 58%). m/z=399 (M+H)+.

1H NMR (400 MHz, DMSO-d6) δ ppm 0.88-0.96 (m, 2 H) 1.04-1.12 (m, 2 H) 1.79-1.99 (m, 4 H) 2.99 (tt, J=7.00, 3.54 Hz, 1 H) 4.43 (t, J=7.28 Hz, 2 H) 5.46 (s, 2 H) 6.11 (tt, J=57.00, 4.30 Hz, 1 H) 7.24-7.34 (m, 2 H) 8.09 (dd, J=8.28, 1.51 Hz, 1 H) 8.27 (d, J=5.27 Hz, 1 H) 8.38 (dd, J=4.77, 1.51 Hz, 1 H) 8.43 (s, 1 H)

Intermediate 43-5 can be prepared in the same manner as intermediate 11-5 using 4,4-difluorobutan-1-amine hydrochloride and 3-fluoro-2-nitropyridine as starting materials.

4,4-difluorobutan-1-amine hydrochloride 15-e can be prepared as depicted in scheme 15 below.

Scheme 15: synthesis of 4,4-difluorobutan-1-amine 15-e

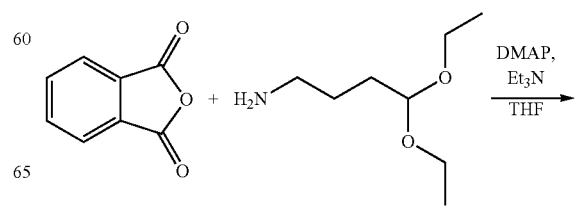

Step 2: Synthesis of 2-(4,4-diethoxybutyl)isoindoline-1,3-dione 15-b

A mixture of 2-(4,4-diethoxybutylcarbamoyl)benzoic acid 15-a (20.8 g, 67.235 mmoles) and sodium acetate (2.757 g, 0.5 eq) in acetic anhydride (95 mL) was heated at 110° C. for 3 hours. The reaction mixture was then cooled to RT and poured into 700 mL of ice-water. After stirring for 2 hours, it was then extracted with EtOAc. The combined organic layers were washed with a saturated aqueous $NaHCO_3$ solution, dried on $Na_2SO_4$, filtered, and evaporated to dryness to give the desired product 15-b (19.6 g, quantitative yield) which was used as such in the next reaction.

Step 3: Synthesis of 4-(1,3-dioxoisoindolin-2-yl)butanal 15-c

To a solution of 2-(4,4-diethoxybutyl)isoindoline-1,3-dione 15-b (19.6 g, 67.274 mmoles) in THF (130 mL) were added PTSA monohydrate (734 mg, 0.05 eq) and water (17 mL, 14 eq). The reaction mixture was stirred for 72 h at RT. Water (3 mL) and PTSA monohydrate (150 mg) were then added and stirring continued overnight. The reaction mixture was then diluted with 300 mL EtOAc, washed with $NaHCO_3$, then brine, dried over sodium sulfate, filtrated and evaporated to dryness. The crude was purified by flash chromatography using EtOAC as the eluent to provide 14 g (95% yield) of the desired compound 15-c as a brown oil which solidified upon standing. $^1$H NMR (400 MHz, CHLOROFORM-d) δ ppm 2.03 (quin, J=7.1 Hz, 2H), 2.54 (td, J=7.3 Hz, 2H), 3.75 (t, J=6.8 Hz, 2H), 7.70-7.74 (m, 2H), 7.79-7.92 (m, 2H), 9.78 (t, J=1.1 Hz, 1H).

Step 4: Synthesis of 2-(4,4-difluorobutyl)isoindoline-1,3-dione 15-d

To a stirred suspension of diethylaminodifluorosulfonium tetrafluoroborate (3.162 g, 13.81 mmoles) in CH2Cl2 (90 mL) at RT were added 4-(1,3-dioxoisoindolin-2-yl)butanal 15-c (2 g, 9.207 mmoles) and triethylamine trihydrofluoride (2.226 g, 1.5 eq). The mixture was stirred under $N_2$ atmosphere overnight. 100 mL of a saturated $NaHCO_3$ solution was added and the mixture was stirred for 10 minutes, until gas evolution stopped. The reaction mixture was then extracted with 150 mL DCM (2×). The combined organic layers were dried on $Na_2SO_4$, filtrated and evaporated to dryness. The crude was purified by flash chromatography using DCM as the eluent to provide 1.6 g (72% yield) of the desired compound 15-d as a yellowish oil. m/z=240 (M+H)$^+$; $^1$H NMR (400 MHz, CHLOROFORM-d) δ ppm 1.78-1.99 (m, 4H), 3.75 (t, J=6.8 Hz, 2H), 5.86 (tt, J=56.5, 3. Hz), 7.68-7.77 (m, 2H), 7.81-7.90 (m, 2H).

Step 5: Synthesis of 4,4-difluorobutan-1-amine 15-e

A solution of 2-(4,4-difluorobutyl)isoindoline-1,3-dione 15-d (8 g, 33.442 mmoles) and hydrazine (1.788 mL, 1.1 eq, 1.0 M in water) in 20 mL EtOH was heated at reflux for 2 hours. The mixture was then cooled in an ice-bath. The resulting precipitate of 2,3-dihydrophthalazine-1,4-dione was fil-

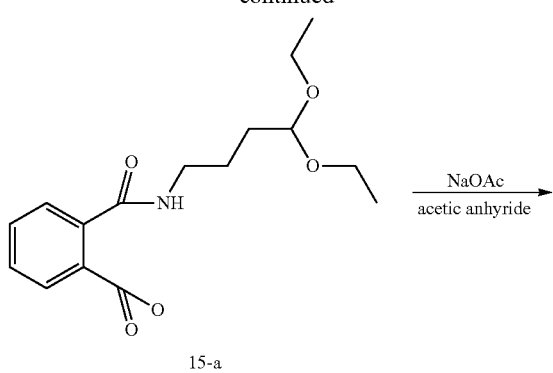

15-a

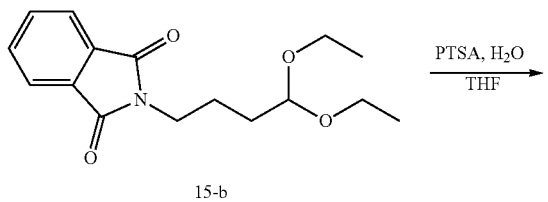

15-b

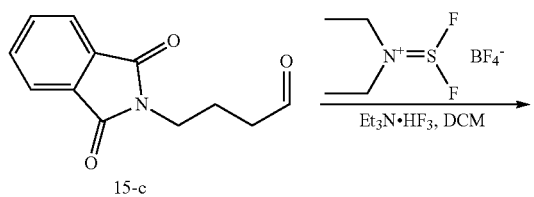

15-c

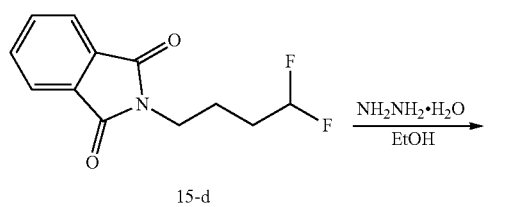

15-d 15-e

Step 1: Synthesis of 2-(4,4-diethoxybutylcarbamoyl)benzoic acid 15-a

To a solution of isobenzofuran-1,3-dione (10.5 g, 70.889 mmoles), DMAP (824 mg, 0.1 eq) and triethylamine (10.323 mL, 1.1 eq) in THF (100 mL) was added 4,4-diethoxybutan-1-amine (12.095 g, 1 eq) dropwise via syringe, over 10 minutes, at 0° C. The reaction mixture was then allowed to warm up to RT and was stirred overnight. Concentration of the reaction mixture in vacuo provided the desired compound 15-a (20.9 g, quantitative yield), which was used without purification in the next step. m/z=308 (M−H)$^-$ tered off and the filtrate was concentrated in vacuo to give the desired compound 15-e (3.6 g) which was used as such in the next reaction.

EXAMPLE 43

Synthesis of 1-cyclopropyl-3-((1-isopentyl-5-(trifluoromethyl)-1H-imidazo[4,5-b]pyridin-2-yl)methyl)-1H-imidazo[4,5-c]pyridin-2(3H)-one 44

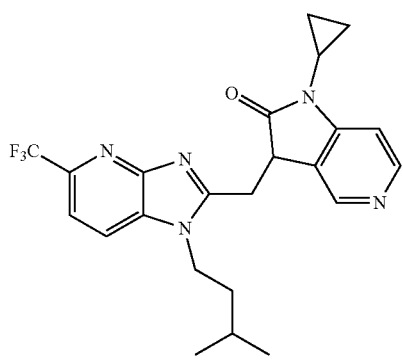

This compound was prepared in a similar way as compound 11 using intermediates 44-3 and 10-d as starting materials.

To a suspension of (1-isopentyl-5-(trifluoromethyl)-1H-imidazo[4,5-b]pyridin-2-yl)methanol 44-3 (1.0 g, 3.5 mmol (73% purity)), 1-cyclopropyl-1H-imidazo[4,5-c]pyridin-2 (3H)-one 10-d (731.8 mg, 4.2 mmol) and triphenylphosphine (1.1 g, 4.2 mmol) in 24 ml dry THF was added (E)-diisopropyl diazene-1,2-dicarboxylate (1.0 ml, 5.2 mmol) at room temperature. The reaction mixture was stirred at room temperature for 16 hours. The reaction mixture was evaporated to dryness and purified by preparative column chromatography to obtain 44 as a white solid (578.0 mg, 37%). m/z=445 (M+H)+. $^1$H NMR (400 MHz, CHLOROFORM-d) δ ppm 1.02 (m, J=6.50 Hz, 8H) 1.13-1.24 (m, 2 H) 1.48-1.64 (m, 2 H) 1.73 (dquin, J=13.19, 6.49, 6.49, 6.49, 6.49 Hz, 1 H) 2.92 (tt, J=6.81, 3.48 Hz, 1 H) 4.35-4.52 (m, 2 H) 5.41 (s, 2 H) 7.13 (d, J=5.27 Hz, 1 H) 7.61 (d, J=8.28 Hz, 1 H) 7.79 (d, J=8.28 Hz, 1 H) 8.34 (d, J=5.27 Hz, 1 H) 8.68 (s, 1 H).

Intermediate 44-3 was prepared in the same manner as intermediate 39-3 using 44-1 and 3-methylbutanal as the starting materials.

EXAMPLE 45

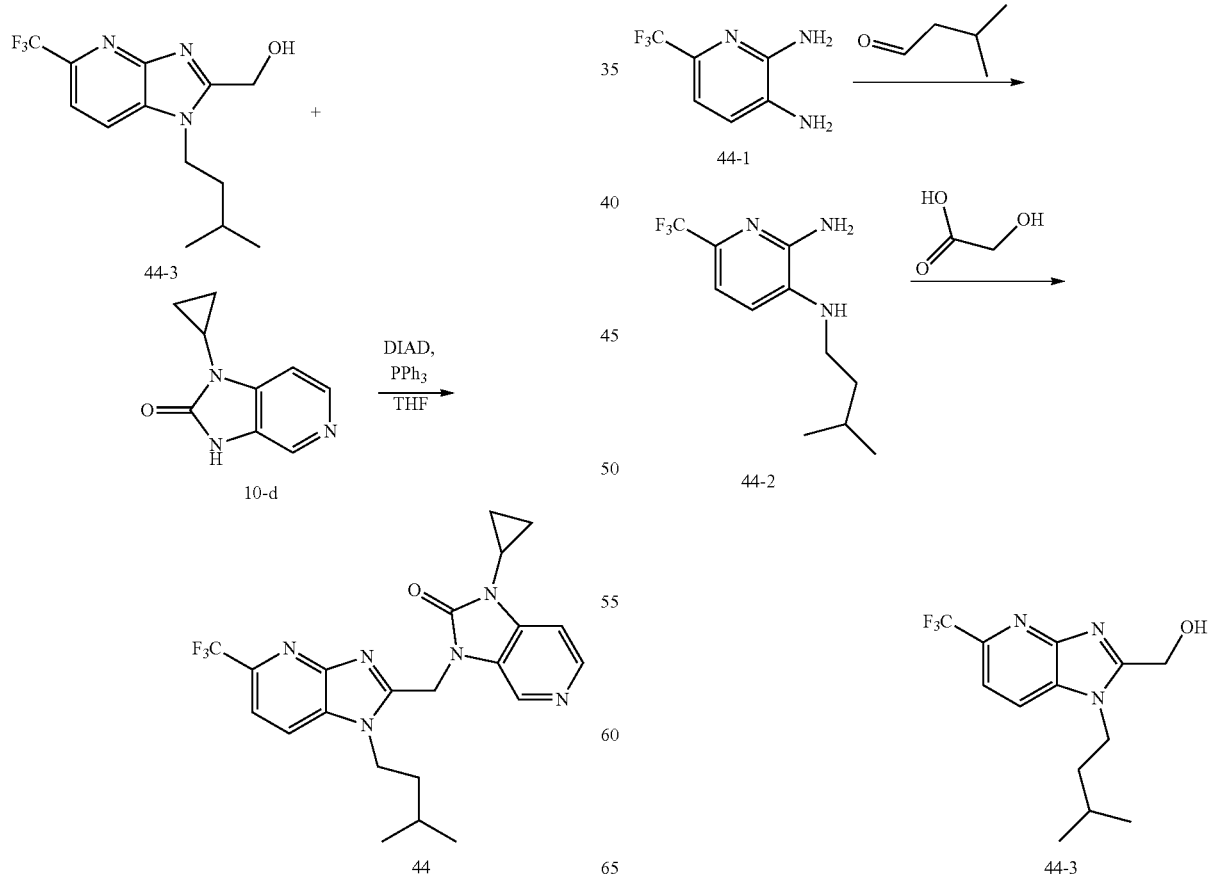

EXAMPLE 47

Synthesis of 3-{[5-chloro-1-(4-hydroxypentyl)-1H-imidazo[4,5-b]pyridin-2-yl]methyl}-1-cyclopropyl-1,3-dihydro-2H-imidazo[4,5-c]pyridin-2-one (67)

Step 1: synthesis of 4-(5-chloro-2-((1-cyclopropyl-2-oxo-1H-imidazo[4,5-c]pyridin-3(2H)-yl)methyl)-1H-imidazo[4,5-b]pyridin-1-yl)butanal (67-1)

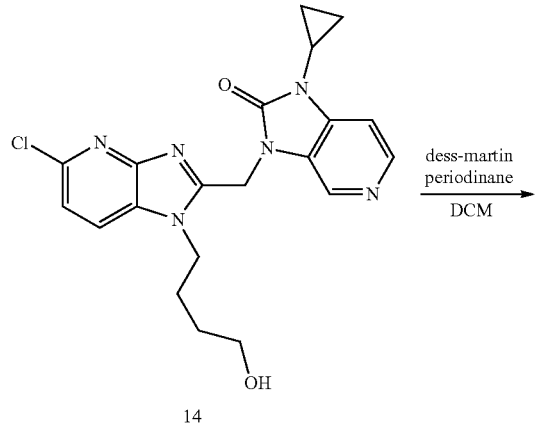

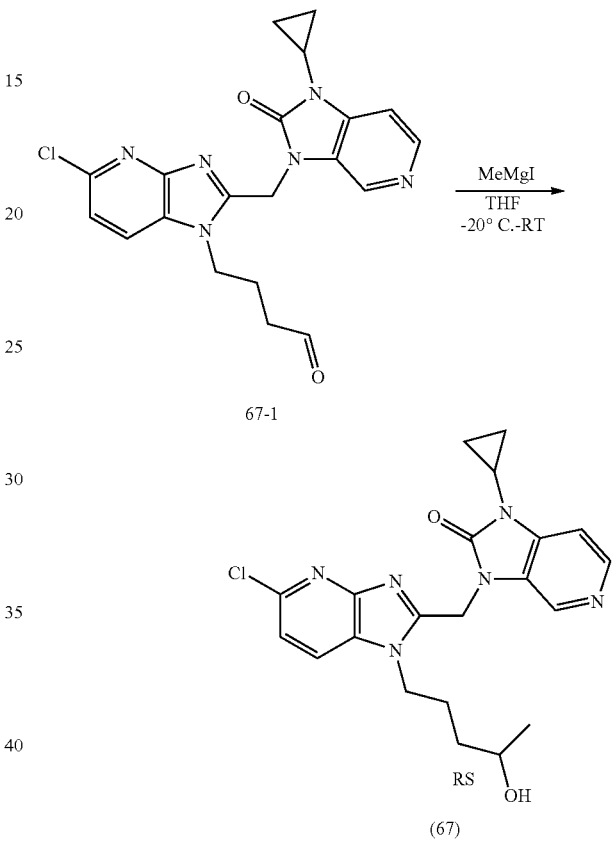

To the alcohol 14 (5 g, 12.11 mmoles) dissolved in DCM (80 mL) was added dess-martin periodinane (6.934 g, 1.35 eq, CAS 87413-09-0). The resulting mixture was stirred at Rt overnight. Diethylether was added (150 mL) and the mixture was stirred for 15 minutes. The mixture was filtrated and the filtrate washed quickly with an aqueous $Na_2S_2O_3$ solution, dried on $Na_2SO_4$, filtrated and evaporated. The resulting solid was washed again with a solution of 5% methanol in dichloromethane and the filtrate was washed with a $Na_2S_2O_3$ solution and dried over $Na_2SO_4$. The solution was concentrated and the aldehyde 67-1 was obtained as a light yellow solid (4.6 g, 93% yield) and was used as such in the next step. LCMS m/z=411 (M+H)+

Step 2: Synthesis of 3-{[5-chloro-1-(4-hydroxypentyl)-1H-imidazo[4,5-b]pyridin-2-yl]methyl}-1-cyclopropyl-1,3-dihydro-2H-imidazo[4,5-c]pyridin-2-one (67)

In a 100 mL dry flask, 4-{5-chloro-2-[1-cyclopropyl-2-oxo-1,2-dihydro-3H-imidazo[4,5-c]pyridin-3-yl)methyl]-1H-imidazo[4,5-b]pyridin-1-yl}butanal 67-1 (1.5 g, 3.6 mmol) was dissolved in dry THF (50 mL) and cooled until −20° C. under $N_2$ atmosphere. An excess methylmagnesium iodide (3M in THF) (1.8 mL, 5.5 mmol, 1.5 eq.) was then gently added dropwise to the cooled solution via syringe. The solution was warmed up until ambient temperature and stirred for 4 hours. The solution was diluted with 30 mL $NaHCO_3$ solution and extracted with EtOAC (30 mL). The combined organics were dried ($MgSO_4$) and concentrated in vacuo. The crude was purified on RP SunFire Prep column (C18 OBD-10 µm,30×150 mm), using a 0.25% $NH_4HCO_3$ solution in water-MeOH solution to give 350 mg (22%) of 3-{[5-chloro-1-(4-hydroxypentyl)-1H-imidazo[4,5-b]pyridin-2-yl]methyl}-1-1-cyclopropyl-1,3-dihydro-2H-imidazo[4,5-c]pyridin-2-one (67) as a white solid. $^1$H NMR (400 MHz, CHLOROFORM-d) δ ppm 0.99-1.05 (m, 2 H) 1.13-1.22 (m, 5 H) 1.43-1.57 (m, 2H) 1.77-1.91 (m, 2 H) 2.11 (br. s, 1 H) 2.89-2.98 (m, 1 H) 3.81-3.90 (m, 1 H) 4.32-4.50 (m, 2 H) 5.40 (s, 2 H) 7.13 (dd, J=5.27, 0.75 Hz, 1 H) 7.23 (d, J=8.53

Hz, 1 H) 7.65 (d, J=8.28 Hz, 1 H) 8.34 (d, J=5.27 Hz, 1 H) 8.75 (s, 1 H); LCMS m/z=427 (M+H)+

EXAMPLE 48

Synthesis of 3-((5-chloro-1-(4-hydroxy-4-methylpentyl)-1H-imidazo[4,5-b]pyridin-2-yl)methyl)-1-cyclopropyl-1H-imidazo[4,5-c]pyridin-2 (3H)-one (75)

Step 1: Synthesis of 3-((5-chloro-1-(4-oxopentyl)-1H-imidazo[4,5-b]pyridin-2-yl)methyl)-1-cyclopropyl-1H-imidazo[4,5-c]pyridin-2(3H)-one (75-1)

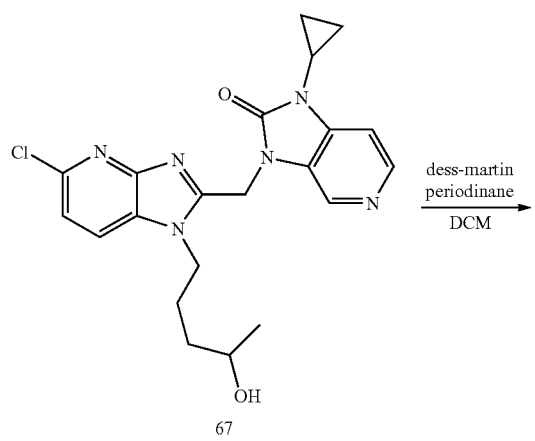

To the alcohol 67 (380 mg, 0.89 mmoles) dissolved in DCM (30 mL) was added dess-martin periodinane (509 mg, 1.35 eq, CAS 87413-09-0). The resulting mixture was stirred at Rt overnight. Diethylether was added (150 mL) and the mixture was stirred for 15 minutes. The mixture was filtrated and the filtrate washed quickly with an aqueous Na₂S₂O₃ solution, dried on Na₂SO₄, filtrated and evaporated. The resulting solid was purified by flash chromatography (10% MeOH in DCM) and the aldehyde 75 was obtained as a light yellow solid (218 mg, 58% yield). LCMS m/z=425 (M+H)+

Step 2: Synthesis of 3-((5-chloro-1-(4-hydroxy-4-methylpentyl)-1H-imidazo[4,5-b]pyridin-2-yl)methyl)-1-cyclopropyl-1H-imidazo[4,5-c]pyridin-2 (3H)-one (75)

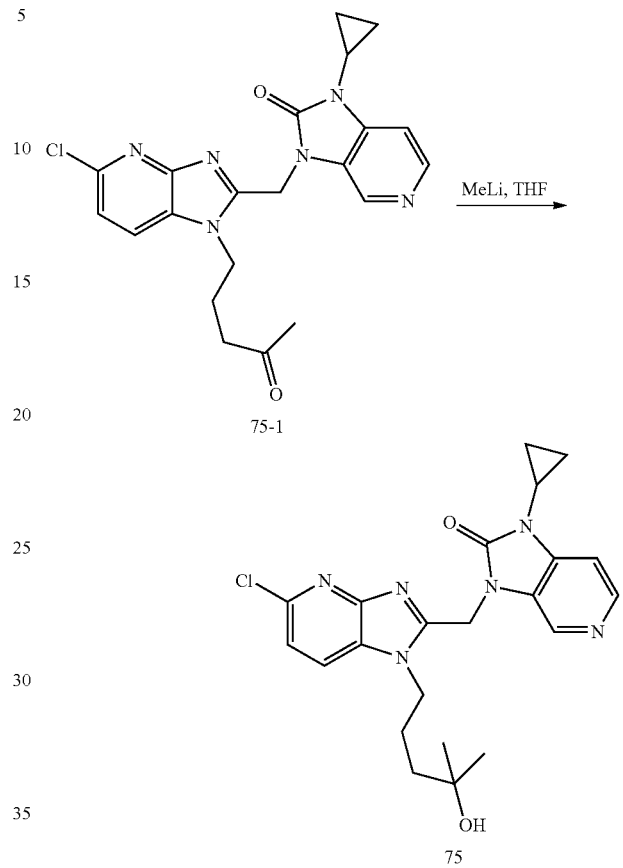

To a solution of ketone 75-1 (210 mg, 0.497 mmole) in THF was added MeLi (0.466 mL, 1.5 eq, 1.6 M in THF) dropwise, at 0° C. The resulting mixture was stirred at RT overnight, then was heated at 50° C. for 2 hours. After cooling to RT, the reaction mixture was poured in water, extracted with dichloromethane, dried over MgSO₄ and concentrated. The residue was purified by column chromatography using dichloromethane and methanol, followed by a purification by prep HPLC on RP SunFire Prep C18 OBD-10 μm,30×150 mm, and mobile phase (0.25% NH4HCO3 solution in water, CH3CN) to give 11 mg of the desired compound 75. LCMS m/z=441 (M+H)+; ¹H NMR (400 MHz, CHLOROFORM-d) δ ppm 0.97-1.05 (m, 2 H), 1.11-1.22 (m, 2 H), 1.17 (s, 6 H), 1.43-1.53 (m, 2 H), 1.74 (br. s., 1 H), 1.79-1.91 (m, 2 H), 2.82-3.05 (m, 1 H), 4.40 (t, J=7.5 Hz, 2 H), 5.39 (s, 2 H), 7.11 (d, J=5.0 Hz, 1 H), 7.20 (d, J=8.3 Hz, 1 H), 7.64 (d, J=8.3 Hz, 1 H), 8.31 (d, J=5.0 Hz, 1 H), 8.70 (s, 1 H).

EXAMPLE 49

Characterization of compounds, and test for RSV inhibitory activity are shown in tables 1-5.

General Experimental Details

HPLC-MS analysis was done using either one of the following methods:

Method 1:

The HPLC measurement was performed using an Agilent 1100 module comprising a pump, a diode-array detector (DAD) (wavelength used 220 nm), a column heater and a column as specified below. Flow from the column was split to an Agilent MSD Series G1946C and G1956A. MS detector was configured with API-ES (atmospheric pressure electro-

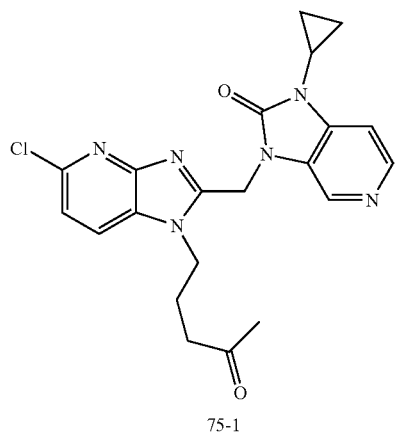

spray ionization). Mass spectra were acquired by scanning from 100 to 1000. The capillary needle voltage was 2500 V for positive ionization mode and 3000 V for negative ionization mode. Fragmentation voltage was 50 V. Drying gas temperature was maintained at 350° C. at a flow of 10 l/min. Reversed phase HPLC was carried out on a YMC-Pack ODS-AQ, 50×2.0 mm 5 mm column with a flow rate of 0.8 ml/min. Two mobile phases (mobile phase A: water with 0.1% TFA; mobile phase B: acetonitrile with 0.05% TFA) were used. First, 100% A was hold for 1 minute. Then a gradient was applied to 40% A and 60% B in 4 minutes and hold for 2.5 minutes. Typical injection volumes of 2 mL were used. Oven temperature was 50° C. (MS polarity: positive)

Method 2:

The HPLC measurement was performed using an Agilent 1100 module comprising a pump, a diode-array detector (DAD) (wavelength used 220 nm), a column heater and a column as specified below. Flow from the column was split to a Agilent MSD Series G1946C and G1956A. MS detector was configured with API-ES (atmospheric pressure electrospray ionization). Mass spectra were acquired by scanning from 100 to 1000. The capillary needle voltage was 2500 V for positive ionization mode and 3000 V for negative ionization mode. Fragmentation voltage was 50 V. Drying gas temperature was maintained at 350° C. at a flow of 10 l/min. Reversed phase HPLC was carried out on a YMC-Pack ODS-AQ, 50×2.0 mm 5 mm column with a flow rate of 0.8 mL/min. Two mobile phases (mobile phase A: water with 0.1% TFA; mobile phase B: acetonitrile with 0.05% TFA) were used. First, 90% A and 10% B was hold for 0.8 minutes. Then a gradient was applied to 20% A and 80% B in 3.7 minutes and hold for 3 minutes. Typical injection volumes of 2 mL were used. Oven temperature was 50° C. (MS polarity: positive)

Method 3:

Column: XTerra MS C18 2.5μ, 4.6×50 mm, mobile phase A: 10 mM $NH_4OOCH$+0.1% HCOOH in $H_2O$, mobile phase B: MeOH operating at a column temperature of 50° C. using a flow rate of 1.5 mL/min. Gradient conditions: t=0 min: 65% A, 35% B; t=3.5 min, 5% A, 95% B; t=5.5 min, 5% A, 95% B; t=5.6 min: 65% A, 35% B; t=7 min, 65% A, 35% B.

Method 4:

Column: SunFire C18 3.5μ. 4.6×100 mm, mobile phase A: 10 mM $NH_4OOCH$+0.1% HCOOH in $H_2O$, mobile phase B: MeOH operating at a column temperature of 50° C. using a flow rate of 1.5 mL/min. Gradient conditions: t=0 min: 65% A, 35% B; t=7 min, 5% A, 95% B; t=9.6 min, 5% A, 95% B; t=9.8 min: 65% A, 35% B; t=12 min, 65% A, 35% B.

NMR spectra were recorded on a Bruker Avance 400 spectrometer, operating at 400 MHz for $^1H$. Chemical shifts are given in ppm and a J value in Hz. Multiplicity is indicated using the following abbreviations: d for doublet, t for a triplet, m for a multiplet, etc. Thin-layer chromatography (TLC) was performed on 5×10 cm aluminium sheets coated with Silica-gel 60 $F_{254}$ (Merck KGaA).

Antiviral Activity

Black 96-well clear-bottom microtiter plates (Corning, Amsterdam, The Netherlands) were filled in duplicate using a customized robot system with serial 4-fold dilutions of compound in a final volume of 50 μl culture medium [RPMI medium without phenol red, 10% FBS, 0.04% gentamycin (50 mg/mL) and 0.5% DMSO]. Then, 100 μl of a HeLa cell suspension ($5×10^4$ cells/mL) in culture medium was added to each well followed by the addition of 50 μl rgRSV224 (MOI=0.02) virus in culture medium using a multidrop dispenser (Thermo Scientific, Erembodegem, Belgium). rgRSV224 virus is an engineered virus that includes an additional GFP gene (Hallak et al, 2000) and was in-licensed from the NIH (Bethesda, Md., USA). Medium, virus- and mock-infected controls were included in each test. Cells were incubated at 37° C. in a 5% $CO_2$ atmosphere. Three days post-virus exposure, viral replication was quantified by measuring GFP expression in the cells by a MSM laser microscope (Tibotec, Beerse, Belgium). The $EC_{50}$ was defined as the 50% inhibitory concentration for GFP expression. In parallel, compounds were incubated for three days in a set of white 96-well microtitier plates (Corning) and the cytotoxicity of compounds in HeLa cells was determined by measuring the ATP content of the cells using the ATPlite kit (PerkinElmer, Zaventem, Belgium) according to the manufacturer's instructions. The $CC_{50}$ was defined as the 50% concentration for cytotoxicity.

REFERENCES

Hallak L K, Spillmann D, Collins P L, Peeples M E. Glycosaminoglycan sulfation requirements for respiratory syncytial virus infection. J. Virol. 740, 10508-10513 (2000).

TABLE 1

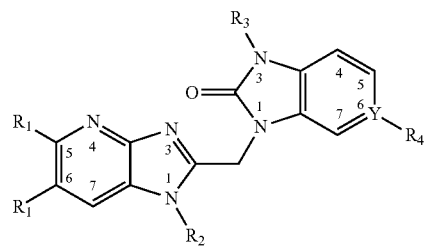

| N° | Name | $C_5$—$R_1$ | $C_6$—$R_1$ | $R_2$ | $R_3$ | Y—$R_4$ | RSV-wt_n_$EC_{50}$ | RSV-wt_$EC_{50}$ (μM) | TOX-HELA_n_$EC_{50}$ | TOX-HELA_$EC_{50}$ (μM) |
|---|---|---|---|---|---|---|---|---|---|---|
| 1 | 3-((5-chloro-1-isopentyl-1H-imidazo[4,5-b]pyridin-2-yl)methyl)-1-cyclopropyl-1H-imidazo[4,5-c]pyridin-2(3H)-one | C—Cl | C—H | | | N | 1 | 0.000365 | 1 | >9.83603 |

TABLE 1-continued

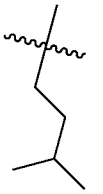

| N° | Name | C5—R1 | C6—R1 | R2 | R3 | Y—R4 | RSV-wt_n_EC50 | RSV-wt_EC50 (μM) | TOX-HELA_n_EC50 | TOX-HELA_EC50 (μM) |
|---|---|---|---|---|---|---|---|---|---|---|
| 2 | 3-((5-chloro-1-isopentyl-1H-imidazo[4,5-b]pyridin-2-yl)methyl)-1-(oxetan-3-yl)-1H-imidazo[4,5-c]pyridin-2(3H)-one | C—Cl | C—H | 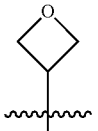 | 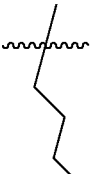 | N | 1 | 0.001583 | 1 | >9.83603 |
| 3 | 4-(5-chloro-2-((1-cyclopropyl-2-oxo-1H-imidazo[4,5-c]pyridin-3(2H)-yl)methyl)-1H-imidazo[4,5-b]pyridin-1yl)butyl pivalate | C—Cl | C—H | 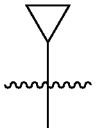 [SMILES: *C1CC1] | 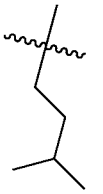 | N | 1 | 0.003293 | 1 | >9.83603 |
| 4 | 1-cyclopropyl-3-((1-isopentyl-1H-imidazo[4,5-b]pyridin-2-yl)methyl)-1H-benzo[d]imidazol-2(3H)-one | C—H | C—H | 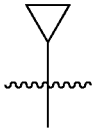 |  | C—H | 1 | 0.007081 | 1 | >9.83603 |
| 5 | 1-cyclopropyl-3-((1-isopentyl-1H-imidazo[4,5-b]pyridin-2-yl)methyl)-1H-imidazo[4,5-c]pyridin-2(3H)-one | C—H | C—H | 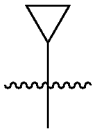 [SMILES: *C1CC1] |  | N | 4 | 0.008665 | 4 | >98.3603 |
| 6 | 3-((5-chloro-1-isopentyl-1H-imidazo[4,5-b]pyridin-2-yl)methyl)-1-cyclopropyl-5-fluoro-1H-benzo[d]imidazol-2(3H)-one | C—Cl | C—H | 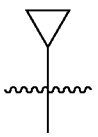 [SMILES: *C1CC1] | | C—F | 2 | 0.008667 | 2 | >9.83603 |

TABLE 1-continued

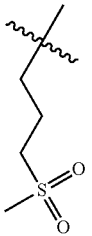 [SMILES: *CCCS(C)(=O)=O]

| N° | Name | C5—R1 | C6—R1 | R2 | R3 | Y—R4 | RSV-wt_n_EC50 | RSV-wt_EC50 (μM) | TOX-HELA_n_EC50 | TOX-HELA_EC50 (μM) |
|---|---|---|---|---|---|---|---|---|---|---|
| 7 | 1-cyclopropyl-3-((1-(3-(methylsulfonyl)propyl)-1H-imidazo[4,5-b]pyridin-2-yl)methyl)-1H-imidazo[4,5-c]pyridin-2(3H)-one | C—H | C—H | 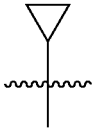 [SMILES: *C1CC1] | 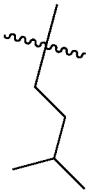 [SMILES: *CCC(C)C] | N | 1 | 0.013701 | 2 | >9.83603 |
| 8 | 1-cyclopropyl-5-fluoro-3-((1-isopentyl-1H-imidazo[4,5-b]pyridin-2-yl)methyl)-1H-benzo[d]imidazol-2(3H)-one | C—H | C—H | 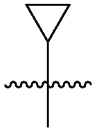 [SMILES: *C1CC1] |  | C—F | 3 | 0.01586 | 2 | >9.83603 |
| 9 | 3-((1-isopentyl-1H-imidazo[4,5-b]pyridin-2-yl)methyl)-1-(oxetan-3-yl)-1H-imidazo[4,5-c]pyridin-2(3H)-one | C—H | C—H | 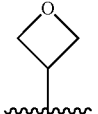 | 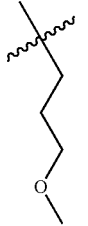 [SMILES: *CCCOC] | N | 2 | 0.058072 | 1 | >9.83603 |
| 10 | 1-cyclopropyl-3-((1-(3-(methoxypropyl)-1H-imidazo[4,5-b]pyridin-2-yl)methyl)-1H-imidazo[4,5-c]pyridin-2(3H)-one | C—H | C—H | 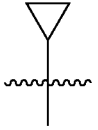 [SMILES: *C1CC1] | 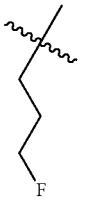 [SMILES: *CCCF] | N | 2 | 0.089347 | 2 | 4.7555418 |
| 11 | 1-cyclopropyl-3-((1-(3-(fluoropropyl)-1H-imidazo[4,5-b]pyridin-2-yl)methyl)-1H-imidazo[4,5-c]pyridin-2(3H)-one | C—H | C—H | 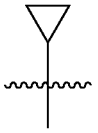 | 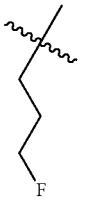 [SMILES: *CCCF] | N | 2 | 0.090853 | 2 | >9.83603 |

TABLE 1-continued

| N° | Name | $C_5$—$R_1$ | $C_6$—$R_1$ | $R_2$ | $R_3$ | Y—$R_4$ | RSV-wt_n_EC$_{50}$ | RSV-wt_EC$_{50}$ (μM) | TOX-HELA_n_EC$_{50}$ | TOX-HELA_EC$_{50}$ (μM) |
|---|---|---|---|---|---|---|---|---|---|---|
| 12 | 3-((1-(3-methoxypropyl)-1H-imidazo[4,5-b]pyridin-2-yl)methyl)-1-(oxetan-3-yl)-1H-imidazo[4,5-c]pyridin-2(3H)-one | C—H | C—H | | | N | 1 | 1.936065 | 3 | >98.3603 |
| 13 | 3-((5-chloro-1-isopentyl-1H-imidazo[4,5-b]pyridin-2-yl)methyl)-3-cyclopropyl-1H-benzo[d]imidazol-2(3H)-one | C—Cl | C—H | | | C—H | 1 | 0.0023 | 2 | >9.84 |
| 14 | 3-((5-chloro-1-(4-hydroxybutyl)-1H-imidazo[4,5-b]pyridin-2-yl)methyl)-1-cyclopropyl-1H-imidazo[4,5-c]pyridin-2(3H)-one | C—Cl | C—H | | | N | 1 | 0.006 | 2 | >9.84 |
| 15 | 1-cyclopropyl-5-fluoro-3-((1-(3-methoxypropyl)-1H-imidazo[4,5-b]pyridin-2-yl)methyl)-1H-benzo[d]imidazol-2(3H)-one | C—H | C—H | | | C—F | 1 | 0.22 | 2 | >98.3603 |
| 39 | 3-((5-chloro-1-(4,4,4-trifluorobutyl)-1H-imidazo[4,5-b]pyridin-2-yl)methyl)-1-cyclopropyl-1H-imidazo[4,5-b]pyridin-2(3H)-one | C—Cl | C—H | | | N | 3 | 0.00096 | 3 | >98.3603 |

TABLE 1-continued

| N° | Name | C5—R1 | C6—R1 | R2 | R3 | Y—R4 | RSV-wt_n_EC50 | RSV-wt_EC50 (μM) | TOX-HELA_n_EC50 | TOX-HELA_EC50 (μM) |
|---|---|---|---|---|---|---|---|---|---|---|
| 40 | 3-((5-chloro-1-(4-fluorobutyl)-1H-imidazo[4,5-b]pyridin-2-yl)methyl)-1-cyclopropyl-1H-imidazo[4,5-b]pyridin-2(3H)-one | C—Cl | C—H |  |  | N | 9 | 0.002 | 11 | >98.3603 |
| 41 | 1-cyclopropyl-3-((1-(4,4,4-trifluorobutyl)-1H-imidazo[4,5-b]pyridin-2-yl)methyl)-1H-imidazo[4,5-c]pyridin-2(3H)-one | C—H | C—H |  |  | N | 4 | 0.0071 | 4 | >98.3603 |
| 42 | 1-cyclopropyl-3-((1-(4-fluorobutyl)-1H-imidazo[4,5-b]pyridin-2-yl)methyl)-1H-imidazo[4,5-c]pyridin-2(3H)-one | C—H | C—H |  |  | N | 1 | 0.0052 | 1 | >98.3603 |
| 43 | 1-cyclopropyl-3-((1-(4,4-difluorobutyl)-1H-imidazo[4,5-b]pyridin-2-yl)methyl)-1H-imidazo[4,5-c]pyridin-2(3H)-one | C—H | C—H |  | 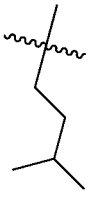 [SMILES: *CCC(C)C] | N | | | | |
| 44 | 1-cyclopropyl-3-((1-isopentyl-5-(trifluoromethyl)-1H-imidazo[4,5-b]pyridin-2-yl)methyl)-1H-imidazo[4,5-c]pyridin-2(3H)-one | C—CF3 | C—H |  | | N | 1 | 0.019 | 1 | >98.3603 |

TABLE 2

| N° | Name | C5—R1 | C6—R1 | R2 | R3 | R4 | Y | RSV-wt_n_EC50 | RSV-wt_EC50 (μM) | TOX-HELA_n_EC50 | TOX-HELA_EC50 (μM) |
|---|---|---|---|---|---|---|---|---|---|---|---|
| 16 | 3-((6-bromo-3-isopentyl-3H-imidazo[4,5-b]pyridin-2-yl)methyl)-1-cyclopropyl-1H-imidazo[4,5-c]pyridin-2(3H)-one | C—Br | C—H | 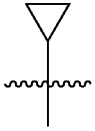 [SMILES: *C1CC1] |  | H | N | 2 | 0.008806 | 4 | >98.3603 |
| 17 | 3-((6-(aminomethyl)-3-isopentyl-3H-imidazo[4,5-b]pyridine-2-yl)methyl)-1-cyclopropyl-1H-imidazo[4,5-c]pyridin-2(3H)-one | C—CH2NH2 | C—H | 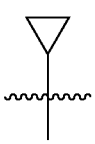 [SMILES: *C1CC1] |  | H | N | 12 | 0.011817 | 3 | >98.3603 |
| 18 | 3-((6-bromo-3-isopentyl-3H-imidazo[4,5-b]pyridin-2-yl)methyl)-1-(oxetan-3-yl)-1H-imidazo[4,5-c]pyridin-2(3H)-one | C—Br | C—H | 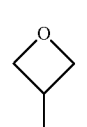 |  | H | N | 3 | 0.017331 | 2 | >9.83603 |
| 19 | 3-((6-bromo-3-(4-hydroxybutyl)-3H-imidazo[4,5-b]pyridin-2-yl)methyl)-1-cyclopropyl-1H-imidazo[4,5-c]pyridin-2(3H)-one | C—Br | C—H |  | 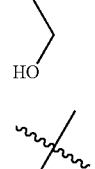 | H | N | 3 | 0.019057 | 1 | >98.3603 |
| 20 | 3-((6-bromo-3-(4-hydroxybutyl)-3H-imidazo[4,5-b]pyridin-2-yl)methyl)-1-(oxetan-3-yl)-1H-imidazo[4,5-c]pyridin-2(3H)-one | C—Br | C—H |  | 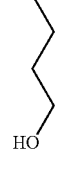 | H | N | 2 | 0.036127 | 3 | >9.83603 |
| 21 | 3-((6-chloro-3-(4-hydroxybutyl)-3H-imidazo[4,5-b]pyridin-2-yl)methyl)-1-cyclopropyl-1H-imidazo[4,5-c]pyridin-2(3H)-one | C—Cl | C—H |  | | H | N | 2 | 0.054553 | 2 | >9.83603 |

TABLE 2-continued

| N° | Name | C$_5$—R$_1$ | C$_6$—R$_1$ | R$_2$ | R$_3$ | R$_4$ | Y | RSV-wt_n_EC$_{50}$ | RSV-wt_EC$_{50}$ (μM) | TOX-HELA_n_EC$_{50}$ | TOX-HELA_EC$_{50}$ (μM) |
|---|---|---|---|---|---|---|---|---|---|---|---|
| 22 | 1-cyclopropyl-3-((6-fluoro-3-(4-hydroxybutyl)-3H-imidazo[4,5-b]pyridin-2-yl)methyl)-1H-imidazo[4,5-c]pyridin-2(3H)-one | C—F | C—H | 4-hydroxybutyl | cyclopropyl | H | N | 2 | 0.402689 | 2 | >9.83603 |
| 23 | 2-((1-cyclopropyl-2-oxo-1H-imidazo[4,5-c]pyridin-3(2H)-yl)methyl)-3-isopentyl-3H-imidazo[4,5-b]pyridin-6-ylboronic acid | C—B(OH)$_2$ | C—H | isopentyl | cyclopropyl | H | N | 3 | 0.645431 | 3 | >98.3603 |
| 24 | 1-cyclopropyl-3-((3-isopentyl-3H-imidazo[4,5-b]pyridin-2-yl)methyl)-1H-imidazo[4,5-c]pyridin-2(3H)-one | C—H | C—H | isopentyl | cyclopropyl | H | N | 2 | 1.223404 | 3 | >98.3603 |
| 25 | 4-chloro-3-((3-isopentyl-3H-imidazo[4,5-b]pyridin-2-yl)methyl)-1-isopropyl-1H-imidazo[4,5-c]pyridin-2(3H)-one | C—H | C—H | isopentyl | isopropyl | Cl | N | 1 | 8.270276 | 1 | >24.5901 |
| 26 | methyl 2-((1-cyclopropyl-2-oxo-1H-imidazo[4,5-c]pyridin-3(2H)-yl)methyl)-3-isopentyl-3H-imidazo[4,5-b]pyridine-6-carboxylate | C—CO$_2$Me | C—H | isopentyl | cyclopropyl | H | N | 1 | 8.60855 | 2 | >98.3603 |
| 27 | 2-((1-cyclopropyl-2-oxo-1H-imidazo[4,5-c]pyridin-3(2H)-yl)methyl)-3-isopentyl-3H-imidazo[4,5-b]pyridine-6-carbonitrile | C—CN | C—H | isopentyl | cyclopropyl | H | N | 1 | 34.06748 | 1 | >98.3603 |

TABLE 2-continued

| N° | Name | C5—R1 | C6—R1 | R2 | R3 | R4 | Y | RSV-wt_n_EC50 | RSV-wt_EC50 (μM) | TOX-HELA_n_EC50 | TOX-HELA_EC50 (μM) |
|---|---|---|---|---|---|---|---|---|---|---|---|
| 28 | 2-((1-cyclopropyl-2-oxo-1H-imidazo[4,5-c]pyridin-3(2H)-yl)methyl)-3-isopentyl-3H-imidazo[4,5-b]pyridine-6-carboxylic acid | C—CO2H | C—H | 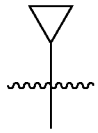 [SMILES: *C1CC1] |  | H | N | 2 | >49.1802 | 2 | >49.1802 |
| 29 | 3-((3-isopentyl-3H-imidazo[4,5-b]pyridin-2-yl)methyl)-1-isopropyl-2-oxo-2,3-dihydro-1H-imidazo[4,5-c]pyridine-4-carbonitrile | C—H | C—H | 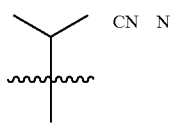 |  | CN | N | 1 | >98.3603 | 1 | >98.3603 |
| 30 | 1-((6-bromo-3-isopentyl-3H-imidazo[4,5-b]pyridin-2-yl)methyl)-3-cyclopropyl-1H-benzo[d]imidazol-2(3H)-one | C—Br | C—H | 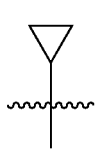 [SMILES: *C1CC1] | 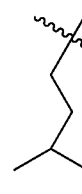 | H | CH | | | 1 | >9.84 |

TABLE 3

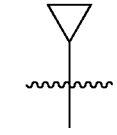 [SMILES: *C1CC1]

| N° | Name | X4—R1 | X5—R1 | X6—R1 | R2 | R3 | Y—R4 | RSV-wt_n_EC50 | RSV-wt_EC50 (μM) | TOX-HELA_n_EC50 | TOX-HELA_EC50 (μM) |
|---|---|---|---|---|---|---|---|---|---|---|---|
| 31 | 1-cyclopropyl-3-((1-isopentyl-1H-imidazo[4,5-c]pyridin-2-yl)methyl-1H-benzo[d]imidazol-2(3H)-one | C—H | N | C—H | | | C—H | 1 | 0.005399 | 2 | >9.83603 |

TABLE 3-continued

| N° | Name | X₄—R₁ | X₅—R₁ | X₆—R₁ | R₂ | R₃ | Y—R₄ | RSV-wt_n_EC₅₀ | RSV-wt_EC₅₀ (μM) | TOX-HELA_n_EC₅₀ | TOX-HELA_EC₅₀ (μM) |
|---|---|---|---|---|---|---|---|---|---|---|---|
| 32 | 1-cyclopropyl-5-fluoro-3-((1-isopentyl-1H-imidazo[4,5-c]pyridin-2-yl)methyl-1H-benzo[d]imidazol-2(3H)-one | C—H | N | C—H | isopentyl | cyclopropyl | C—F | 2 | 0.011281 | 3 | >9.83603 |
| 33 | 1-cyclopropyl-3-((1-isopentyl-1H-imidazo[4,5-c]pyridin-2-yl)methyl-1H-imidazo[4,5-c]pyridin-2(3H)-one | C—H | N | C—H | isopentyl | cyclopropyl | N | 13 | 0.030399 | 2 | >98.3603 |
| 34 | 1-cyclopropyl-3-((3-isopentyl-3H-imidazo[4,5-c]pyridin-2-yl)methyl-1H-imidazo[4,5-c]pyridin-2(3H)-one | C—H | C—H | N | isopentyl | cyclopropyl | N | 2 | 0.073986 | 4 | >98.3603 |
| 35 | 1-cyclopropyl-3-((1-(4-hydroxybutyl)-1H-imidazo[4,5-c]pyridin-2-yl)methyl-1H-imidazo[4,5-c]pyridin-2(3H)-one | C—H | N | C—H | 4-hydroxybutyl | cyclopropyl | N | 1 | 0.079508 | 1 | >98.3603 |
| 36 | 3-((1-isopentyl-1H-imidazo[4,5-c]pyridin-2-yl)methyl-1-(oxetan-3-yl)-1H-imidazo[4,5-c]pyridin-2(3H)-one | C—H | N | C—H | isopentyl | oxetan-3-yl | N | 1 | 0.09487 | 2 | >9.83603 |
| 37 | 1-cyclopropyl-3-((4-(dimethylamino)-1-(4-hydroxybutyl)-1H-imidazo[4,5-c]pyridin-2-yl)methyl-1H-imidazo[4,5-c]pyridin-2(3H)-one | C—NMe₂ | N | C—H | 4-hydroxybutyl | cyclopropyl | N | 3 | 0.273628 | 3 | >9.83603 |

TABLE 3-continued

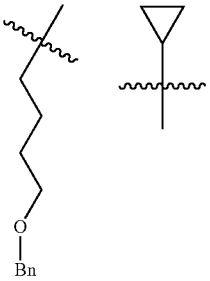

| N° | Name | X₄—R₁ | X₅—R₁ | X₆—R₁ | R₂ | R₃ | Y—R₄ | RSV-wt_n_EC₅₀ | RSV-wt_EC₅₀ (μM) | TOX-HELA_n_EC₅₀ | TOX-HELA_EC₅₀ (μM) |
|---|---|---|---|---|---|---|---|---|---|---|---|
| 38 | 3-((1-(4-benzyloxy)butyl)-4-chloro-1H-imidazo[4,5-c]pyridin-2-yl)methyl-1-cyclopropyl-1H-imidazo[4,5-c]pyridin-2(3H)-one | C—Cl | N | C—H |  | 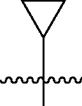 | N | 1 | 1.479585 | 1 | >98.3603 |

TABLE 4

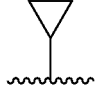

| X₄—R₁ | X5—R₁ | R₂ | R₃ | Y—R₄ | ¹H NMR | WT activity EC₅₀ (μM) | SI CC₅₀/EC₅₀ |
|---|---|---|---|---|---|---|---|
| 99 | N | C—Cl |  | 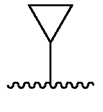 | N | ¹H NMR (400 MHz, CHLOROFORM-d) δ ppm 0.96-1.05 (m, 2 H) 1.11-1.26 (m, 2 H) 2.06-2.22 (m, 2 H) 2.51 (t, J = 6.90 Hz, 2 H) 2.88-2.97 (m, 1 H) 4.57 (t, J = 7.50 Hz, 2 H) 5.38 (s, 2 H) 7.15 (dd, J = 5.27, 0.75 Hz, 1 H) 7.29 (d, J = 8.53 Hz, 1 H) 7.72 (d, J = 8.53 Hz, 1 H) 8.38 (d, J = 5.27 Hz, 1 H) 8.79 (s, 1 H) | 0.010092 | >9746 |
| 100 | N | C—Cl | | | C—H | ¹H NMR (400 MHz, CHLOROFORM-d) δ ppm 0.95-1.06 (m, 2 H) 1.11-1.20 (m, 2 H) 2.01-2.11 (m, 2 H) 2.50 (t, J = 7.03 Hz, 2 H) 2.88-2.95 (m, 1 H) 4.57 (t, J = 7.50 Hz, 2 H) 5.37 (s, 2 H) 7.07-7.15 (m, 2 H) 7.19-7.23 (m, 1 H) 7.27-7.30 (m, 1 H) 7.57-7.62 (m, 1 H) 7.70 (d, J = 8.28 Hz, 1 H) | 0.020842 | >2399 |

TABLE 4-continued

| | X₄—R₁ | X₅—R₁ | R₂ | R₃ | Y—R₄ | ¹H NMR | WT activity EC₅₀ (μM) | SI CC₅₀/EC₅₀ |
|---|---|---|---|---|---|---|---|---|
| 101 | N | C—Cl | (CH₂)₄OH chain | oxetanyl | N | ¹H NMR (400 MHz, DMSO-d₆) δ ppm 1.37-1.52 (m, 2 H), 1.66-1.82 (m, 2 H), 3.40 (t, J = 6.02 Hz, 2 H), 4.45 (br. s., 1 H), 4.41 (t, J = 7.53 Hz, 2 H), 4.92-5.01 (m, 2 H), 5.08 (t, J = 6.65 Hz, 2 H), 5.51 (s, 2 H), 5.53-5.62 (m, 1 H), 7.36 (d, J = 8.28 Hz, 1 H), 7.49-7.62 (m, 1 H), 8.17 (d, J = 8.53 Hz, 1 H), 8.32 (d, J = 5.27 Hz, 1 H), 8.49 (s, 1 H) | 0.026525 | >3769 |
| 102 | N | C—Cl | (CH₂)₃S(O)₂CH₃ | cyclopropyl | N | ¹H NMR (400 MHz, DMSO-d₆) δ ppm 0.88-0.95 (m, 2 H) 1.03-1.08 (m, 2 H) 2.19 (m, J = 7.65, 7.65, 7.65, 7.65 Hz, 2 H) 2.95-3.04 (m, 4 H) 3.23 (t, J = 8.30 Hz, 2 H) 4.53 (t, J = 7.40 Hz, 2 H) 5.48 (s, 2 H) 7.30 (d, J = 5.27 Hz, 1 H) 7.39 (d, J = 8.28 Hz, 1 H) 8.20 (d, J = 8.53 Hz, 1 H) 8.27 (d, J = 5.27 Hz, 1 H) 8.43 (s, 1 H) | 0.00427 | >23420 |
| 103 | N | C—Cl | (CH₂)₃S(O)₂CH₃ | cyclopropyl | C—F | ¹H NMR (400 MHz, CHLOROFORM-d) δ ppm 0.90 (m, J = 2.51 Hz, 2 H) 1.00-1.10 (m, 2 H) 2.18 (m, J = 14.62, 7.37, 7.37 Hz, 2 H) 2.94 (tt, J = 6.80, 3.40 Hz, 1 H) 2.99 (s, 3 H) 3.22 (t, J = 7.50 Hz, 2 H) 4.52 (t, J = 7.15 Hz, 2 H) 5.41 (s, 2 H) 6.86-7.01 (m, 1 H) 7.15-7.28 (m, 2 H) 7.39 (d, J = 8.28 Hz, 1 H) 8.19 (d, J = 8.53 Hz, 1 H) | 0.003746 | >26698 |
| 45 | N | C—Cl | (CH₂)₄F chain | oxetanyl | N | ¹H NMR (400 MHz, DMSO-d₆) δ ppm 1.58-1.90 (m, 4 H) 4.36-4.56 (m, 4 H) 4.97 (t, J = 7.50 Hz, 2 H) 5.08 (t, J = 6.53 Hz, 2 H) 5.52 (s, 2 H) 5.57 (m, J = 6.27, 6.27 Hz, 1 H) 7.37 (d, J = 8.53 Hz, 1 H) 7.55 (d, J = 5.27 Hz, 1 H) 8.20 (d, J = 8.53 Hz, 1 H) 8.32 (d, J = 5.52 Hz, 1 H) 8.50 (s, 1 H) | 0.008491 | >11777 |

TABLE 4-continued

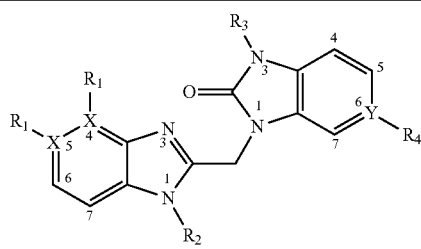

| | X4—R1 | X5—R1 | R2 | R3 | Y—R4 | ¹H NMR | WT activity EC50 (μM) | SI CC50/ EC50 |
|---|---|---|---|---|---|---|---|---|
| 46 | N | C—Cl | (CH2)4-SO2CH3 | cyclopropyl | C—F | ¹H NMR (400 MHz, DMSO-d6) δ ppm 0.85-0.95 (m, 2 H) 1.04 (m, J = 5.77 Hz, 2 H) 1.65-1.98 (m, 4 H) 2.87-3.04 (m, 4 H) 3.18 (t, J = 7.40 Hz, 2 H) 4.43 (t, J = 6.78 Hz, 2 H) 5.40 (s, 2 H) 6.93 (m, J = 18.20, 1.88 Hz, 1 H) 7.17 (dd, J = 9.16, 1.88 Hz, 1 H) 7.23 (dd, J = 8.53, 4.52 Hz, 1 H) 7.37 (d, J = 8.53 Hz, 1 H) 8.20 (d, J = 8.53 Hz, 1 H) | 0.011567 | >8645 |
| 47 | N | C—Cl | (CH2)4-SO2CH3 | cyclopropyl | N | ¹H NMR (400 MHz, DMSO-d6) δ ppm 0.92 (m, J = 2.51 Hz, 2 H) 1.03-1.12 (m, 2 H) 1.68-1.95 (m, 4 H) 2.95 (s, 3 H) 3.01 (tt, J = 6.87, 3.67 Hz, 1 H) 3.19 (t, J = 7.30 Hz, 2 H) 4.44 (t, J = 7.15 Hz, 2 H) 5.47 (s, 2 H) 7.30 (d, J = 5.02 Hz, 1 H) 7.37 (d, J = 8.53 Hz, 1 H) 8.21 (d, J = 8.53 Hz, 1 H) 8.27 (d, J = 5.02 Hz, 1 H) 8.41 (s, 1 H) | 0.01063 | >9407 |
| 48 | N | C—Cl | (CH2)4-SO2CH3 | cyclopropyl | C—H | ¹H NMR (400 MHz, DMSO-d6) δ ppm 0.87-0.96 (m, 2 H) 1.02-1.11 (m, 2 H) 1.65-1.89 (m, 4 H) 2.89-3.01 (m, 4 H) 3.12-3.22 (m, 2 H) 4.43 (t, J = 6.90 Hz, 2 H) 5.40 (s, 2 H) 6.97-7.15 (m, 2 H) 7.21 (d, J = 7.53 Hz, 1 H) 7.26 (d, J = 7.53 Hz, 1 H) 7.36 (d, J = 8.28 Hz, 1 H) 8.19 (d, J = 8.53 Hz, 1 H) | 0.003443 | >29042 |
| 50 | N | C—H | (CH2)4-OH | H | N | ¹H NMR (400 MHz, DMSO-d6) δ ppm 1.38-1.51 (m, 2 H) 1.65-1.77 (m, 2 H) 3.41 (t, J = 6.40 Hz, 2 H) 4.38 (t, J = 7.53 Hz, 2 H) 5.44 (s, 2 H) 7.08 (dd, J = 5.27, 0.75 Hz, 1 H) 7.26 (dd, J = 8.16, 4.64 Hz, 1 H) 8.05 (dd, J = 8.16, 1.63 Hz, 1 H) 8.17 (d, J = 5.27 Hz, 1 H) 8.35 (d, J = 0.50 Hz, 1 H) 8.37 (dd, J = 4.77, 1.51 Hz, 1 H) | 0.044745 | >2234 |
| 51 | N | C—H | (CH2)4-OH | cyclopropyl | N | ¹H NMR (400 MHz, DMSO-d6) δ ppm 0.87-0.97 (m, 2 H) 1.09 (m, J = 7.00, 7.00 Hz, 2 H) 1.35-1.52 (m, 2 H) 1.64-1.76 (m, 2 H) 3.00 (tt, J = 6.90, 3.51 Hz, 1 H) 3.16-3.36 (m, 2 H) 4.38 (t, J = 7.40 Hz, 2 H) 5.45 (s, 2 H) 7.21- | 0.009607 | >10408 |

TABLE 4-continued

| | X4—R1 | X5—R1 | R2 | R3 | Y—R4 | ¹H NMR | WT activity EC50 (μM) | SI CC50/EC50 |
|---|---|---|---|---|---|---|---|---|
| | | | | | | 7.34 (m, 2 H) 8.05 (dd, J = 8.03, 1.25 Hz, 1 H) 8.26 (d, J = 5.27 Hz, 1 H) 8.37 (dd, J = 4.52, 1.25 Hz, 1 H) 8.41 (s, 1 H) | | |
| 54 | N | C—Cl | (methylsulfonyl propyl) | cyclopropyl | C—H | ¹H NMR (400 MHz, CHLOROFORM-d) δ ppm 0.98-1.05 (m, 2 H), 1.10-1.17 (m, 2 H), 2.18-2.29 (m, 2 H), 2.88-2.95 (m, 1 H), 2.92 (s, 3 H), 3.12 (t, J = 7.3 Hz, 2 H), 4.58-4.65 (m, 2 H), 5.35 (s, 2 H), 7.09-7.15 (m, 2 H), 7.17-7.22 (m, 1 H), 7.24 (d, J = 8.3 Hz, 1 H), 7.52-7.57 (m, 1 H), 7.74 (d, J = 8.5 Hz, 1 H) | 0.00285 | >35091 |
| 55 | N | C—Cl | (4-fluorobutyl) | cyclopropyl | C—COOEt | ¹H NMR (400 MHz, CHLOROFORM-d) δ ppm 0.99-1.06 (m, 2 H), 1.12-1.20 (m, 2 H), 1.41 (t, J = 7.0 Hz, 3 H), 1.68-1.76 (m, 1 H), 1.77-1.89 (m, 3 H), 2.88-2.96 (m, 1 H), 4.37-4.45 (m, 3 H), 4.45-4.5 (m, 2 H), 4.53 (t, J = 5.3 Hz, 1 H), 5.38 (s, 2 H), 7.23-7.34 (m, 2 H), 7.62 (d, J = 8.3 Hz, 1 H), 7.88 (dd, J = 8.3, 1.5 Hz, 1 H), 8.06 (d, J = 1.3 Hz, 1 H) | 0.027295 | >3663 |
| 56 | N | C—Cl | (4-fluorobutyl) | propyl | C—COOEt | ¹H NMR (400 MHz, CHLOROFORM-d) δ ppm 0.99 (t, J = 7.4 Hz, 3 H), 1.41 (t, J = 7.2 Hz, 3 H), 1.69-1.89 (m, 6 H), 3.88 (t, J = 7.3 Hz, 2 H), 4.33-4.47 (m, 5 H), 4.52 (t, J = 5.3 Hz, 1 H), 5.42 (s, 2 H), 7.01 (d, J = 8.3 Hz, 1 H), 7.23 (d, J = 8.5 Hz, 1 H), 7.62 (d, J = 8.3 Hz, 1 H), 7.87 (dd, J = 8.3, 1.5 Hz, 1 H), 8.09 (d, J = 1.5 Hz, 1 H) | 0.036033 | >2775 |
| 57 | N | C—Cl | (4-fluorobutyl) | cyclopropyl | C—COOH | ¹H NMR (400 MHz, DMSO-d6) δ ppm 0.87-0.97 (m, 2 H), 1.05-1.14 (m, 2 H), 1.59-1.87 (m, 4 H), 3.00-3.05 (m, 1 H), 4.37-4.47 (m, 3 H), 4.51 (t, J = 5.5 Hz, 1 H), 5.48 (s, 2 H), 7.35 (dd, J = 8.4, 4.9 Hz, 2 H), 7.78 (dd, J = 8.3, 1.5 Hz, 1 H), 7.82 (d, J = 1.3 Hz, 1 H), 8.18 (d, J = 8.5 Hz, 1 H), 12.80 (br. s, 1 H) | 0.018249 | >5479 |

TABLE 4-continued

| | $X_4$—$R_1$ | $X_5$—$R_1$ | $R_2$ | $R_3$ | Y—$R_4$ | $^1$H NMR | WT activity $EC_{50}$ (μM) | SI $CC_{50}$/$EC_{50}$ |
|---|---|---|---|---|---|---|---|---|
| 58 | N | C—Cl | pentyl-OH | cyclopropyl | C—F | $^1$H NMR (400 MHz, DMSO-$d_6$) δ ppm 0.86-0.94 (m, 2 H), 1.02-1.09 (m, 2 H), 1.37-1.50 (m, 2 H), 1.65-1.77 (m, 2 H), 2.90-2.99 (m, 1 H), 3.36-3.43 (m, 2 H), 4.35-4.43 (m, 2 H), 4.47 (t, J = 5.0 Hz, 1 H), 5.39 (s, 2 H), 6.89-6.97 (m, 1 H), 7.16 (dd, J = 9.0, 2.5 Hz, 1 H), 7.22 (dd, J = 8.7, 4.6 Hz, 1 H), 7.35 (d, J = 8.5 Hz, 1 H), 8.16 (d, J = 8.3 Hz, 1 H) | 0.003967 | >25206 |
| 43 | N | C—H | butyl-CHF$_2$ | cyclopropyl | N | $^1$H NMR (400 MHz, DMSO-$d_6$) δ ppm 0.88-0.96 (m, 2 H) 1.04-1.13 (m, 2 H) 1.73-2.01 (m, 4 H) 2.99 (tt, J = 6.96, 3.58 Hz, 1 H) 4.43 (t, J = 7.15 Hz, 2 H) 5.46 (s, 2 H) 5.93-6.28 (m, 1 H) 7.23-7.36 (m, 2 H) 8.09 (dd, J = 8.16, 1.38 Hz, 1 H) 8.27 (d, J = 5.27 Hz, 1 H) 8.38 (dd, J = 4.64, 1.38 Hz, 1 H) 8.43 (s, 1 H) | 0.00791 | 7161 |
| 64 | N | C—Cl | pentyl-OC(O)CH$_3$ | cyclopropyl | N | $^1$H NMR (360 MHz, DMSO-$d_6$) δ ppm 0.88-0.98 (m, 2 H), 1.01-1.11 (m, 2 H), 1.52-1.66 (m, 2 H), 1.69-1.82 (m, 2 H), 1.99 (s, 3 H), 3.00 (tt, J = 7.0, 3.5 Hz, 1 H), 4.01 (t, J = 6.4 Hz, 2 H), 4.42 (t, J = 7.3 Hz, 2 H), 5.47 (s, 2 H), 7.31 (d, J = 5.5 Hz, 1 H), 7.37 (d, J = 8.4 Hz, 1 H), 8.20 (d, J = 8.4 Hz, 1 H), 8.27 (d, J = 5.5 Hz, 1 H), 8.41 (s, 1 H) | 0.005538 | >18058 |
| 65 | N | C—Cl | pentyl-OC(O)CH(CH$_3$)$_2$ | cyclopropyl | N | $^1$H NMR (360 MHz, DMSO-$d_6$) δ ppm 0.87-0.95 (m, 2 H), 1.01-1.12 (m, 2 H), 1.05 (d, J = 7.0 Hz, 6 H), 1.53-1.68 (m, 2 H), 1.69-1.84 (m, 2 H), 2.43-2.56 (m, 1 H), 3.00 (tt, J = 6.9, 3.6 Hz, 1 H), 4.02 (t, J = 6.4 Hz, 2 H), 4.43 (t, J = 7.3 Hz, 2 H), 5.47 (s, 2 H), 7.31 (d, J = 5.1 Hz, 1 H), 7.37 (d, J = 8.4 Hz, 1 H), 8.20 (d, J = 8.4 Hz, 1 H), 8.27 (d, J = 5.1 Hz, 1 H), 8.41 (s, 1 H) | 0.005522 | >18110 |

TABLE 4-continued

| | X4—R1 | X5—R1 | R2 | R3 | Y—R4 | ¹H NMR | WT activity EC₅₀ (μM) | SI CC₅₀/ EC₅₀ |
|---|---|---|---|---|---|---|---|---|
| 66 | N | C—Cl | (alkyl chain with phthalimide) | cyclopropyl | N | ¹H NMR (400 MHz, DMSO-d₆) δ ppm 0.82-0.96 (m, 2 H) 0.99-1.13 (m, 2 H) 1.55-1.67 (m, 2 H) 1.73 (m, J = 6.78 Hz, 2 H) 2.90-3.04 (m, 1 H) 3.59 (t, J = 6.02 Hz, 2 H) 4.41 (t, J = 6.78 Hz, 2 H) 5.45 (s, 2 H) 7.21 (d, J = 4.77 Hz, 1 H) 7.33 (d, J = 8.28 Hz, 1 H) 7.78-7.94 (m, 4 H) 8.15-8.26 (m, 2 H) 8.38 (s, 1 H) | 0.005904 | >16939 |
| 67 | N | C—Cl | (alkyl chain with OH, methyl branch) | cyclopropyl | N | ¹H NMR (400 MHz, CHLOROFORM-d) δ ppm 0.99-1.05 (m, 2 H) 1.13-1.22 (m, 5 H) 1.43-1.57 (m, 2 H) 1.77-1.91 (m, 2 H) 2.11 (br. s, 1 H) 2.89-2.98 (m, 1 H) 3.81-3.90 (m, 1 H) 4.32-4.50 (m, 2 H) 5.40 (s, 2 H) 7.13 (dd, J = 5.27, 0.75 Hz, 1 H) 7.23 (d, J = 8.53 Hz, 1 H) 7.65 (d, J = 8.28 Hz, 1 H) 8.34 (d, J = 5.27 Hz, 1 H) 8.75 (s, 1 H) | 0.007909 | >12643 |
| 68 | N | C—Cl | (alkyl chain with HN-C(=O)-OMe carbamate) | cyclopropyl | N | ¹H NMR (400 MHz, DMSO-d₆) δ ppm 0.83-1.00 (m, 2 H) 1.09 (m, J = 5.52 Hz, 2 H) 1.36-1.53 (m, 2 H) 1.61-1.81 (m, 2 H) 3.01 (m, J = 3.76 Hz, 3 H) 3.51 (s, 3 H) 4.39 (t, J = 6.02 Hz, 2 H) 5.46 (s, 2 H) 7.05-7.19 (m, 1 H) 7.30 (d, J = 4.77 Hz, 1 H) 7.36 (d, J = 8.28 Hz, 1 H) 8.18 (d, J = 8.53 Hz, 1 H) 8.27 (d, J = 5.02 Hz, 1 H) 8.40 (s, 1 H) | 0.008191 | >12208 |
| 69 | N | C—F | (alkyl chain with CF₃) | cyclopropyl | N | ¹H NMR (400 MHz, DMSO-d₆) δ ppm 0.87-0.94 (m, 2 H) 1.03-1.10 (m, 2 H) 1.89-2.01 (m, 2 H) 2.31-2.46 (m, 2 H) 2.98 (tt, J = 6.96, 3.58 Hz, 1 H) 4.48 (t, J = 7.78 Hz, 2 H) 5.46 (s, 2 H) 7.08 (dd, J = 8.53, 1.00 Hz, 1 H) 7.30 (dd, J = 5.27, 0.75 Hz, 1 H) 8.27 (d, J = 5.27 Hz, 1 H) 8.32 (dd, J = 8.53, 7.28 Hz, 1 H) 8.44 (d, J = 0.50 Hz, 1 H) | 0.075842 | >1318 |

TABLE 4-continued

| | X4—R1 | X5—R1 | R2 | R3 | Y—R4 | ¹H NMR | WT activity EC50 (µM) | SI CC50/ EC50 |
|---|---|---|---|---|---|---|---|---|
| 70 | N | C—H | (propyl-O-CF3 chain) | cyclopropyl | N | 1H NMR (400 MHz, CHLOROFORM-d) δ ppm 0.96-1.04 (m, 2 H) 1.13-1.22 (m, 2 H) 2.09-2.22 (m, 2 H) 2.91 (tt, J = 7.03, 3.64 Hz, 1 H) 4.02 (t, J = 5.77 Hz, 2 H) 4.56 (t, J = 7.30 Hz, 1 H) 5.40 (s, 2 H) 7.13 (dd, J = 5.27, 0.50 Hz, 1 H) 7.24 (dd, J = 8.03, 4.77 Hz, 1 H) 7.69 (dd, J = 8.03, 1.51 Hz, 1 H) 8.35 (d, J = 5.27 Hz, 1 H) 8.56 (dd, J = 4.77, 1.51 Hz, 1 H) 8.78 (d, J = 0.75 Hz, 1 H) | 0.010969 | >9116 |
| 71 | N | C—Cl | (butyl-CF3 chain) | CH2CF3 | N | 1H NMR (400 MHz, DMSO-d6) δ ppm 1.93-2.07 (m, 2 H) 2.30-2.47 (m, 2 H) 4.44-4.55 (m, 2 H) 4.85-4.97 (m, 2 H) 5.58 (s, 2 H) 7.39 (d, J = 8.53 Hz, 1H) 7.46 (d, J = 5.27 Hz, 1 H) 8.23 (d, J = 8.28 Hz, 1 H) 8.34 (d, J = 5.27 Hz, 1 H) 8.51 (s, 1 H) | 0.000923 | >108383 |
| 72 | N | C—H | (butyl-CF3 chain) | CH2CF3 | N | 1H NMR (400 MHz, CHLOROFORM-d) δ ppm 1.87-2.00 (m, 2 H) 2.21 (dt, J = 10.35, 7.75 Hz, 2 H) 4.41-4.46 (m, 2 H) 4.49 (q, J = 8.53 Hz, 2 H) 5.48 (s, 2H) 7.03 (d, J = 5.52 Hz, 1 H) 7.25-7.29 (m, 1 H) 7.67 (dd, J = 8.03, 1.51 Hz, 1 H) 8.42 (d, J = 5.27 Hz, 1 H) 8.60 (dd, J = 4.64, 1.38 Hz, 1 H) 8.90 (s, 1 H) | 0.003614 | >2766 |
| 73 | N | C—Cl | (butyl-NHC(O)O-phenyl) | cyclopropyl | N | ¹H NMR (400 MHz, DMSO-d6) δ ppm 0.88-0.96 (m, 2 H) 1.03-1.12 (m, 2 H) 1.46-1.59 (m, 2 H) 1.70-1.84 (m, 2 H) 3.00 (tt, J = 6.96, 3.58 Hz, 1 H) 3.11 (q, J = 6.61 Hz, 2 H) 4.43 (t, J = 7.53 Hz, 2 H) 5.47 (s, 2 H) 7.03-7.12 (m, 2 H) 7.15-7.23 (m, 1 H) 7.27-7.32 (m, 1 H) 7.32-7.40 (m, 3 H) 7.77 (t, J = 5.65 Hz, 1 H) 8.20 (d, J = 8.53 Hz, 1 H) 8.27 (d, J = 5.27 Hz, 1 H) 8.41 (s, 1 H) | 0.015206 | >6576 |

TABLE 4-continued

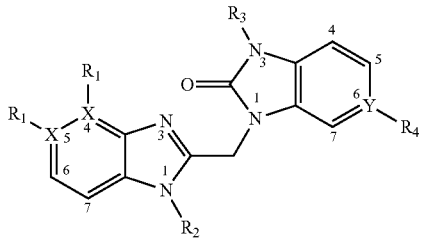

| | X4—R1 | X5—R1 | R2 | R3 | Y—R4 | 1H NMR | WT activity EC50 (μM) | SI CC50/EC50 |
|---|---|---|---|---|---|---|---|---|
| 74 | N | C—Cl | (n-butyl urea) | cyclopropyl | N | 1H NMR (400 MHz, DMSO-d6) δ ppm 0.87-0.97 (m, 2 H) 1.00-1.14 (m, 2 H) 1.40 (quin, J = 7.09 Hz, 2 H) 1.61-1.77 (m, 2 H) 2.93-3.07 (m, 3 H) 4.40 (t, J = 7.53 Hz, 2 H) 5.38 (s, 2 H) 5.46 (s, 2 H) 5.98 (t, J = 5.77 Hz, 1 H) 7.30 (d, J = 5.27 Hz, 1 H) 7.35 (d, J = 8.53 Hz, 1 H) 8.20 (d, J = 8.53 Hz, 1 H) 8.27 (d, J = 5.02 Hz, 1 H) 8.40 (s, 1 H) | 0.005006 | >1997 |
| 75 | N | C—Cl | (hydroxy-dimethyl butyl) | cyclopropyl | N | 1H NMR (400 MHz, CHLOROFORM-d) δ ppm 0.97-1.05 (m, 2 H), 1.11-1.22 (m, 2 H), 1.17 (s, 6 H), 1.43-1.53 (m, 2 H), 1.74 (br. s., 1 H), 1.79-1.91 (m, 2 H), 2.82-3.05 (m, 1 H), 4.40 (t, J = 7.5 Hz, 2 H), 5.39 (s, 2 H), 7.11 (d, J = 5.0 Hz, 1 H), 7.20 (d, J = 8.3 Hz, 1 H), 7.64 (d, J = 8.3 Hz, 1 H), 8.31 (d, J = 5.0 Hz, 1 H), 8.70 (s, 1 H) | 0.001579 | >63325 |
| 76 | N | C—Cl | (fluoroethyl carbamate) | cyclopropyl | N | 1H NMR (400 MHz, DMSO-d6) δ ppm 0.88-0.96 (m, 2 H) 1.04-1.11 (m, 2H) 1.45 (m, J = 7.15, 7.15, 7.15, 7.15 Hz, 2 H) 1.64-1.77 (m, 2 H) 2.96-3.08 (m, 3 H) 4.17 (dt, J = 30.62, 4.00 Hz, 2 H) 4.39 (t, J = 7.40 Hz, 2 H) 4.56 (dt, J = 47.93, 3.80 Hz, 2 H) 5.46 (s, 2 H) 7.25-7.39 (m, 3 H) 8.18 (d, J = 8.53 Hz, 1 H) 8.27 (d, J = 5.27 Hz, 1 H) 8.40 (s, 1 H) | 0.004078 | >24518 |
| 77 | N | C—Cl | (isopropyl carbamate) | cyclopropyl | N | 1H NMR (400 MHz, DMSO-d6) δ ppm 0.87-0.96 (m, 2 H) 1.03-1.11 (m, 2 H) 1.14 (d, J = 6.02 Hz, 6 H) 1.43 (m, J = 6.90, 6.90, 6.90, 6.90 Hz, 2 H) 1.62-1.77 (m, 2 H) 2.90-3.09 (m, 3 H) 4.39 (t, J = 7.28 Hz, 2 H) 4.72 (dquin, J = 12.31, 5.96, 5.96, 5.96, 5.96 Hz, 1 H) 5.46 (s, 2 H) 7.02 (t, J = 5.27 Hz, 1 H) 7.30 (d, J = 5.02 Hz, 1 H) 7.35 (d, J = 8.53 Hz, 1 H) 8.18 (d, J = 8.53 Hz, 1 H) 8.27 (d, J = 5.27 Hz, 1 H) 8.40 (s, 1 H) | | |

TABLE 4-continued

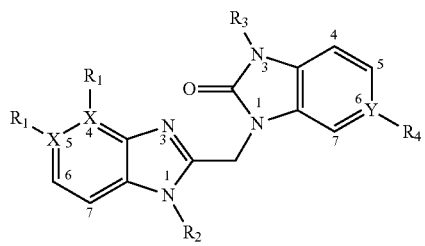

| | X4—R1 | X5—R1 | R2 | R3 | Y—R4 | 1H NMR | WT activity EC50 (μM) | SI CC50/ EC50 |
|---|---|---|---|---|---|---|---|---|
| 78 | N | C—Cl | (cyclopentyl carbamate chain) | (cyclopropyl) | N | 1H NMR (400 MHz, DMSO-d6) δ ppm 0.89-0.97 (m, 2 H), 1.04-1.13 (m, 2 H), 1.29-1.41 (m, 2 H), 1.41-1.51 (m, 2 H), 1.53-1.66 (m, 4 H), 1.68-1.87 (m, 4 H), 2.96-3.06 (m, 1 H), 3.68-3.84 (m, 1 H), 3.97 (t, J = 6.3 Hz, 2 H), 4.45 (t, J = 7.3 Hz, 2 H), 5.47 (s, 2 H), 7.08 (d, J = 7.0 Hz, 1 H), 7.30 (dd, J = 5.3, 0.5 Hz, 1 H), 7.36 (d, J = 8.5 Hz, 1 H), 8.19 (d, J = 8.5 Hz, 1 H), 8.27 (d, J = 5.3, 1 H), 8.41 (s, 1 H) | 0.005732 | 14406 |
| 79 | N | C—Cl | (4-methoxyphenyl carbamate chain) | (cyclopropyl) | N | 1H NMR (400 MHz, DMSO-d6) δ ppm 0.87-0.95 (m, 2 H), 1.02-1.10 (m, 2 H), 1.60-1.72 (m, 2 H), 1.75-1.88 (m, 2 H), 2.99-3.02 (m, 1 H), 3.69 (s, 3 H), 4.09 (t, J = 6.5 Hz, 2 H), 4.45 (t, J = 7.4 Hz, 2 H), 5.47 (s, 2 H), 6.80-6.88 (m, 2 H), 7.28 (dd, J = 5.3, 0.8 Hz, 1 H), 7.30-7.40 (m, 3 H), 8.20 (d, J = 8.5 Hz, 1 H), 8.26 (d, J = 5.0 Hz, 1 H), 8.41 (s, 1 H), 9.37 (br. s., 1 H) | 0.023345 | 1711 |
| 80 | N | C—Cl | (methyl-benzothiophene-dioxide amine chain) | (cyclopropyl) | N | 1H NMR (400 MHz, DMSO-d6) δ ppm 0.85-0.94 (m, 2 H) 1.00-1.10 (m, 2 H) 1.64 (m, J = 7.28 Hz, 2 H) 1.82 (m, J = 7.72, 7.72, 7.72, 7.72 Hz, 2 H) 2.06 (s, 3 H) 2.96 (tt, J = 6.96, 3.58 Hz, 1 H) 3.44 (q, J = 6.78 Hz, 2 H) 4.45 (t, J = 7.40 Hz, 2 H) 5.47 (s, 2 H) 6.69 (t, J = 5.90 Hz, 1 H) 7.24 (dd, J = 5.27, 0.50 Hz, 1 H) 7.35 (d, J = 8.53 Hz, 1 H) 7.57 (td, J = 7.50, 0.75 Hz, 1 H) 7.67 (td, J = 7.65, 1.25 Hz, 1 H) 7.75 (dd, J = 7.40, 0.63 Hz, 1 H) 7.86 (d, J = 7.78 Hz, 1 H) 8.19 (d, J = 8.53 Hz, 1 H) 8.24 (d, J = 5.27 Hz, 1 H) 8.42 (s, 1 H) | 0.010386 | >9628 |

TABLE 4-continued

| | X₄—R₁ | X5—R₁ | R₂ | R₃ | Y—R₄ | ¹H NMR | WT activity EC₅₀ (µM) | SI CC₅₀/ EC₅₀ |
|---|---|---|---|---|---|---|---|---|
| 81 | N | C—H | (alkyl chain with HN-C(=O)-O-isopropyl carbamate) | cyclopropyl | N | ¹H NMR (400 MHz, DMSO-d₆) δ ppm 0.87-0.98 (m, 2 H) 1.08 (m, J = 5.00 Hz, 2 H) 1.14 (d, J = 5.27 Hz, 6 H) 1.37-1.54 (m, 2 H) 1.61-1.78 (m, 2 H) 2.89-3.08 (m, 3 H) 4.37 (m, J = 5.50, 5.50 Hz, 2 H) 4.63-4.85 (m, 1 H) 5.45 (s, 2 H) 6.96-7.12 (m, 1 H) 7.26 (dd, J = 7.40, 4.64 Hz, 1 H) 7.30 (d, J = 4.77 Hz, 1 H) 8.07 (d, J = 7.53 Hz, 1 H) 8.26 (d, J = 4.77 Hz, 1 H) 8.37 (d, J = 3.26 Hz, 1 H) 8.41 (s, 1 H) | 0.072449 | >1380 |
| 82 | N | C—Cl | (alkyl chain with HN-C(=O)-O-cyclopentyl carbamate) | cyclopropyl | N | ¹H NMR (400 MHz, DMSO-d₆) δ ppm 0.87-0.97 (m, 2 H) 1.02-1.14 (m, 2 H) 1.34-1.87 (m, 12 H) 3.00 (m, J = 6.80, 3.80 Hz, 3 H) 4.39 (t, J = 7.15 Hz, 2 H) 4.86-4.99 (m, 1 H) 5.46 (s, 2 H) 7.02 (t, J = 5.02 Hz, 1 H) 7.30 (d, J = 5.27 Hz, 1 H) 7.35 (d, J = 8.53 Hz, 1 H) 8.18 (d, J = 8.28 Hz, 1 H) 8.27 (d, J = 5.02 Hz, 1 H) 8.40 (s, 1 H) | 0.017084 | 5649 |
| 83 | N | C—Cl | (alkyl chain with O-C(=O)-NH-(2-CF₃-4-F-phenyl) carbamate) | cyclopropyl | N | ¹H NMR (400 MHz, DMSO-d₆) δ ppm 0.87-0.96 (m, 2 H), 1.02-1.11 (m, 2 H), 1.58-1.71 (m, 2 H), 1.79-1.82 (m, 2 H), 2.99-3.05 (m, 1 H), 4.08 (t, J = 6.5 Hz, 2 H), 4.44 (t, J = 7.4 Hz, 2 H), 5.46 (s, 2 H), 7.30 (dd, J = 5.3, 0.5 Hz, 1 H), 7.35 (d, J = 8.5 Hz, 1 H), 7.49-7.55 (m, 2 H), 7.61 (dd, J = 8.8, 2.5 Hz, 1 H), 8.17 (d, J = 8.3 Hz, 1 H), 8.27 (d, J = 5.3 Hz, 1 H), 8.40 (s, 1 H), 9.07 (s, 1 H) | 0.013992 | 4731 |
| 84 | N | C—Cl | (alkyl chain with O-C(=O)-NH-(3-Cl-4-F-phenyl) carbamate) | cyclopropyl | N | ¹H NMR (400 MHz, DMSO-d₆) δ ppm 0.84-0.97 (m, 2 H), 1.06-1.15 (m, 2 H), 1.68-1.72 (m, 2 H), 1.81-1.9 (m, 2 H), 2.92-3.07 (m, 1 H), 4.13 (t, J = 6.1 Hz, 2 H), 4.46 (t, J = 7.0 Hz, 2 H), 5.47 (s, 2 H), 7.21-7.43 (m, 4 H), 7.68 (d, J = 5.3 Hz, 1 H), 8.20 (d, J = 8.5 Hz, 1 H), 8.26 (d, J = 5.3 Hz, 1 H), 8.41 (s, 1 H), 9.82 (br. s., 1 H) | 0.018911 | 354 |

TABLE 4-continued

| | X4—R1 | X5—R1 | R2 | R3 | Y—R4 | ¹H NMR | WT activity EC₅₀ (μM) | SI CC₅₀/EC₅₀ |
|---|---|---|---|---|---|---|---|---|
| 85 | N | C—H | (n-pentyl) | CH₂CF₃ (2,2,2-trifluoroethyl-like, shown as CH₂ with CF₃ and F) | N | ¹H NMR (400 MHz, DMSO-d₆) δ ppm 1.63-1.90 (m, 4 H) 4.36-4.57 (m, 4 H) 4.92 (q, J = 9.20 Hz, 2 H) 5.56 (s, 2 H) 7.27 (dd, J = 8.16, 4.64 Hz, 1 H) 7.46 (d, J = 5.02 Hz, 1 H) 8.09 (dd, J = 8.03, 1.25 Hz, 1 H) 8.33 (d, J = 5.27 Hz, 1 H) 8.37 (dd, J = 4.64, 1.13 Hz, 1 H) 8.51 (s, 1 H) | 0.008536 | 1436 |
| 86 | N | C—Cl | (butyl-O-C(O)-NH-C₆H₄-Cl carbamate) | cyclopropyl | N | ¹H NMR (400 MHz, DMSO-d₆) δ ppm 0.87-0.96 (m, 2 H), 1.02-1.11 (m, 2 H), 1.61-1.73 (m, 2 H), 1.83 (m, 2 H), 2.99 (m, 1 H), 4.12 (t, J = 6.5 Hz, 2 H), 4.46 (t, J = 7.3 Hz, 2 H), 5.47 (s, 2 H), 7.28 (dd, J = 5.3, 0.8 Hz, 1 H), 7.29-7.33 (m, 2 H), 7.35 (d, J = 8.3 Hz, 1 H), 7.46 (d, J = 8.8 Hz, 2 H), 8.20 (d, J = 8.5 Hz, 1 H), 8.26 (d, J = 5.0 Hz, 1 H), 8.41 (s, 1 H), 9.72 (br. s., 1 H) | 0.03677 | 263 |
| 87 | N | C—Cl | (4,4,4-trifluorobutyl) | CH₂CF₃ | C—F | ¹H NMR (400 MHz, CHLOROFORM-d) δ ppm 1.85-1.97 (m, 2 H) 2.14-2.29 (m, 2 H) 4.38-4.54 (m, 4 H) 5.40 (s, 2 H) 6.87 (td, J = 9.03, 2.51 Hz, 1 H) 6.98 (dd, J = 8.53, 4.02 Hz, 1 H) 7.30 (d, J = 8.53 Hz, 1 H) 7.47 (dd, J = 8.16, 2.38 Hz, 1 H) 7.64 (d, J = 8.53 Hz, 1 H) | 0.002038 | >49069 |
| 88 | N | C—Cl | (2,2-dimethyl-hydroxy alkyl) | cyclopropyl | N | ¹H NMR (400 MHz, DMSO-d₆) δ ppm 0.82-1.01 (m, 8 H) 1.08 (m, J = 5.77 Hz, 2 H) 1.49-1.67 (m, 2 H) 2.96-3.06 (m, 0 H) 3.23 (d, J = 2.26 Hz, 2 H) 4.30-4.46 (m, 2 H) 4.69-4.83 (m, 0 H) 5.46 (s, 2 H) 7.34 (d, J = 5.52 Hz, 1 H) 7.36 (d, J = 8.28 Hz, 1 H) 8.07 (d, J = 8.28 Hz, 1 H) 8.29 (d, J = 5.02 Hz, 1 H) 8.43 (s, 1 H) | 0.011068 | >4517 |
| 89 | N | C—H | (4,4,4-trifluorobutyl) | CH₂CF₃ | C—F | ¹H NMR (400 MHz, CHLOROFORM-d) δ ppm 1.82-1.99 (m, 2 H) 2.12-2.30 (m, 2 H) 4.39-4.55 (m, 4 H) 5.43 (s, 2 H) 6.80-6.90 (m, 1 H) 6.94-7.05 (m, 1 H) 7.19-7.33 (m, 1 H) 7.50 (dd, J = 8.16, 2.38 Hz, 1 H) 7.68 (dd, J = 8.28, 1.51 Hz, 1 H) 8.61 (dd, J = 4.77, 1.51 Hz, 1 H) | 0.049076 | >2037 |

TABLE 4-continued

| | X4—R1 | X5—R1 | R2 | R3 | Y—R4 | 1H NMR | WT activity EC50 (µM) | SI CC50/EC50 |
|---|---|---|---|---|---|---|---|---|
| 90 | N | C—Cl | isohexyl | CH2CF3 | N | 1H NMR (400 MHz, CHLOROFORM-d) δ ppm 1.00 (d, J = 6.52 Hz, 6 H), 1.52-1.64 (m, 2 H), 1.72 (tt, J = 13.21, 6.62 Hz, 1 H), 4.26-4.40 (m, 2 H), 4.50 (q, J = 8.53 Hz, 2 H), 5.43 (s, 2 H), 7.02 (d, J = 5.27 Hz, 1 H), 7.23 (d, J = 8.28 Hz, 1 H), 7.62 (d, J = 8.28 Hz, 1 H), 8.39 (d, J = 5.27 Hz, 1 H), 8.78 (s, 1 H) | 0.0026 | 36156 |
| 91 | N | C—H | 3-phenylpropyl | cyclopropyl | N | 1H NMR (400 MHz, CHLOROFORM-d) δ ppm 0.88-1.05 (m, 2 H) 1.11-1.22 (m, 2 H) 1.90-2.11 (m, 2 H) 2.68 (t, J = 7.78 Hz, 2 H) 2.80-3.01 (m, 1 H) 4.40 (t, J = 7.80 Hz, 2 H) 5.38 (s, 2 H) 7.08-7.14 (m, 3 H) 7.15-7.25 (m, 2 H) 7.27-7.32 (m, 2 H) 7.50 (dd, J = 8.03, 1.51 Hz, 1 H) 8.35 (d, J = 5.27 Hz, 1 H) 8.55 (dd, J = 4.77, 1.51 Hz, 1 H) 8.75 (s, 1 H) | 0.01216 | >8223 |
| 92 | N | C—Cl | isohexyl | CH2CF3 | C—F | 1H NMR (400 MHz, CHLOROFORM-d) δ ppm 0.99 (d, J = 6.52 Hz, 6 H), 1.55 (m, J = 15.80, 7.50 Hz, 2 H), 1.62-1.78 (m, 1 H), 4.36 (m, J = 16.31 Hz, 2 H), 4.46 (q, J = 8.53 Hz, 2 H), 5.38 (s, 2 H), 6.84 (td, J = 9.03, 2.26 Hz, 1 H), 6.96 (dd, J = 8.53, 4.27 Hz, 1 H), 7.25 (d, J = 8.50 Hz, 1 H), 7.43 (dd, J = 8.28, 2.26 Hz, 1 H), 7.61 (d, J = 8.28 Hz, 1 H) | 0.00672 | 13572 |
| 93 | N | C—H | 3-phenylpropyl | cyclopropyl | C—F | 1H NMR (400 MHz, DMSO-d6) δ ppm 0.80-0.92 (m, 2 H) 0.97-1.13 (m, 2 H) 1.89-2.05 (m, 2 H) 2.56-2.70 (m, 2 H) 2.83-2.99 (m, 1 H) 4.42 (t, J = 7.53 Hz, 2 H) 5.39 (s, 2 H) 6.87-6.98 (m, 1 H) 7.13-7.30 (m, 8 H) 8.02 (dd, J = 8.16, 1.38 Hz, 1 H) 8.37 (dd, J = 4.77, 1.51 Hz, 1 H) | 0.031484 | >3176 |

TABLE 4-continued

| | X4—R1 | X5—R1 | R2 | R3 | Y—R4 | 1H NMR | WT activity EC50 (μM) | SI CC50/EC50 |
|---|---|---|---|---|---|---|---|---|
| 94 | N | C—H | (propyl-2-pyridyl) | cyclopropyl | N | 1H NMR (400 MHz, DMSO-d6) δ ppm 0.75-0.96 (m, 2 H) 0.99-1.13 (m, 2 H) 2.03-2.20 (m, 2 H) 2.73-2.86 (m, 2 H) 2.91-3.06 (m, 1 H) 4.48 (t, J = 7.30 Hz, 2 H) 5.47 (s, 2 H) 7.12-7.34 (m, 4 H) 7.67 (dd, J = 8.03, 2.01 Hz, 1 H) 8.05 (d, J = 7.78 Hz, 1 H) 8.26 (d, J = 5.27 Hz, 1 H) 8.36 (d, J = 3.51 Hz, 1 H) 8.42 (s, 1 H) 8.46 (d, J = 4.02 Hz, 1 H) | 0.1258 | >748 |
| 95 | N | C—H | (propyl-5-methyl-1H-pyrazol-4-yl) | cyclopropyl | C—F | 1H NMR (400 MHz, DMSO-d6) δ ppm 0.78-0.92 (m, 2 H) 0.97-1.09 (m, 2 H) 1.90 (s, 2 H) 2.06 (br. s, 3 H) 2.28-2.42 (m, 2 H) 2.83-3.00 (m, 1 H) 4.39 (t, J = 7.40 Hz, 2 H) 5.37 (s, 2 H) 6.84-7.01 (m, 1 H) 7.14-7.30 (m, 4 H) 7.99 (dd, J = 8.03, 1.25 Hz, 1 H) 8.37 (dd, J = 4.64, 1.38 Hz, 1 H) | | |
| 96 | N | C—H | (propyl-5-methyl-1H-pyrazol-4-yl) | cyclopropyl | N | 1H NMR (400 MHz, DMSO-d6) δ ppm 0.77-0.96 (m, 2 H) 1.00-1.12 (m, 2 H) 1.86-1.98 (m, 2 H) 2.06 (br. s, 3 H) 2.37 (t, J = 7.78 Hz, 2 H) 2.97 (tt, J = 6.93, 3.48 Hz, 1 H) 4.40 (t, J = 7.15 Hz, 2 H) 5.43 (s, 2 H) 7.25 (dd, J = 8.16, 4.64 Hz, 2 H) 7.29 (d, J = 5.27 Hz, 1 H) 7.99 (d, J = 8.03 Hz, 1 H) 8.26 (d, J = 5.27 Hz, 1 H) 8.37 (dd, J = 4.77, 1.51 Hz, 1 H) 8.42 (s, 1 H) | | |
| 97 | N | CMe2NH2 | (isohexyl) | cyclopropyl | N | | | |
| 98 | N | C—H | (propyl-4-chlorophenyl) | cyclopropyl | N | 1H NMR (400 MHz, DMSO-d6) δ ppm 0.77-0.94 (m, 2 H) 0.98-1.13 (m, 2 H) 2.01 (quin, J = 7.72 Hz, 2 H) 2.58-2.73 (m, 2 H) 2.88-3.05 (m, 1 H) 4.42 (t, J = 7.53 Hz, 2 H) 5.46 (s, 2 H) 7.14-7.37 (m, 6 H) 8.04 (d, J = 7.53 Hz, 1 H) 8.27 (d, J = 5.27 Hz, 1 H) 8.36 (d, J = 4.27 Hz, 1 H) 8.44 (s, 1 H) | | |

TABLE 5
| | structure | ¹H NMR | WT activity EC₅₀ (μM) | SI CC₅₀/EC₅₀ |
|---|---|---|---|---|
| 62 | 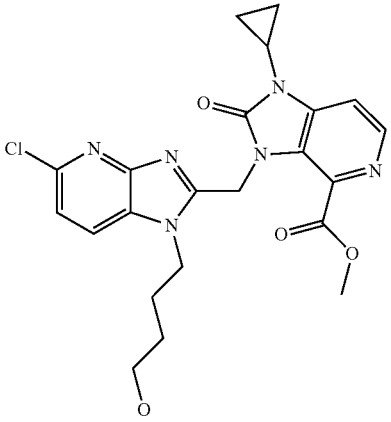 [SMILES: COC(=O)c1nccc2c1n(Cc1nc3nc(Cl)ccc3n1CCCCO)c(=O)n2C1CC1] | ¹H NMR (400 MHz, CHLOROFORM-d) δ ppm 1.04-1.11 (m, 2 H) 1.15-1.22 (m, 2 H) 1.65-1.73 (m, 2 H) 1.80 (br. s, 1 H) 1.98-2.15 (m, 2 H) 2.87-3.00 (m, 1 H) 3.70-3.80 (m, 5 H) 4.36 (t, J = 7.40 Hz, 2 H) 5.89 (s, 2 H) 7.18 (d, J = 8.28 Hz, 1 H) 7.35 (d, J = 5.02 Hz, 1 H) 7.63 (d, J = 8.53 Hz, 1 H) 8.40 (d, J = 5.27 Hz, 1 H) | 0.294144 | >339 |
| 49 | 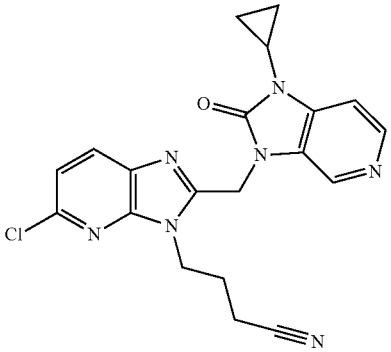 [SMILES: N#CCCCn1c(Cn2c(=O)n(C3CC3)c3ccncc32)nc2ccc(Cl)nc21] | | 1.450474 | >68 |
| 105 | 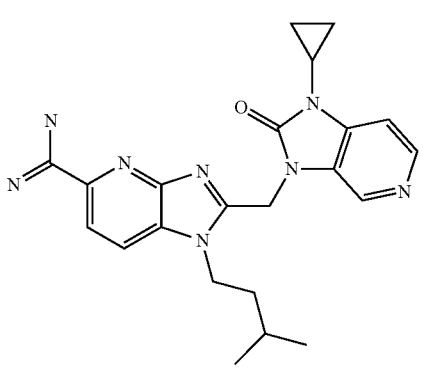 [SMILES: CC(C)CCn1c(Cn2c(=O)n(C3CC3)c3ccncc32)nc2nc(C(=N)N)ccc21] | | 0.000316 | >330179 |

The invention claimed is:

1. A method of treating a respiratory syncytial viral (RSV) infection comprising administering to a subject in need thereof an anti-virally effective amount of a compound of formula I, or a N-oxide, addition salt, quaternary amine, or a stereochemically isomeric form thereof,

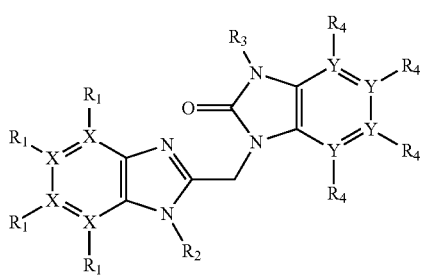

formula I wherein each X is independently C or N, wherein at least one X is N;

each Y is independently C or N;

each $R_1$ is selected from the group consisting of H, halogen, $C_1$-$C_6$alkyl, $C_3$-$C_7$cycloalkyl, $C_1$-$C_6$alkoxy, $N(R_5)_2$, $CO(R_6)$, $CH_2NH_2$, $CH_2OH$, CN, C(=NOH)$NH_2$, C(=NOCH$_3$)NH$_2$, C(=NH)NH$_2$, $CF_3$, $OCF_3$, $B(OH)_2$, and $B(O-C_1-C_6$alkyl$)_2$, wherein if X is C, $R_1$ is present, and if X is N, $R_1$ is absent;

$R_2$ is —(CR$_7$R$_8$)$_n$-R$_9$;

$R_3$ is selected from the group consisting of H, $C_1$-$C_{10}$alkyl, $C_3$-$C_7$cycloalkyl, $C_2$-$C_{10}$alkenyl, $SO_2$-$R_7$, $CH_2CF_3$ and a 4 to 6 membered saturated ring containing an oxygen atom;

each $R_4$ is independently selected from the group consisting of H, $C_1$-$C_6$alkyl, $C_1$-$C_6$cycloalkyl, $C_1$-$C_6$alkoxy, $CO(R_7)$, $COO(R_7)$, $CF_3$ and halogen, wherein if Y is C, $R_4$ is present, and if Y is N, $R_4$ is absent;

each $R_5$ is independently selected from the group consisting of H, $C_1$-$C_6$alkyl, $COOCH_3$, and $CONHSO_2CH_3$;

each $R_6$ is independently selected from the group consisting of OH, O($C_1$-$C_6$alkyl), $NH_2$, $NHSO_2N(C_1$-$C_6$alkyl$)_2$, $NHSO_2NHCH_3$, $NHSO_2(C_1$-$C_6$alkyl), $NHSO_2(C_3$-$C_7$cycloalkyl), and $N(C_1$-$C_6$-alkyl$)_2$;

$R_7$ and $R_8$ are each independently selected from the group consisting of H, $C_1$-$C_{10}$alkyl, and $C_3$-$C_7$cycloalkyl, or $R_7$ and $R_8$ taken together form a 4 to 6 membered aliphatic ring, said ring optionally contains a heteroatom selected from the group consisting of N, S, and O;

$R_9$ is selected from the group consisting of H, $R_{10}$, $C_1$-$C_6$alkyl, OH, CN, F, $CF_2H$, $CF_3$, $CONR_7R_8$, $COOR_7$, $CON(R_7)SO_2R_8$, $CON(R_7)SO_2N(R_7R_8)$, $NR_7R_8$, $NR_7COOR_8$, $OCOR_7$, O-Benzyl, $NR_7SO_2R_8$, $SO_2NR_7R_8$, $SO_2R_2$, $OCONR_7R_8$, $OCONR_7R_{10}$, $N(R_7)CON(R_7R_8)$, $N(R_7)COOR_{10}$, phtalimido, 2-methyl-benzothiophene(1,1)dioxide, and a 4 to 6 membered saturated ring containing an oxygen atom;

n is an integer from 2 to 6; and $R_{10}$ is selected from the group consisting of $C_1$-$C_6$ alkyl, $C_3$-$C_7$cycloalkyl, phenyl, pyridine and pyrazole, wherein $R_{10}$ is optionally substituted with one or more substituents comprising $CF_3$, $CH_3$, $OCH_3$, $OCF_3$ or halogen.

2. A method according to claim 1 wherein $R_3$ is selected from the group consisting of H, $C_1$-$C_{10}$alkyl, $C_3$-$C_7$cycloalkyl, $C_2$-$C_{10}$alkenyl, $SO_2$-$R_2$, and a 4 to 6 membered saturated ring containing an oxygen atom; and $R_9$ is selected from the group consisting of H, $C_1$-$C_6$alkyl, OH, CN, F, $CF_2H$, $CF_3$, $CONR_7R_8$, $COOR_7$, $CON(R_2)SO_2R_8$, $CON(R_7)SO_2N(R_7R_8)$, $NR_7R_8$, $NR_7COOR_8$, $OCOR_7$, O-Benzyl, $NR_7SO_2R_8$, $SO_2NR_7R_8$, $SO_2R_7$, and a 4 to 6 membered saturated ring containing an oxygen atom.

3. A method according to claim 1 wherein one X is N, said N being in either of the two positions ortho to the imidazole ring.

4. A method according to claim 1, wherein $R_1$ is H or halogen.

5. A method according to claim 1, wherein $R_1$ in the para position to C—N—$R_2$ is selected from the group consisting of H, halogen, and $CH_2$—$NH_2$, and all other $R_1$ are H.

6. A method according to claim 1, wherein $R_7$ and $R_8$ are H, and n is 2-4.

7. A method according to claim 1, wherein $R_9$ is selected from the group consisting of OH, F, $CF_2H$, $CF_3$, $C_1$-$C_6$alkyl, and $SO_2R_7$.

8. A method according to claim 1, wherein $R_3$ is selected from the group consisting of $C_3$-$C_7$cycloalkyl, and a 4 membered saturated hydrocarbon containing an oxygen atom.

9. A method according to claim 1, wherein $R_3$ is cyclopropyl or $CH_2CF_3$.

10. A method according to claim 1, wherein the Y that is in para position to N—$R_3$ is N, and each other Y is C.

11. A method according to claim 10, wherein the $R_4$ on the Y that is in para position to N—$R_3$ is F.

12. A method according to claim 1, wherein each $R_4$ is H.

* * * * *